(12) United States Patent
Wada et al.

(10) Patent No.: US 9,863,936 B2
(45) Date of Patent: Jan. 9, 2018

(54) NUCLEIC ACID CONSTRUCT, NUCLEIC ACID-PROTEIN COMPLEX, AND USE THEREOF

(75) Inventors: Akira Wada, Saitama (JP); Hiroyuki Osada, Saitama (JP)

(73) Assignee: RIKEN, Saitama (JP)

( * ) Notice: Subject to any disclaimer, the term of this patent is extended or adjusted under 35 U.S.C. 154(b) by 0 days.

(21) Appl. No.: 14/119,730

(22) PCT Filed: May 23, 2012

(86) PCT No.: PCT/JP2012/063221
§ 371 (c)(1),
(2), (4) Date: Nov. 22, 2013

(87) PCT Pub. No.: WO2012/161227
PCT Pub. Date: Nov. 29, 2012

(65) Prior Publication Data
US 2014/0206560 A1    Jul. 24, 2014

(30) Foreign Application Priority Data
May 23, 2011 (JP) .............................. 2011-115166

(51) Int. Cl.
| | |
|---|---|
| A61K 38/16 | (2006.01) |
| C07H 21/04 | (2006.01) |
| C40B 30/04 | (2006.01) |
| C12N 15/00 | (2006.01) |
| C12P 21/06 | (2006.01) |
| G01N 33/53 | (2006.01) |
| C07K 17/10 | (2006.01) |
| C12N 15/10 | (2006.01) |

(52) U.S. Cl.
CPC ......... *G01N 33/5308* (2013.01); *C07K 17/10* (2013.01); *C12N 15/1041* (2013.01); *C07H 21/04* (2013.01); *C07K 2319/80* (2013.01); *C07K 2319/85* (2013.01); *C12N 15/1034* (2013.01); *C12N 2800/00* (2013.01)

(58) Field of Classification Search
CPC  C07H 21/04; C07K 2319/85; C12N 15/1034; C12N 15/1041; C12N 2800/00; G01N 33/5308
USPC .................. 435/320.1, 69.1; 506/9; 530/358; 536/23.4, 23.7, 24.1
See application file for complete search history.

(56) References Cited

U.S. PATENT DOCUMENTS

| | | | | |
|---|---|---|---|---|
| 5,198,346 | A | * | 3/1993 | Ladner ................. C07K 14/005 435/252.3 |
| 5,643,768 | A | | 7/1997 | Kawasaki |
| 5,658,754 | A | | 8/1997 | Kawasaki |
| 5,882,893 | A | * | 3/1999 | Goodearl ..................... 435/69.1 |
| 6,348,315 | B1 | | 2/2002 | Pluckthun et al. |
| 6,589,741 | B2 | | 7/2003 | Pluckthun et al. |
| 6,620,587 | B1 | | 9/2003 | Taussig et al. |
| 2002/0115083 | A1 | | 8/2002 | Pluckthun et al. |

FOREIGN PATENT DOCUMENTS

| | | |
|---|---|---|
| JP | 3127158 | 11/2000 |
| JP | 2001-521395 | 11/2001 |
| JP | 2002-500514 | 1/2002 |
| JP | 2007-29061 | 2/2007 |
| WO | 01/75097 | 10/2001 |

OTHER PUBLICATIONS

Sawata et al., 2003, Protein Engineering, vol. 16, No. 12, pp. 1115-1124, IDS.*
Austin et al., "Designed Arginine-Rich RNA-Binding Peptides with Picomolar Affinity", J. Am. Chem. Soc., vol. 124, pp. 10966-10967, 2002.
Hanes et al., "In Vitro Selection and Evolution of Functional Proteins by Using Ribosome Display", Proc. Natl. Acad. Sci., vol. 94, pp. 4937-4942, 1997.
Wada et al., "Ribosome Display Selection of a Metal-Binding Motif From an Artificial Peptide Library", Biotechnology and Bioengineering, vol. 101, No. 5, pp. 1102-1107, 2008.
Greenbaum, "How Tat Targets TAR: Structure of the BIV Peptide-RNA Complex", Structure, vol. 4, pp. 5-9, 1996.
Zhou et al., "A Novel Strategy by the Action of Ricin that Connects Phenotype and Genotype without Loss of the Diversity of Libraries", J. Am. Chem. Soc., vol. 124, No. 4, pp. 538-43, 2002.
Sawata et al., "Modified Peptide Selection in Vitro by Introduction of a Protein-RNA Interaction", Protein Engineering, vol. 16, No. 12, pp. 1115-1124, 2003.
International Search Report issued with respect to PCT/JP2012/063221, dated Aug. 28, 2012.
International Preliminary Report on Patentability issued with respect to PCT/JP2012/063221, dated Dec. 5, 2013.

* cited by examiner

*Primary Examiner* — Shin Lin Chen
(74) *Attorney, Agent, or Firm* — Greenblum & Bernstein, P.L.C.

(57) ABSTRACT

Using a nucleic acid construct, association of a polypeptide with a sequence coding therefor and screening of a polypeptide that binds to a target substance are carried out, which nucleic acid construct comprises a 5'-untranslated region and a coding region, wherein the above-mentioned coding region comprises a sequence coding for a polypeptide subjected to be displayed, a sequence coding for a first nucleic acid binding polypeptide, and a sequence coding for a second nucleic acid binding polypeptide; the above-mentioned 5'-untranslated region comprises a first sequence capable of binding to a first nucleic acid binding polypeptide and a second sequence capable of binding to second nucleic acid binding polypeptide; and, when the above-mentioned nucleic acid construct is introduced in a translation system, a fusion protein translated from the coding region of the above-mentioned nucleic acid construct forms a complex with an RNA corresponding to the above-mentioned nucleic acid construct.

16 Claims, 3 Drawing Sheets

[Fig. 1]
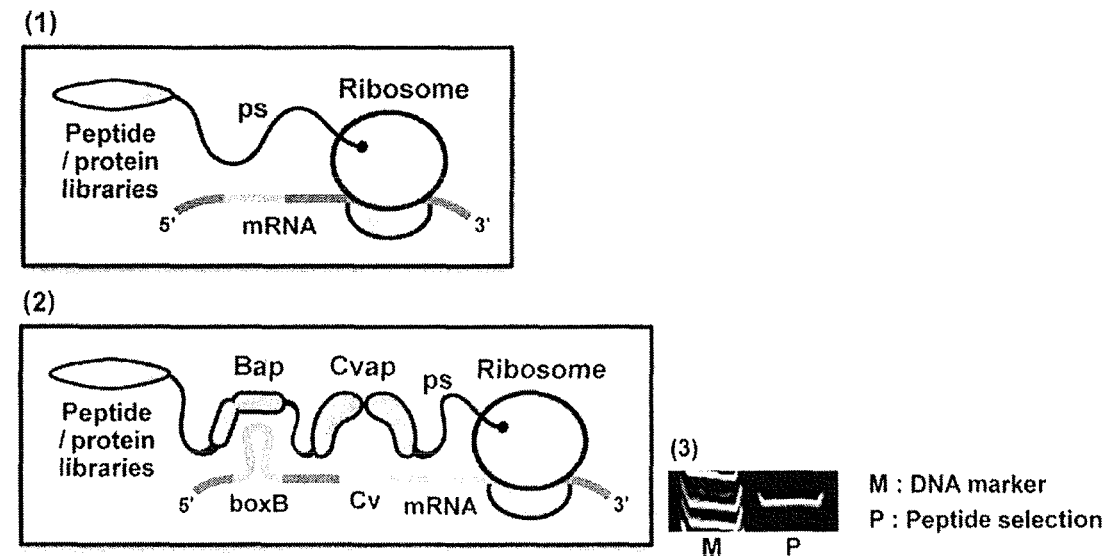
[Fig. 2]
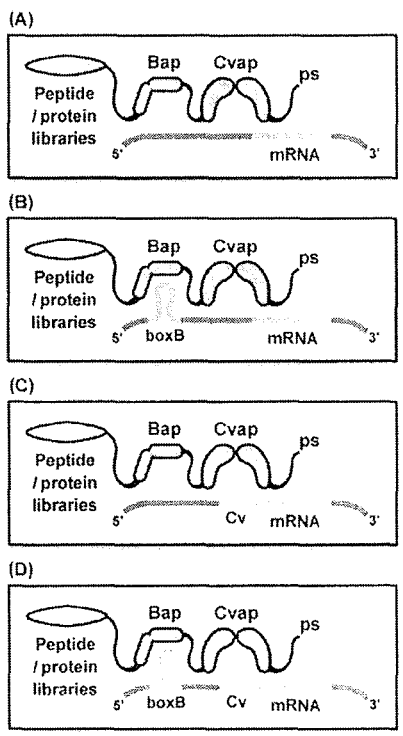

[Fig. 3]
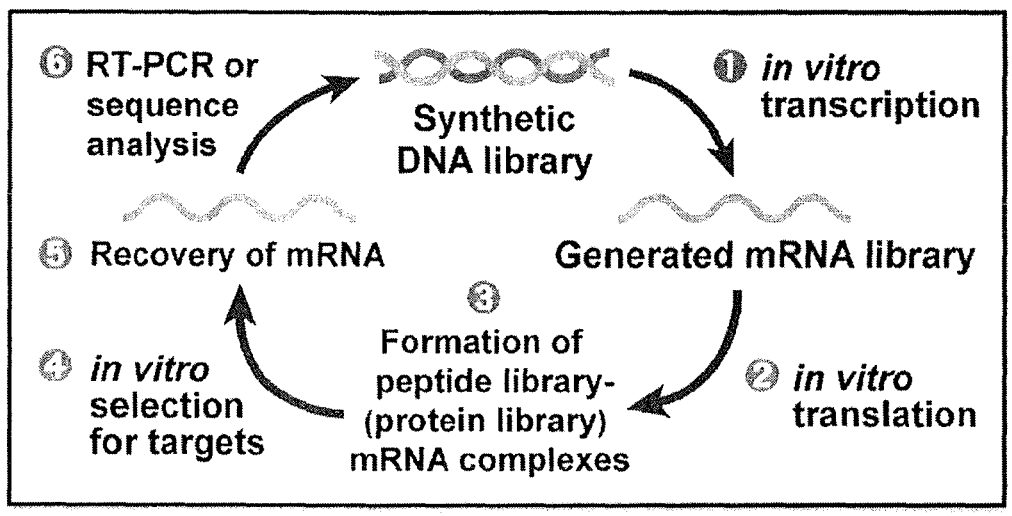
[Fig. 4]
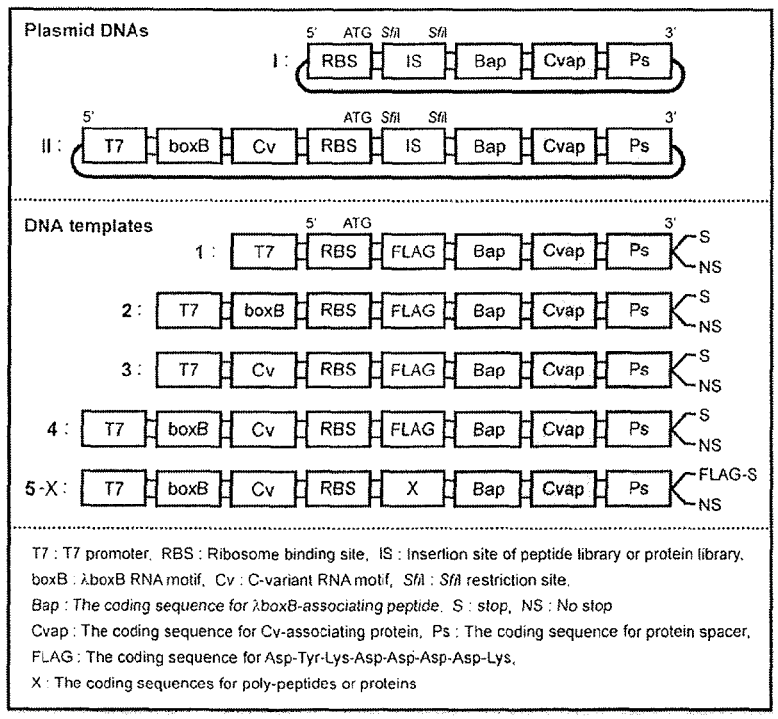
[Fig. 5]
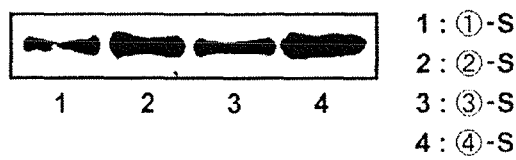

[Fig. 6]
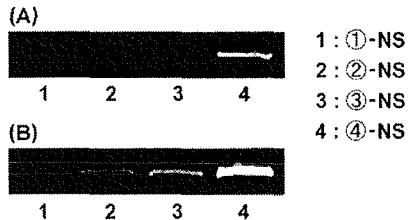
1 : ①-NS
2 : ②-NS
3 : ③-NS
4 : ④-NS
[Fig. 7]
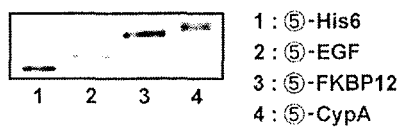
1 : ⑤-His6
2 : ⑤-EGF
3 : ⑤-FKBP12
4 : ⑤-CypA
[Fig. 8]
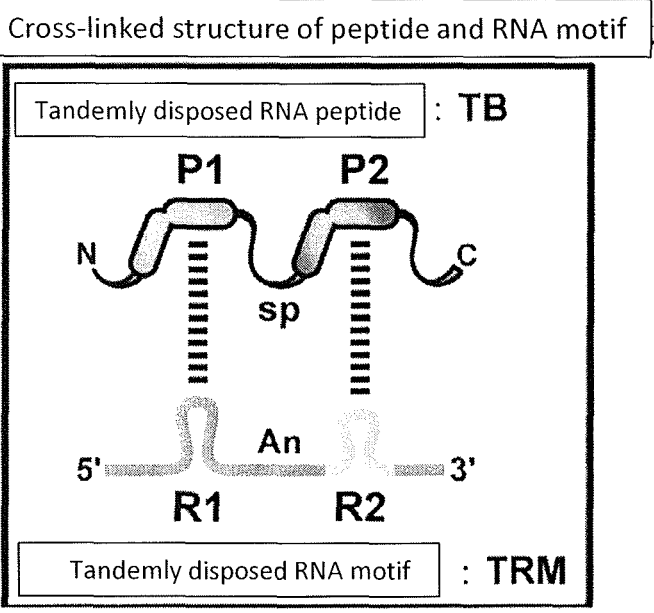
Cross-linked structure of peptide and RNA motif
Tandemly disposed RNA peptide : TB
Tandemly disposed RNA motif : TRM
[Fig. 9]
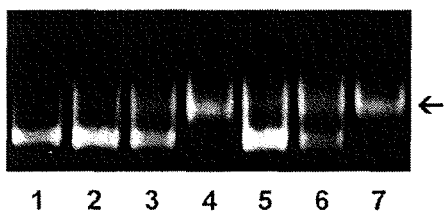

NUCLEIC ACID CONSTRUCT, NUCLEIC ACID-PROTEIN COMPLEX, AND USE THEREOF

SEQUENCE LISTING

The instant application contains a Sequence Listing which has been submitted electronically in ASCII format and is hereby incorporated by reference in its entirety. Said ASCII copy, created on Jan. 29, 2014, is named P44913_SL.txt and is 170,001 bytes in size.

TECHNICAL FIELD

The present invention relates to a nucleic acid construct capable of expressing a polypeptide in association with a nucleic acid sequence coding therefor and a kit including the nucleic acid construct, and a method of displaying a polypeptide on nucleic acids and of selecting a polypeptide sequence that binds to a target substance using the nucleic acid construct.

BACKGROUND ART

The term "peptide aptamer" is a general term for an artificial peptide that binds specifically to a specific target molecule. At present, small peptide aptamers that exhibit binding functions similar to "antibodies" have drawn much attention as probes for molecular detection, inhibitors of a biological functions, or the like in both chemical research and biological science research. Further, in the field of medicine, they are also expected to serve as molecular target drugs for the next generation in place of antibody pharmaceuticals.

Recently, a phage display method has been mainly used as a technique of creating peptide aptamers. In this technique, a strategy employed is to select a peptide aptamer that specifically binds to a target molecule from about $10^9$ kinds of peptide libraries that are displayed on part of a coat protein of a phage. Yet, there are a number of problems remained to be solved. For instance, (1) in a process of selecting the peptide aptamer, the life cycle of *Escherichia coli* and phages is utilized and therefore peptides that adversely affect their life activity end up being automatically eliminated. Hence, a phenomenon that no peptide aptamers having an intended function are obtained often takes place. Further, (2) there is bias in the occurrence frequency of each of the codons coding for 20 kinds of amino acids in cells, and there is concern in that a large gap is created between the variety of theoretically designed-synthesized peptide libraries and that of libraries actually used. Furthermore, (3) what frequently happens to a peptide aptamer selected by this technique is a phenomenon that the properties to bind to a target molecule end up decreasing or disappearing in a state where it is separated from the coat protein of phage. That's because a state where the peptide aptamer and the protein derived from the phage are fused is essential for developing and maintaining the binding property to the target molecule. In the case of using the phage display method, this is an unavoidable serious issue. Hence, in order to avoid the above problem, it is required to construct a peptide library or protein library by not using living cells but using only intracellular translation reactions. And, development of an "in vitro display method", by which a peptide aptamer specifically binding to an intended target molecule can be efficiently selected from a library, is imperative.

As such an in vitro display method, there has been a ribosome display method (Patent documents 1 to 4 and Non-patent document 1). As compared with a mRNA display method, in the ribosome display method, peptide (protein) libraries of various sizes can be designed and utilized in accordance with research applications and furthermore, an intended peptide aptamer can be selected and identified from those libraries by a quick and simple process. Therefore, the research can evolve with a view to commissioning and supplying in a kit or automation by robots in the future. However, because a peptide-ribosome-mRNA complex peptide aptamer that is used in the selection process is very unstable, it often happens that the intended peptide aptamer can not be identified. Therefore, even throughout the world, very few researchers are capable of freely dealing with this principle, condition, and technique in the present situation.

In order to increase the stability of the peptide-ribosome-mRNA complex, Non-patent document 2 discloses a technique in which Cv sequences are incorporated into the 5'-untranslated region of mRNA and Cvap dimer is included in a polypeptide to be expressed to carry out a ribosome display (Non-patent document 2). Yet, in order to increase the efficiency of the ribosome display, further improvement has been demanded.

PRIOR ART DOCUMENTS

Patent Documents

Patent document 1: Japanese Patent Publication No. 3127158
Patent document 2: Japanese Translated PCT Patent Application Laid-open No. 2001-521395
Patent document 3: Japanese Translated PCT Patent Application Laid-open No. 2002-500514
Patent document 4: WO 01/75097

Non-Patent Documents

Non-patent document 1: Proc Natl Acad Sci USA, vol. 94, p. 4937-4942, 1997
Non-patent document 2: Biotechnology and Bioengineering vol. 101, No. 5, Dec. 1, 2008

SUMMARY OF THE INVENTION

An object of the present invention is to provide a technique whereby a complex of a polypeptide and a nucleic acid containing a sequence coding therefor can be stably and efficiently formed; and therefore association of a polypeptide with the sequence coding therefor and screening of a polypeptide that binds to a target substance can be efficiently carried out.

In view of the above, in order to solve these problems, the present inventors intensively study to successfully construct a new template in which a peptide and protein that specifically binds to two small RNA motifs are introduced, and in which RNA motifs are introduced into the 5' end of mRNA; and to stabilize the complex by intramolecular association with affinities concurrently with an in vitro translation reaction. Further, the inventors also successfully dissociated the ribosome from the complex to synthesize a new complex and carried out a peptide selection experiment using it (stable cross-linking type ribosome display method), thereby completing the present invention based on these successes.

Accordingly, the present invention provides the following.

[1] A nucleic acid construct comprising a 5'-untranslated region and a coding region, wherein said coding region comprises a sequence coding for a polypeptide subjected to be displayed, a sequence coding for a first nucleic acid binding polypeptide, and a sequence coding for a second nucleic acid binding polypeptide; and wherein the 5'-untranslated region comprises a first sequence capable of binding to the first nucleic acid binding polypeptide and a second sequence capable of binding to the second nucleic acid binding polypeptide; and, when the nucleic acid construct is introduced in a translation system, a fusion protein translated from the coding region of the nucleic acid construct forms a complex with an RNA corresponding to the nucleic acid construct by a bond between the first nucleic acid binding polypeptide and the first sequence and a bond between the second nucleic acid binding polypeptide and the second sequence.

[2] The nucleic acid construct according to [1], wherein the first nucleic acid binding polypeptide and the second nucleic acid binding polypeptide are a boxB-associating peptide (Bap) and a Cv-associating peptide (Cvap) dimer; and the first sequence and the second sequence are a boxB sequence and a Cv sequence.

[3] The nucleic acid construct according to [1], wherein the first nucleic acid binding polypeptide and the second nucleic acid binding polypeptide are Bap and Rev; and the first sequence and the second sequence are a boxB sequence and an apI sequence or an apII sequence.

[4] The nucleic acid construct according to [1], wherein the first nucleic acid binding polypeptide and the second nucleic acid binding polypeptide are Bap and BIV Tat; and the first sequence and the second sequence are a boxB sequence and a BIV TAR sequence.

[5] The nucleic acid construct according to [2], wherein the above-mentioned 5'-untranslated region comprises the boxB sequence, the Cv sequence, and a ribosome binding sequence; and the above-mentioned coding region comprises a sequence coding for a polypeptide subjected to be displayed, a Bap-coding sequence, a Cvap dimer-coding sequence, and a spacer-coding sequence that are linked in frame.

[6] The nucleic acid construct according to [3], wherein the above-mentioned 5'-untranslated region comprises the boxB sequence, the apI sequence or the apII sequence, and a ribosome binding sequence; and the above-mentioned coding region comprises a sequence coding for a polypeptide subjected to be displayed, a Bap-coding sequence, a Rev-coding sequence, and a spacer-coding sequence that are linked in frame.

[7] The nucleic acid construct according to [4], wherein the above-mentioned 5'-untranslated region comprises the boxB sequence, the BIV TAR sequence, and a ribosome binding sequence; and the above-mentioned coding region comprises a sequence coding for a polypeptide subjected to be displayed, Bap-coding sequence, BIV Tat-coding sequence, and spacer-coding sequence that are linked in frame.

[8] The nucleic acid construct according to any [1] to [4], wherein the above-mentioned 5'-untranslated region comprises a ribosome binding sequence.

[9] The nucleic acid construct according to any [1] to [8], wherein the sequence coding for a polypeptide subjected to be displayed is a sequence coding for a random polypeptide.

[10] A nucleic acid-protein complex comprising
a nucleic acid construct comprising a 5'-untranslated region and a coding region and
a fusion protein translated from the coding region, wherein the coding region comprises a sequence coding for a polypeptide subjected to be displayed, a sequence coding for a first nucleic acid binding polypeptide and a sequence coding for a second nucleic acid binding polypeptide; and
the 5'-untranslated region comprises a first sequence capable of binding to the first nucleic acid binding polypeptide and a second sequence capable of binding to the second nucleic acid binding polypeptide; which nucleic acid-protein complex is formed by a bond between the first nucleic acid binding polypeptide and the first sequence, and a bond between the second nucleic acid binding polypeptide and the second sequence.

[11] The nucleic acid-protein complex according to [10] that does not comprise a ribosome.

[12] The nucleic acid-protein complex according to [10] or [11], wherein the first nucleic acid binding polypeptide and the second nucleic acid binding polypeptide are Bap and Cvap dimer; and the first sequence and the second sequence are a boxB sequence and a Cv sequence.

[13] The nucleic acid-protein complex according to any of claims [10] to [12], wherein the sequence coding for a polypeptide subjected to be displayed is a sequence coding for a random polypeptide.

[14] A method of displaying a polypeptide on a nucleic acid comprising introducing the nucleic acid construct according to any of [1] to [9] in a translation system to express a fusion protein encoded by the coding region, forming the complex of the fusion protein and the RNA corresponding to the nucleic acid construct via the bond between the first nucleic acid binding polypeptide and the first sequence; and the bond of the second nucleic acid binding polypeptide and the second sequence; and thereby displaying the polypeptide subjected to be displayed on the RNA corresponding to the nucleic acid construct.

[15] The method according to [14] further comprising the step of dissociating the ribosome from the nucleic acid construct after forming the complex of the fusion protein and the RNA corresponding to the nucleic acid construct.

[16] A method of selecting a polypeptide sequence that binds to a target substance, comprising repeating the following steps (1) to (3):
(1) the step of expressing fusion proteins of a random polypeptide, the first nucleic acid binding polypeptide, and the second nucleic acid binding polypeptide from the nucleic acid construct according to [9]; to display a random polypeptide library on the RNA corresponding to the nucleic acid construct;
(2) the step of bringing a target substance into contact with the library; and
(3) the step of selecting a fusion protein comprising the polypeptide sequence that binds to the target substance and amplifying the nucleic acid sequence coding for the selected fusion protein.

[17] The method according to [16] further comprising the step of dissociating the ribosome from the nucleic acid construct between the steps (1) and (2).

[18] A kit for displaying a polypeptide on a nucleic acid, the kit comprising the nucleic acid construct according to any of [1] to [9].

According to the method of the present invention, a complex of a polypeptide and a nucleic acid containing a sequence coding therefor can be stably and efficiently formed, and thereby association of a polypeptide with the sequence coding therefor and screening of a polypeptide that binds to a target substance can be efficiently carried out.

In addition, according to the method of the present invention, the complex of the polypeptide and the nucleic acid containing a sequence coding therefor can be maintained even when the ribosome is removed after the formation of the peptide-ribosome-RNA complex, and therefore "steric hindrance between the ribosome of the complex and the target molecule" which has been another problem of the ribosome display method can be completely resolved. This made it possible to eliminate non-specific binding to the ribosome and, at the same time, to select a peptide aptamer having properties of more strongly binding to a target, which peptide aptamer has not been able to be selected thus far.

BRIEF DESCRIPTION OF THE DRAWINGS

FIG. 1 is a schematic diagram of a complex (1) that is used in a conventional ribosome display method and a novel complex (2) that is used in a stable cross-linking type ribosome display method. Ps represents a spacer sequence. (3) is a photograph of electrophoresis showing that a FLAG peptide expressed using the complex (2) was selected by an anti-FLAG antibody and a sequence coding therefor was able to be specifically amplified.

FIG. 2 is a schematic diagram of a peptide-mRNA complex when mRNAs were transcribed from (A) DNA template 1-S, (B) DNA template 2-S, (C) DNA template 3-S, and (D) DNA template 4-S of Example 2, translated to form peptide-ribosome-mRNA complexes and then the ribosome were dissociated.

FIG. 3 is a figure showing an operation scheme for carrying out a FLAG peptide selection experiment utilizing a stable cross-linking type ribosome display method and stable cross-linking type display method.

FIG. 4 is a sequence and explanation of plasmid DNA for synthesizing each complex used in a stable cross-linking type ribosome display method and stable cross-linking type display method, and various DNA templates prepared based thereon. FIG. 4 discloses the FLAG sequence as SEQ ID NO: 67.

FIG. 5 is a figure (photograph) checking, by Western blotting, whether or not each of the proteins (Example 2, SEQ ID NOs: 10, 12, 14, and 16) for forming each of the complexes used in a stable cross-linking type display method were expressed in vitro.

FIG. 6 is a figure (photograph) showing the results of a FLAG peptide selection experiment that was carried out using each of the complexes of FIG. 2; (A) 18 cycles and (B) 21 cycles.

FIG. 7 is a figure (photograph) of results when polypeptide and protein having various sizes were introduced into the plasmid II of FIG. 4 to prepare as templates of 5-X of FIG. 4 and then in vitro expression of those proteins was checked by Western blotting. FIG. 7 discloses "His6" as SEQ ID NO: 66.

FIG. 8 shows a RNA motif-peptide cross-linked structure.

FIG. 9 is a photograph of electrophoresis showing formation of RNA motif-peptide cross-linked structures (lane 1: TRM4 alone, lane 2: TRM4+TP3 (0.25 eq.), lane 3: TRM4+TP3 (0.5 eq.), lane 4: TRM4+TP3 (1 eq.), lane 5: TRM4+TP4 (0.25 eq.). lane 6: TRM4+TP4 (0.5 eq.), and lane 7: TRM4+TP4 (1 eq.)).

DESCRIPTION OF THE EMBODIMENTS

<Nucleic Acid Construct>

The nucleic acid construct of the present invention comprises a 5'-untranslated region and a coding region, wherein the coding region comprises a sequence coding for a polypeptide subjected to be displayed, a sequence coding for a first nucleic acid binding polypeptide, and a sequence coding for a second nucleic acid binding polypeptide, and the 5'-untranslated region comprises a first sequence capable of binding to a first nucleic acid binding polypeptide and a second sequence capable of binding to second nucleic acid binding polypeptide.

And, when the nucleic acid construct of the present invention is introduced into a translation system, a fusion protein that is translated from the above-mentioned coding region forms a complex of the RNA corresponding to the nucleic acid construct by the first nucleic acid binding polypeptide and the second nucleic acid binding polypeptide contained in such a fusion protein binding to a first sequence and a second sequence of the 5'-untranslated region, respectively.

Here, combination between the first nucleic acid binding polypeptide and the first sequence and combination between the second nucleic acid binding polypeptide and the second sequence can be any combination as long as it is a combination capable of forming a stable nucleic acid-polypeptide bond. A known nucleic acid sequence-nucleic acid binding polypeptide can be used. Concrete examples thereof include boxB-associating peptide (Bap) and boxB sequence; and Cv-associating peptide (Cvap) and Cv sequence. Of these, preferred are Bap and boxB sequence; and Cvap and Cv sequence. The combination between the first nucleic acid binding polypeptide and the first sequence and the combination between the second nucleic acid binding polypeptide and the second sequence may be the same combination but preferably are different combinations.

Here, boxB sequence refers to the boxB sequence of λ phage (Lazinski, D., Grzadzielska, E., and Das, A. Cell 1989, 59, 207-218; Legault, P., Li, J., Mogridge, J., Kay, L. E., and Greenblatt, J. Cell 1998, 93, 289-299), and examples of the boxB sequence contained in the nucleic acid construct of the present invention include a sequence represented by the base numbers 20 to 35 of SEQ ID NO: 5 (in the case of RNA, T shall be deemed to be replaced with U: SEQ ID NO: 38). It is to be noted that, as long as Bap is able to bind, one to several (for example, two or three) bases may be substituted, deleted, or added in this sequence.

Cv sequence refers to C-variant RNA (Nucleic Acids Research Supplement No. 1 99-100) and examples of the Cv sequence contained in the nucleic acid construct of the present invention include a sequence represented by the base numbers 41 to 59 of SEQ ID NO: 5 (in the case of RNA, T shall be deemed to be replaced with U). It is to be noted that, as long as Cvap is able to bind, one to several (for example, two or three) bases may be substituted, deleted, or added in this sequence.

In the 5'-untranslated region, either the first sequence or the second sequence may be in the 5' side in the sequence. For either one or both of these, two or more sequences may present.

It is preferred to be 3 to 15 bases between the first sequence and the second sequence from the aspect of stabilization of the protein-RNA complex.

And, in the 5'-untranslated region, it is preferred that a ribosome binding sequence (RBS) be present following the first sequence and the second sequence. In that case, it is preferred to be 30 to 40 bases between the sequence of whichever the first sequence or the second sequence is present in the 3' side and the ribosome binding sequence from an aspect of ease of ribosome's binding.

Examples of the ribosome binding sequence include a Shine-Dalgarno (SD) sequence, as exemplified by a sequence of base numbers 92 to 97 of the SEQ ID NO: 5.

Bap-coding sequence contained in the coding region refers to a sequence coding for Bap (Legault, P., Li, J., Mogridge, J., Kay, L. E., and Greenblatt, J. Cell 1998, 93, 289-299; Austin, R. J., Xia, T., Ren, J., Takahashi, T. T., and Roberts, R. W. J. Am. Chem. Soc. 2002, 124, 10966-10967). Examples of the sequence include a sequence coding for the amino acid numbers 23 to 45 of SEQ ID NO: 6 (SEQ ID NO: 33) and more concrete examples thereof include a sequence represented by the base numbers 172 to 240 of SEQ ID NO: 5. It is to be noted that, as long as it is able to bind to the above-mentioned boxB sequence, one to several (for example, two or three) amino acids may be substituted, deleted, or added in the amino acid sequence of SEQ ID NO: 33.

Cvap dimer-coding sequence contained in the coding region refers to a sequence containing two of the sequences coding for Cvap (Rowsell, S., Stonehouse, N. J., Convery, M. A., Adams, C. J., Ellington, A. D., Hirao, I., Peabody, D. S., Stockley, P. G., and Phillips, S E. Nat. Strict. Biol. 1998, 5, 970-975; Wada, A., Sawata, S. Y., and Ito, Y. Biotechnol. Bioeng. 2008, 101, 1102-1107).

Examples of Cvap coding sequence include a sequence coding for the amino acid numbers 70 to 199 of SEQ ID NO: 6 and more concrete examples thereof include a sequence represented by the base numbers 313 to 702 of SEQ ID NO: 5. It is to be noted that, as long as it is able to bind to the above-mentioned Cv sequence, one to several (for example, 2 to 5 or 2 to 10) amino acids may be substituted, deleted or added in an amino acid sequence of the amino acid numbers 70 to 199 of SEQ ID NO: 6.

Cvap is known to be a dimer and to bind to the Cv sequence and two of the above-mentioned Cvap coding sequences thus need to be contained in the coding region. The Cvap dimer-coding sequence may be one in which two of the Cvap coding sequence are back to back linked or may be a sequence in which two of the Cvap coding sequence are linked via a linker coding sequence therebetween.

Further, the first nucleic acid binding polypeptide and the second nucleic acid binding polypeptide may be boxB-associating peptide (Bap) and Rev (TRQARRNRRRRWR-ERQR: SEQ ID NO: 34); and the first sequence and the second sequence may be boxB sequence and apI sequence (5'-GGCUGGACUCGUACUUCGGUACUGGA-GAAACAGCC-3': SEQ ID NO: 39) or apII (5'-GGUGU-CUUGGAGUGCUGAUCGGACACC-3': SEQ ID NO: 40) sequence.

Further, the first nucleic acid binding polypeptide and the second nucleic acid binding polypeptide may be boxB-associating peptide (Bap) and BIV Tat (SGPRPRGTRGK-GRRIRR: SEQ ID NO: 35) and the first sequence and the second sequence may be boxB sequence and BIV TAR sequence (5'-GCUCGUGUAGCUCAUUAGCUCCGAGC-3': SEQ ID NO: 41).

Although examples of a sequence of Rev include SEQ ID NO: 34, as long as it is able to bind to the above-mentioned apI or apII sequence, one to several (for example, two or three) amino acids may be substituted, deleted or added in the amino acid sequence of SEQ ID NO: 34.

Although examples of a sequence of BIV Tat include SEQ ID NO: 35, as long as it is able to bind to the above-mentioned BIV TAR sequence, one to several (for example, two or three) amino acids may be substituted, deleted or added in the amino acid sequence of SEQ ID NO: 35.

Also in each of the sequences of other polypeptides illustrated as examples, as long as it is able to bind to a target sequence, one to several (for example, two or three) amino acids are substituted, deleted or added.

The nucleic acid binding polypeptide is not limited to the above. The polypeptide can be any as long as it is able to bind to the nucleic acid sequence. It is preferred to use a polypeptide with the total number of Rs and Ks of 6 or more in the peptide sequence thereof or a polypeptide with the number of Rs of 7 or more in the peptide sequence thereof.

Further, preferably used is a polypeptide in which one or more kinds of RXR sequence (X is any amino acid), $RX_1X_2R$ sequence (SEQ ID NO: 42, $X_1$ and $X_2$ are any amino acid), and RR sequence; more preferably two or more kinds; and in particular preferably all of the three kinds are present in the peptide sequence thereof.

Further, preferably used is a polypeptide in which one or more kinds of RXR sequence, $RX_1X_2R$ sequence (SEQ ID NO: 42, $X_1$ and $X_2$ are any amino acid), RRXRR sequence (SEQ ID NO: 43, X is any amino acid); more preferably two or more kinds; and in particular preferably all of the three kinds are present in the peptide sequence thereof.

As the first nucleic acid binding polypeptide and the second nucleic acid binding polypeptide, two kinds of polypeptide described above may be selected to use. Besides, concrete examples thereof include the following.

HIV-1 Tat:
(SEQ ID NO: 44)
GRKKRRQRRR (10 mer)

JDV Tat:
(SEQ ID NO: 45)
GRRKKRGTRGKGRKIHY (17 mer)

λ N:
(SEQ ID NO: 46)
MDAQTRRRERRAEKQAQWKAAN (22 mer)

λ N mutant:
(SEQ ID NO: 47)
GNARTRRRERRAEKQAQWKAAN (22 mer)

P22 N:
(SEQ ID NO: 48)
NAKTRRHERRRKLAIER (17 mer)

φ21N:
(SEQ ID NO: 49)
TAKTRYKARRAELIAERR (18 mer)

BMV Gag:
(SEQ ID NO: 50)
KMTRAQRRAAARRNRWTAR (19 mer)

CCMV Gag:
(SEQ ID NO: 51)
KLTRAQRRAAARKNKRNTR (19 mer)

Spuma Gag:
(SEQ ID NO: 52)
TRALRRQLAER (11 mer)

Yeast PRP6:
(SEQ ID NO: 53)
TRRNKRNRIQEQLNRK (16 mer)

Human U2AF:
(SEQ ID NO: 54)
SQMTRQARRLYV (12 mer)

-continued

```
HTLV-II Rex:
                                              (SEQ ID NO: 55)
TRRQRTRRARRNR (13 mer)

FHV coat:
                                              (SEQ ID NO: 56)
RRRRNRTRRNRRRVR (15 mer)

S3:
                                              (SEQ ID NO: 57)
RRVAFRRIVRKAITRAQRR (19 mer)

S7:
                                              (SEQ ID NO: 58)
KTKLERRNK (9 mer)

S28:
                                              (SEQ ID NO: 59)
RKLRVHRRNNR (11 mer)

L16:
                                              (SEQ ID NO: 60)
RRAMSRKFRRNSK (13 mer)

L35:
                                              (SEQ ID NO: 61)
RAKKTRALRR (10 mer)

Of these, HIV-1 Tat binds to HIV-1 TAR
(5'-CCAGAUCUGAGCCUGGGAGCUCUCUGG-3': SEQ ID NO: 62)
and JDV Tat binds to JDV TAR
(5'-GCUCUGGAUAGCUGACAGCUCCGAGC-3': SEQ ID NO: 63).
```

The sequence to which nucleic acid binding polypeptide is not particularly restricted as long as it is a sequence to which the polypeptide described above is able to bind. A sequence forming a stem loop is preferred, and a sequence forming a stem loop whose loop length is 3 to 10 bases, preferably 3 to 8 bases, and more preferably 3 to 7 bases is desired.

In addition to the sequence illustrated above as an example, examples thereof include a sequence as shown below.

```
P22 boxB:
                                              (SEQ ID NO: 64)
    5'-GCGCUGACAAAGCGC-3' (15 mer)

HIV-1 RRE:
                                              (SEQ ID NO: 65)
    5'-GGUCUGGGCGCAGCGCAAGCUGACGGUACAGGCC-3'
    (34 mer)
```

It is to be noted that, as long as the nucleic acid binding polypeptide is able to bind to the above, one to several (for example, two or three) bases may be substituted, deleted, or added in these sequences.

In the coding region, the order of a first nucleic acid binding polypeptide coding sequence and a second nucleic acid binding polypeptide coding sequence depends on the order of the first sequence and the second sequence in the 5'-untranslated region. If the first sequence (for example boxB sequence) precedes (in the 5' side) in the 5'-untranslated region, the first nucleic acid binding polypeptide coding sequence (for example Bap-coding sequence) is arranged to precede (in the 5' side) in the coding region, whereas if the second sequence (for example Cv sequence) is precedes (in the 5' side), the second nucleic acid binding polypeptide coding sequence (for example Cvap dimer-coding sequence) is arranged to precede (the 5' side) in the coding region.

A gap of the first nucleic acid binding polypeptide coding sequence and the second nucleic acid binding polypeptide coding sequence is preferably 60 to 75 bases from the aspect of stabilization of the protein-RNA complex.

In the coding region, the sequence coding for a polypeptide subjected to be displayed is arranged to precede (the 5' side) the first nucleic acid binding polypeptide coding sequence and the second nucleic acid binding polypeptide coding sequence and these are preferably arranged in frame.

Here, the sequence coding for a polypeptide subjected to be displayed may be a known sequence or may be a random sequence. In addition, the length thereof is not particularly restricted, and it may be a short peptide or may be a short protein.

The type of polypeptide to be displayed having a known sequence is not particularly restricted, and examples thereof include enzymes, antibodies, signal transduction factors, channels, cell growth factors, transcription factors, adhesion factors, and receptors. Note that it may be a protein with an unknown function.

An origin thereof is not particularly restricted. A polypeptide having a naturally-occurring sequence derived from any organisms such as mammals including human, plants, viruses, yeasts, or bacteria can be used. Alternatively, a part of the above-mentioned naturally-occurring polypeptide or a mutant peptide obtained by modifying the amino acid sequence can be used as the polypeptide subjected to be displayed. Further, a polypeptide containing an artificially designed amino acid sequence can also be sued as the polypeptide subjected to be displayed.

In the case of making a polypeptide coding sequence have a random sequence, it is preferred to be a sequence coding for a random polypeptide in which any amino acids are randomly arranged. The random polypeptide usually has a random amino acid sequence of a length of approximately 5 to 100 residues, preferably 5 to 50 residues, more preferably 5 to 20 residues. The amino acids may be naturally-occurring ones, may be non-naturally occurring ones, or may be a mixture thereof. More simply and conveniently, the random polypeptide is composed of one or more kinds of amino acids selected from naturally-occurring 20 amino acids.

In the case of making the polypeptide have a completely random sequence (the number of the amino acid residues is n), 3n of A, T, G, and C need only to be randomly arranged. It is to be noted that, in order for a clone to be efficiently translated, a base at the 3m th position (m=1, 2, 3 . . . , n) may set to be T or C such that appearance of a stop codon can be avoided. Alternatively, codons may be adjusted such that the sequence is a random sequence composed of two or more certain kinds of amino acids alone.

Use of repeat of an NRY codon allows a peptide sequence in which eight kinds of amino acids (Ser, Asn, Gly, Asp, Arg, His, Cys or Tyr) randomly appear to be expressed.

N=A, G, C, T
R=A, G
Y=C, T

Note that, in cases where the random polypeptide contains non-naturally occurring amino acids, the codon may be modified according to a known means.

In the coding region, the sequences coding for the polypeptide subjected to be displayed, the first nucleic acid binding polypeptide coding sequence, the second nucleic acid binding polypeptide coding sequence are linked in flame. The term "linked in flame" herein means that the polypeptide subjected to be displayed, the first nucleic acid binding polypeptide coding sequence, and the second nucleic acid binding polypeptide coding sequence are linked so as to be translated as a fusion protein. Note that the polypeptide subjected to be displayed, the first nucleic acid binding polypeptide coding sequence, and the second nucleic acid binding polypeptide coding sequence may be linked directly but are preferably linked via a linker coding sequence for the purpose of securing the degrees of freedom of the polypeptide subjected to be displayed.

The sequence coding for a polypeptide subjected to be displayed such as the random polypeptide can be artificially synthesized and linked to, for example, the 5' side of Bap-coding sequence and Cvap dimer-coding sequence using a restriction enzyme recognition sequence (SfiI recognition sequence is used in the example) or using PCR by a genetic engineering process. It is to be noted that the whole of the sequence coding for a polypeptide subjected to be displayed, the first nucleic acid binding polypeptide coding sequence, and the second nucleic acid binding polypeptide coding sequence may be artificially synthesized.

A start codon, ATG is preferably present in the 5' side of the sequence coding for a polypeptide subjected to be displayed; and a tag peptide (for example, FLAG, poly histidine, GST, or the like) may be disposed following the start codon and then the sequence coding for a polypeptide subjected to be displayed may be disposed to follow.

Further, it is preferred to dispose a spacer-coding sequence in the downstream (the 3' side) of the first nucleic acid binding polypeptide coding sequence and the second nucleic acid binding polypeptide coding sequence from the aspect of stability of the polypeptide (fusion protein)-ribosome-RNA complex.

The spacer sequence is preferably set to be a sequence of 10 to 200 amino acids. The amino acid sequence of the spacer sequence is not particularly restricted as long as it does not adversely affect a binding reaction between a protein subjected to be displayed and a target substance. It is preferably a sequence that is highly water-soluble and does not take a particular kind of three-dimensional structure. To be specific, a so-called GS linker that mainly contains glycine and serine or a partial sequence of gene III of phage can be used.

A stop codon may be placed in the 3' end of the coding region; however it is preferred not to place on the stop codon in the 3' end of the coding region for the purpose of efficiently seizing the ribosome. Alternatively, SecM sequence may be added to the 3' end of the coding region. The SecM sequence is also referred to as the SecM stall sequence and a sequence that is reported to cause translation arrest inside the ribosome (FXXXXWIXXXXGIRAGP: SEQ ID NO: 32). Introduction of the arrest sequence of SecM allows a polypeptide (fusion protein)-ribosome-RNA complex to be efficiently maintained, and thus the sequence is particularly beneficial for a ribosome display.

FIG. 1 (2) depicts a schematic diagram of one example of polypeptide (fusion protein)-ribosome-RNA complex obtained by introducing the nucleic acid construct of the present invention into a translation system. Although one referred to as "Peptide/protein libraries" is a polypeptide subjected to be displayed, it does not necessarily to be a library. In the conventional polypeptide-ribosome-RNA complex, the ribosome is, as shown in FIG. 1 (1), merely seized on the RNA to maintain the complex. In contrast, in the case of FIG. 1 (2), the complex is stabilized by interactions of Bap and boxB; and the Cvap dimer and Cv.

The nucleic acid construct of the present invention may be DNA or may be RNA (preferably mRNA). Thus, "RNA corresponding to a nucleic acid construct" means, in cases where the nucleic acid construct is RNA, the nucleic acid construct itself; and, in the case of DNA, RNA obtained by being transcribed from the nucleic acid construct.

In the case of DNA, it is preferred to add a promoter sequence for transcribing RNA in the upstream of the 5'untranslated region.

A promoter can be selected as appropriate according to an expression system to be used. For instance, in the case of using *Escherichia coli* cells or a cell free translation system of *Escherichia coli* origin, examples of the promoter include a T7 promoter, a T3 promoter, and an SP6 promoter, all of which promoters function in *Escherichia coli*.

As one example of the present invention, SEQ ID NOs: 5, 9, 11, 13, and 15 illustrates the nucleic acid construct containing promoter sequence, boxB sequence, Cv sequence, SD sequence, start codon, sequence coding for a polypeptide subjected to be displayed, Bap-coding sequence, Cvap dimer-coding sequence, and spacer coding sequence (FIG. 2).

And, SEQ ID NOs: 6, 10, 12, 14, and 16 show the amino acid sequences of the fusion proteins translated from these nucleic acids. It is to be noted that the nucleic acid construct of the present invention and a fusion protein encoded thereby are not limited these.

The nucleic acid construct of the present invention may be incorporated into a plasmid vector, a phage vector, or a viral vector. The type of vector can be selected as appropriate according to a translation system or a screening system to be employed.

The above nucleic acid construct and the vector containing the construct can be prepared by known genetic techniques described in Molecular Cloning (Cold Spring Harbor Laboratory Press, Cold Spring Harbor (USA), 2001) or the like.

<Method of Displaying Polypeptide on Nucleic Acid (RNA) Using the Nucleic Acid Construct of the Present Invention>

By introducing the above nucleic acid construct in a translation system to express a fusion protein encoded by the above-mentioned coding region, a complex of the fusion protein and RNA corresponding to the nucleic acid construct can be formed through a bond between the first nucleic acid binding polypeptide and the first sequence; and a bond of the second nucleic acid binding polypeptide and the second sequence; and the polypeptide subjected to be displayed can be displayed on the RNA.

As the translation system, a cell free translation system containing the ribosome obtained from cells derived from *Escherichia coli*, insects, wheat germs, rabbit reticulocytes, human cancers, or the like can be used. It may also be a cell free translation system to which ribosomes, tRNAs, amino acids, or the like are added to reconstruct. It may also be one that is commercially available.

Note that, in cases where DNA is used as the nucleic acid construct, RNA polymerase appropriate to a promoter shall be added.

In cases where a random peptide library is used as the protein subjected to be displayed, the size of the library is usually $1\times10^3$ or more, preferably $1\times10^4$ or more, more preferably $1\times10^5$ or more, and still more preferably $1\times10^6$ or more.

Note that the ribosome may be dissociated from RNA after the formation of the polypeptide-ribosome-RNA complex. In this instance, EDTA (or ligand capable of chelating $Mg^{2+}$ ion such as EGTA) with a concentration of 50 to 650 mM needs only to be added to the translation system. EDTA may be added to the translation system from the beginning.

By dissociating the ribosome from RNA, the polypeptide-RNA complex that does not contain the ribosome can be obtained.

<Method of Selecting Polypeptide Sequence that Binds to Target Substance Using the Nucleic Acid Construct of the Present Invention>

In the method of selecting a polypeptide sequence of the present invention, the steps (1) to (3) are repeated:

(1) the step of expressing a fusion protein of a random polypeptide, the first nucleic acid binding polypeptide, and the second nucleic acid binding polypeptide from the nucleic acid construct of the present invention to display a random polypeptide library on RNA corresponding to the nucleic acid construct;

(2) the step of bringing the above-mentioned library into contact with a target substance; and (3) the step of selecting a fusion protein containing a polypeptide sequence that binds to the target substance and amplifying a nucleic acid sequence coding for the selected fusion protein.

To be specific, the nucleic acid construct of the present invention is introduced into a translation system to form a polypeptide-RNA complex. Thereafter, a random polypeptide library was brought into contact with a target substance, and a fusion protein containing a polypeptide sequence that binds to the target substance is selected from random polypeptide library. The nucleic acid construct coding therefor is amplified.

To select a polypeptide that bonds to a target substance, the polypeptide that binds with the target polypeptide need to be screened from among a number of polypeptides that do not bind with the target polypeptide. This carried out according to a known method called panning (Coomber (2002) Method Mol. Biol., vol. 178, p. 133-145). A basic protocol of the panning is as follows:

(I) Contact a polypeptide library with a target substance.

(II) Remove other polypeptides that are contained in the library and do not bind to the target polypeptide. For instance, the removal can be done by washing.

(III) Collect a polypeptide that is not removed, that is, a polypeptide that specifically binds to the target polypeptide.

(IV) Repeat, as needed, the procedures (I) to (III) more than once.

Note that, it is preferred that the ribosome be dissociated from the polypeptide-RNA complex after the step (1) using EDTA or the like, because "steric hindrance between the ribosome of the complex and the target molecule" and non-specific binding can be resolved.

Conditions under which the polypeptide library is brought into contact with the target substance to enable the binding are known (WO95/11922, WO93/03172, and WO91/05058), and can be established without excessive burden for those skilled in the art. For instance, the target substance may be bound to a carrier such as a bead, plate, or column; and a sample containing the complex of the polypeptide and RNA may be brought into contact therewith. Further, in cases where the target substance is a metal (including a metal salt and metal oxide) or a silicon-containing compound, addition of these substances to a sample containing the complex of the polypeptide and RNA allows the contact.

RNA contained in the selected complex can be amplified by, for example, RT-PCR. By RT-PCR, DNA is synthesized using RNA as a template. DNA is again transcribed into RNA, which can be used for formation of the complex.

By repeating the above procedures, a peptide sequence that specifically binds to the target substance is concentrated. Sequence information can be identified by analyzing the sequence of the obtained RNA.

EXAMPLES

By way of examples the present invention will now be specifically described below. However, the present invention is by no means limited to the following modes.

Example 1

Novel Development of "Stable Cross-Linking Type Ribosome Display Method" Using Template Introduced with Peptide and Protein that Specifically Bind to RNA Motif Here, as development of a stable cross-linking type ribosome display method, two RNA motifs (boxB and Cv) were introduced into the 5' end of a mRNA template used for translating a peptide library. Further, sequences coding for a peptide (Bap) and protein (Cvap dimer) that specifically bind to each RNA motif were introduced into the downstream of a sequence for coding the peptide library. In this way, the peptide (Bap) and protein (Cvap dimer) expressed by in vitro translation of the mRNA template form a cross-linked structure with each of the RNA motifs with affinities and therefore a "peptide-Bap-Cvap-ribosome-mRNA complex (FIG. 1 (2))" that is acquiring unprecedented stability can be synthesized.

First of all, in order to prove that the use of "peptide-Bap-Cvap-ribosome-mRNA complex" makes it possible to select a target molecule binding peptide, a "FLAG peptide selection experiment" was carried out with an anti-FLAG antibody immobilized to beads as a target. (This experiment was carried out in accordance with the operation scheme of FIG. 3 as a model experiment of selecting a target molecule binding peptide from within the complex displaying the peptide library.)

First, construction of plasmid DNA-I (SEQ ID NO: 1: FIG. 4) and plasmid DNA-II (SEQ ID NO: 2: FIG. 4) for synthesizing a "peptide-Bap-Cvap-ribosome-mRNA complex" was carried out. The plasmid DNA-I was constructed by introducing an artificial sequence in which SD sequence•start codon•SfiI restriction enzyme site (1)•SfiI restriction enzyme site (2)•Bap sequence•Cvap sequence•Ps sequence are lined up in the order mentioned into the cloning site of a commercially available plasmid. Further, the plasmid DNA-II was constructed by introducing an artificial sequence in which T7 promoter sequence•SD sequence•start codon•SfiI restriction enzyme site (1)•SfiI restriction enzyme site (2)•Bap sequence•Cvap sequence•Ps sequence are lined up in the order mentioned into the cloning site of a commercially available plasmid.

Next, a FLAG peptide was introduced into an SfiI site of the plasmid DNA-II to construct plasmid DNA-II-FLAG (SEQ ID NO: 8, a partial sequence thereof is SEQ ID NO: 5). With it as a template, DNA template 4-NS (FIG. 4: NS indicates no stop codons are present) was synthesized by PCR using primer fp4 (SEQ ID NO: 28) and rp3 (SEQ ID NO: 31).

And then, a mRNA template was synthesized from a T7 promoter using the DNA template 4-NS. This was subjected to a translation reaction of a cell-free protein synthesis system (manufactured by BioComber Co., Ltd., PURESYSTEM classic II), thereby synthesizing a "FLAG peptide-Bap-Cvap-ribosome-mRNA complex".

Further, according to procedure 1 of the following peptide selection experiment, the complexes and beads immobilized with an anti-FLAG antibody (manufactured by SIGMA-ALDRICH) were mixed and then only complexes that specifically bound with the anti-FLAG antibody were competitively eluted from the bead by addition of the antibody FLAG peptide (manufactured by SIGMA-ALDRICH). And then, mRNA collected from those complexes was subjected to reverse transcription to obtain cDNA. With the cDNA as a template, PCR was carried out and the PCR product was subjected to electrophoresis.

As a result, it was able to be confirmed that the mRNA coding for the intended FLAG peptide was successfully collected (FIGS. 1-(3)). In this way, it was shown that the peptide selection experiment is feasible by the "stable cross-linking type ribosome display method" utilizing the "peptide-Bap-Cvap-ribosome-mRNA complex".

<Procedure 1 of Peptide Selection Experiment>

1. Mix a selection buffer (250 μl) and a translation solution (50 μl) having a "peptide-Bap-Cvap-ribosome-mRNA complex". Add beads (15 μl) thereto and then incubate (1 h, 4° C.).
2. Wash the beads treated in 1 with a washing buffer (300 μl) five times.
3. Add a FLAG peptide (100 μl) to the beads treated in 2 and further incubated (0.5 h, 4° C.).
4. Precipitate the beads at 1000 rpm (5 min) and then collect the supernatant (100 μl).
5. Purify mRNA collected in 4 (manufactured by QIAGEN, RNeasy kit). Using it, carry out reverse transcription (manufactured by TAKARA, PrimeScript Reverse Transcriptase) to synthesize cDNA.
6. Carry out PCR (manufactured by TAKARA, PrimeSTAR GXL DNA Polymerase) with the cDNA synthesized in 5 as a template. Subject the PCR product to electrophoresis to check the amount of mRNA collected.

Washing buffer: Tris-HCl (50 mM, pH 7.5), NaCl (150 mM), 0.5% Tween
Selection buffer: Tris-HCl (60 mM, pH 7.5), NaCl (180 mM)
Beads: ANTI-FLAG-M2-Affinity Gel (manufactured by SIGMA-ALDRICH)
FLAG peptide (manufactured by SIGMA-ALDRICH)

Example 2: Development of "Stable Cross-Linking Type Display Method" Utilizing Complex with Ribosome being Dissociated Conventionally, "steric hindrance between the ribosome of a complex and a target molecule" has been a problem in a ribosome display method. If this problem can be resolved, it becomes possible to create a stronger target binding peptide that has not been able to be selected thus far.

In view of this, efforts were this time put into synthesizing a "peptide-mRNA complex" having the ribosome by a simple method that was completely different from a mRNA display method and developing a novel display method using those.

Here, attention was focused on a phenomenon that the above "peptide-Bap-Cvap-ribosome-mRNA complex" developed in Example 1 was stabilized by formation of an intramolecular cross-linked structure and it was attempted to solely dissociate the ribosome from that complex to synthesize a "peptide-Bap-Cvap-mRNA complex" (FIG. 2 (D)). Further, it was decided to demonstrate, by performing and evaluating a peptide selection experiment in which the "peptide-Bap-Cvap-mRNA complex" was use, that this novel "stable cross-linking type display method" was useful.

First, in order to check if an artificial protein for forming four kinds of complexes shown in FIG. 2 can be equivalently expressed from mRNA with an RNA motif being introduced in the 5' end thereof and mRNA with RNA motif not being introduced, an experiment was carried out by the following procedure.

A FLAG peptide (peptide library model) was introduced into the SfiI site of plasmid DNA-I (SEQ ID NO: 1) and DNA-II (SEQ ID NO: 2) to construct plasmid DNA-I-FLAG (SEQ ID NO: 7, a partial sequence is SEQ ID NO: 3) and DNA-II-FLAG (SEQ ID NO: 8, a partial sequence is SEQ ID NO: 5). And, the following 4 kinds of DNAs were constructed.

(A) With the plasmid DNA-I-FLAG as a template, using fp1 (SEQ ID NO: 25) and rp1 (SEQ ID NO: 29) as primers, DNA template 1-S (SEQ ID NO: 9) was amplified by PCR.

(B) With the plasmid DNA-I-FLAG as a template, using fp2 (SEQ ID NO: 26) and rp1 (SEQ ID NO: 29) as primers, DNA template 2-S (SEQ ID NO: 11) was amplified by PCR.

(C) With the plasmid DNA-I-FLAG as a template, using fp3 (SEQ ID NO: 27) and rp1 (SEQ ID NO: 29) as primers, DNA template 3-S (SEQ ID NO: 13) was amplified by PCR.

(D) With the plasmid DNA-II-FLAG as a template, using fp4 (SEQ ID NO: 28) and rp1 (SEQ ID NO: 29) as primers, DNA template 4-S (SEQ ID NO: 15) was amplified by PCR.

The primer fp1 contains a sequence of the base numbers 1 to 24 of SEQ ID NO: 3 and contains a T7 promoter.

The primer fp2 contains a sequence of the base numbers 1 to 24 of SEQ ID NO: 3 and contains a T7 promoter and boxB sequence.

The primer fp3 contains a sequence of the base numbers 1 to 24 of SEQ ID NO: 3 and contains a T7 promoter and Cv sequence.

The primer fp4 contains a sequence of the base numbers 1 to 35 of SEQ ID NO: 5 and contains a T7 promoter, boxB sequence, and Cv sequence.

The primer rp1 contains a sequence complementary to the base numbers 1094 to 1113 of SEQ ID NO: 3 and the base numbers 1157 to 1176 of SEQ ID NO: 5 and contains a stop codon.

Further, each of the mRNA template was synthesized in vitro transcription using a T7 promoter from those DNA templates. The mRNA was translated by a cell-free protein synthesis system (manufactured by BioComber Co., Ltd., PURESYSTEM classic II), thereby expressing a "FLAG peptide-Bap-Cvap fusion protein" (SEQ ID NO: 10, 12, 14, or 16).

As a result, it was able to be confirmed in Western blotting (FIG. 5) using an anti-FLAG antibody-HRP (manufactured by SIGMA-ALDRICH) and a chemiluminescence reagent (manufactured by PIERCE) that, regardless of the presence or absence of the RNA motif introduced in the 5' end of the mRNA, a comparable amount of proteins was expressed.

Next, in order to carried out the FLAG peptide selection experiment in which 4 kinds of complexes shown in FIG. 2 were used, the following 4 kinds of DNAs were constructed (FIGS. 4-1 to 4).

(A) With plasmid DNA-I-FLAG as a template, using fp1 (SEQ ID NO: 25) and rp3 (SEQ ID NO: 31) as primers, DNA template 1-NS (a sequence with 1177 to 1626 of SEQ ID NO: 5, in place of taatga, being added to the end of SEQ ID NO: 9) was amplified by PCR.

(B) With plasmid DNA-I-FLAG as a template, using fp2 (SEQ ID NO: 26) and rp3 (SEQ ID NO: 31) as primers, DNA template 2-NS (a sequence in which 1177 to 1626 of SEQ ID NO: 5, in place of taatga, was added to the end of SEQ ID NO: 11) was amplified by PCR.

(C) With plasmid DNA-I-FLAG as a template, using fp3 (SEQ ID NO: 27) and rp3 (SEQ ID NO: 31) as primers, DNA template 3-NS (a sequence in which 1177 to 1626 of SEQ ID NO: 5, in place of taatga, was added to the end of SEQ ID NO: 13) was amplified by PCR.

(D) With plasmid DNA-II-FLAG as a template, using fp4 (SEQ ID NO: 28) and rp3 (SEQ ID NO: 31) as primers, DNA template 4-NS (a sequence in which 1177 to 1626 of SEQ ID NO: 5, in place of taatga, was added to the end of SEQ ID NO: 15) was amplified by PCR.

The primer rp3 contains a sequence complementary to the base numbers 1544 to 1563 of SEQ ID NO: 3 and the base numbers 1607 to 1626 of SEQ ID NO: 5 and does not contain a stop codon.

Further, each of the mRNA templates that was synthesized by in vitro transcription using the T7 promoter of those DNA templates was translated by a cell-free protein synthesis system (manufactured by BioComber Co., Ltd., PURE-SYSTEM classic II). And, according to procedure 2 of the following peptide selection experiment, a buffer containing EDTA (50 mM) and translation solution are mixed to dissociate the ribosome from the mRNA, thereby obtaining 4 kinds of complexes shown in FIG. 2.

Subsequently, those complexes and beads immobilized with an anti-FLAG antibody (manufactured by SIGMA-ALDRICH) were mixed and then only complexes that specifically bound with the anti-FLAG antibody were competitively eluted from the bead by addition of the antibody FLAG peptide (manufactured by SIGMA-ALDRICH). And, PCR was carried out using cDNA obtained by subjecting the collected mRNA to reverse transcription as a template. The PCR product obtained from each of experiments to electrophoresis to compare the amount of mRNA collected.

As a result, in electrophoresis of FIG. 6 (A) (18 cycles), only when the "peptide-Bap-Cvap-mRNA complex" was used, the band was able to be confirmed. In the electrophoresis this time (FIG. 6), the band was able to be confirmed in a condition of less number of cycles in PCR when a more amount of mRNA of FLAG peptide was collected from each of the complexes. Therefore, it became clear that the "peptide-Bap-Cvap-mRNA complex" of FIG. 2 (D) was most stable and, at the same time, the use of this complex made it possible to carry out the same peptide selection experiment as described in the "stable cross-linking type ribosome display (FIGS. 1-(3))". Further, in electrophoresis of FIG. 6 (B) (21 cycles), also when the complex of FIG. 2 (B) and the complex of FIG. 2 (C) were used, the band was able to be confirmed. Therefore, it was demonstrated that the use of these also made it possible to carry out the peptide selection experiment.

<Procedure 2 of Peptide Selection Experiment>

1. Mix a selection buffer (250 μl) and a translation solution (50 μl) having each of the complexes. Add beads (15 μl) thereto and then incubate (1 h, 4° C.).
2. Wash the beads treated in 1 with a washing buffer (300 μl) five times.
3. Add a FLAG peptide (100 μl) to the beads treated in 2 and further incubated (0.5 h, 4° C.).
4. Precipitate the beads at 1000 rpm (5 min) and then collect the supernatant (100 μl).
5. Purify mRNA collected in 4 (manufactured by QIAGEN, RNeasy kit). Using it, carry out reverse transcription (manufactured by TAKARA, PrimeScript Reverse Transcriptase) to synthesize cDNA.
6. Carry out PCR (manufactured by TAKARA, PrimeSTAR GXL DNA Polymerase) with the cDNA synthesized in 5 as a template. Subject the PCR product to electrophoresis to check the amount of mRNA collected.

Washing buffer: Tris-HCl (50 mM, pH 7.5), NaCl (150 mM), EDTA (50 mM), 0.5% Tween Selection buffer: Tris-HCl (60 mM, pH 7.5), NaCl (180 mM), EDTA (60 mM)

Beads: ANTI-FLAG-M2-Affinity Gel (manufactured by SIGMA-ALDRICH)

FLAG peptide (manufactured by SIGMA-ALDRICH)

Example 3: Display of Various Polypeptides•Proteins in "Stable Cross-Linking Type Ribosome Display Method" and "Stable Cross-Linking Type Display Method"

From the above experiment, it became clear that the selection experiment of the peptide that specifically bound to the target molecule was able to be carried out utilizing the "stable cross-linking type ribosome display method" and "stable cross-linking type display method".

Further, in order to establish as a versatile display method capable of selecting a peptide (protein) aptamer that exerts an intended function by introducing a peptide (protein) library having various lengths into plasmid DNA-II, various polypeptides-proteins were introduced into the plasmid DNA-II to test whether or not those were expressed.

First, A polyhistidine tag (H6)(SEQ ID NO: 66), Human epidermal growth factor (EGF), FK-binding protein 12 (FKBP12), and Cyclophilin A (CypA) were introduced into an SfiI site of plasmid DNA-II (SEQ ID NO: 2) to construct various plasmids. namely DNA-II-H6 (SEQ ID NO: 17) ("H6" disclosed as SEQ ID NO: 66). DNA-II-EGF (SEQ ID NO: 19), DNA-II-FKBP12 (SEQ ID NO: 21), and DNA-II-CypA (SEQ ID NO: 23).

And then, by PCR with those plasmid DNAs as templates and using primers fp4 (SEQ ID NO: 28) and rp2 (SEQ ID NO: 30). DNA templates 5-H6-FLAG-S "H6" disclosed as SE ID NO: 66), 5-EGF-FLAG-S, 5-FKBP12-FLAG-S, and 5-CypA-FLAG-S were synthesized (FIG. 4; X represents H6 ("H6" disclosed as SEQ ID NO: 66), EGF, FKBP12 or CypA in 5-X)

The primer rp2 contains a sequence complementary to base numbers 1157 to 1176 of SEQ ID NO: 5 and contains a FLAG coding sequence and stop codon.

Further, a mRNA template that was synthesized by in vitro transcription using a T7 promoter from those DNA templates was translated by a cell-free protein synthesis system (manufactured by BioComber Co., Ltd., PURESYSTEM classic II) to express various proteins (SEQ ID NOs: 18, 20, 22, and 24). And, Upon carrying out Western blotting (FIG. 7) using an anti-FLAG antibody-HRP (manufactured by SIGMA-ALDRICH) and a chemiluminescence reagent (manufactured by PIERCE), expression of each of the proteins was successfully confirmed.

This result is implying that, by using the plasmid DNA-II, the "peptide (protein)-Bap-Cvap-mRNA complex" in which various peptide (protein) libraries are introduced can be synthesized and the selection experiment of the intended peptide (protein) aptamer can be carried out.

Example 4: New Creative Construction of RNA Motif-Peptide Cross-Linked Structure In order to explore possibilities of diversifying the stably cross-linked ribosomal complex and making it compact and, at the same time, to figure out potentials of the RNA motif-peptide cross-linked structure for versatile use (example: delivery of functional nucleic acid•nucleic acid medicine or the like), efforts were put into new creative construction of RNA motif-peptide cross-linked structure (FIG. 8). Here, with an RNA motif-peptide interaction that naturally occurs and an RNA motif-peptide interaction that artificially found as models, heterogeneous tandemly disposed RNA motifs and tandemly disposed peptides that bind to the motifs were newly designed (FIG. 8 and Table 1). And, various RNA motifs synthesized by a chemical technique and the peptide were mixed, and thereafter whether or not the RNA motif-peptide cross-linked structure could be formed was evaluated by a gel shift assay by electrophoresis (the experiment this time was performed according to the following condition and procedure).

For instance, when a tandemly disposed RNA motif (TRM4: Table 1) and tandemly disposed peptide (TP3 or TP4: Table 1) were mixed, the band shift indicating the formation of the RNA motif-peptide cross-linked structure was able to be confirmed (FIG. 9: arrow). Further, formation of the cross-linked structure of all of the tandemly disposed RNA motifs shown in Table 1 and the tandemly disposed peptide corresponding to each thereof was also able to be confirmed by electrophoresis. These results are implying not only that the tandemly disposed peptides synthesized this time are able to quantitatively form the RNA motif-peptide cross-linked structure but also that the peptides can be used in synthesis of a stable type ribosomal complex that is easier to handle owing to the smaller molecular weight (about ⅙) than that of the fusion protein composed of the peptide (Bap) and protein (Cvap) of Examples 1 to 3. Further, application to delivery of functional nucleic acid-nucleic acid medicine such as siRNA or ncRNA using these RNA motif-peptide cross-linked structures is also promising.

<Preparation of RNA Motif-Peptide Mixture Solution and Electrophoresis>

(1) Prepare an RNA motif solution (1 µM) by the following sample buffer. And, Incubate the solution at 70° C. and then leave to stand at room temperature.

(2) Mix various peptide solutions (1 µM) prepared by the following sample buffer and the above RNA motif solution and then balance to a total amount of 10 µL (final molar amount of RNA: 4 pmol).

(3) Separate the RNA motif and RNA motif-peptide cross-linked structure by 10% PAGE and then stain the gel with SYBRG to measure the image (example: FIG. 9).

Sample buffer: Tris-acetate (50 mM, pH7.5), KCl (150 mM), Tween-20 (0.1%), Mg(AcO)$_2$ (50 mM), Zn(AcO)$_2$ (0.1 mM)

Electrophoresis buffer: Tris-acetate (10 mM, pH 7.5)

TABLE 1

| New design of peptides and RNA motifs |
|---|
| Tandemly disposed RNA peptide: TP |
| TP1:P1 = Bap, P2 = Rev, sp = GS2 |
| TP2:P1 = Bap, P2 = Rev, sp = GS3 |
| TP3:P1 = Rev, P2 = Bap, sp = GS2 |
| TP4:P1 = Rev, P2 = Bap, sp = GS3 |
| TP5:P1 = BIV Tat, P2 = Bap, sp = GS2 |
| TP6:P1 = BIV Tat, P2 = Bap, sp = GS3 |
| Tandemly disposed RNA motif: TRM |
| TRM1:R1 = boxB, R2 = ap I, n = 8 |
| TRM2:R1 = boxB, R2 = ap II, n = 8 |
| TRM3:R1 = ap I, R2 = boxB, n = 8 |

TABLE 1-continued

| New design of peptides and RNA motifs |
|---|
| TRM4:R1 = ap II, R2 = boxB, n = 8 |
| TRM5:R1 = BIV TAR, R2 = boxB, n = 8 |

<Sequence of Peptide>

Bap:
(SEQ ID NO: 33)
GNARTRRRERRAMERATLPQVLG

Rev:
(SEQ ID NO: 34)
TRQARRNRRRRWRERQR

BIV Tat:
(SEQ ID NO: 35)
SGPRPRGTRGKGRRIRR

GS2:
(SEQ ID NO: 36)
GGGSGGGS

GS3:
(SEQ ID NO: 37)
GGGSGGGSGGGS

<Sequence of RNA Motif> boxB:
(SEQ ID NO: 38)
GGCCCUGAAAAAGGGCC ap I:
(SEQ ID NO: 39)
GGCUGGACUCGUACUUCGGUACUGGAGAAACAGCC ap II:
(SEQ ID NO: 40)
GGUGUCUUGGAGUGCUGAUCGGACACC

BIV TAR:
(SEQ ID NO: 41)
GCUCGUGUAGCUCAUUAGCUCCGAGC

INDUSTRIAL APPLICABILITY

The nucleic acid construct of the present invention and the method using it is useful in the field of genetic engineering, peptide engineering, drug development, or the like.

DESCRIPTION OF SEQUENCE LISTING

1. Plasmid DNA-I full base sequence
2. Plasmid DNA-II full base sequence
3. Plasmid DNA-I-FLAG partial base sequence
4. Amino acid sequence of 3
5. Plasmid DNA-II-FLAG partial base sequence
6. Amino acid sequence of 5
7. Plasmid DNA-I-FLAG full base sequence
8. Plasmid DNA-II-FLAG full base sequence
9. DNA-I-fp1-rp1 base sequence
10. Amino acid sequence of 9
11. DNA-I-fp2-rp1 base sequence
12. Amino acid sequence of 11
13. DNA-I-fp3-rp1 base sequence
14. Amino acid sequence of 13
15. DNA-I-fp4-rp1 base sequence
16. Amino acid sequence of 15
17. Plasmid DNA-II-H6 full base sequence ("H6" disclosed as SEQ ID NO: 66)

18. Amino acid sequence of 17
19. Plasmid DNA-II-EGF full base sequence
20. Amino acid sequence of 19
21. Plasmid DNA-II-FKBP12 full base sequence
22. Amino acid sequence of 21
23. Plasmid DNA-II-CypA full base sequence
24. Amino acid sequence of 23
25. Primer fp1 base sequence
26. Primer fp2 base sequence
27. Primer fp3 base sequence
28. Primer fp4 base sequence
29. Primer rp1 base sequence
30. Primer rp2 base sequence
31. Primer rp3 base sequence
32. secM amino acid sequence
33. Bap
34. Rev
35. BIV Tat
36. Linker 1
37. Linker 2
38. boxB
39. apI
40. apII
41. BIV TAR
42. Consensus sequence 1
43. Consensus sequence 2
44. HIV-1 Tat
45. JDV Tat
46. λN
47. λN mutant
48. P22N
49. φ21N
50. BMV Gag
51. CCMV Gag
52. Spuma Gag
53. Yeast PRP6
54. Human U2AF
55. HTLV-II Rex
56. FHV coat
57. S3
58. S7
59. S28
60. L16
61. L35
62. HIV-1 TAR
63. JDV TAR
64. P22 boxB
65. HIV-1 RRE

The invention claimed is:

1. A nucleic acid construct comprising a 5'-untranslated region and a coding region, wherein said coding region comprises a sequence coding for a polypeptide subjected to be displayed, a sequence coding for a first nucleic acid binding polypeptide, and a sequence coding for a second nucleic acid binding polypeptide; said 5'-untranslated region comprises a first sequence capable of binding to the first nucleic acid binding polypeptide and a second sequence capable of binding to the second nucleic acid binding polypeptide, wherein said second sequence is independent from said first sequence;

wherein (i) said first nucleic acid binding polypeptide and said second nucleic acid binding polypeptide are a boxB-associating peptide (Bap) and a Cv-associating peptide (Cvap) dimer; and said first sequence and said second sequence are a boxB sequence and a Cv sequence, (ii) said first nucleic acid binding polypeptide and said second nucleic acid binding polypeptide are Bap and a binding domain to an aptamer I (apI) sequence or an aptamer II (apII) sequence of regulator of viral expression (Rev); and said first sequence and said second sequence are a boxB sequence and an apI sequence or an apII sequence, or (iii) said first nucleic acid binding polypeptide and said second nucleic acid binding polypeptide are Bap and a binding domain to a bovine immunodeficiency virus (BIV) trans-activation response element (TAR) sequence of BIV trans-activator protein (Tat); and said first sequence and said second sequence are a boxB sequence and a BIV TAR sequence;

and, when said nucleic acid construct is introduced in a translation system, a fusion protein translated from the coding region of said nucleic acid construct forms a complex with an RNA corresponding to said nucleic acid construct by a bond between said first nucleic acid binding polypeptide and said first sequence and a bond between said second nucleic acid binding polypeptide and said second sequence.

2. The nucleic acid construct according to claim 1, wherein said 5'-untranslated region comprises a boxB sequence, a Cv sequence, and a ribosome binding sequence; and said coding region comprises a sequence coding for a polypeptide subjected to be displayed, a Bap-coding sequence, a Cvap dimer-coding sequence, and a spacer-coding sequence, that are linked in frame.

3. The nucleic acid construct according to claim 1, wherein said 5'-untranslated region comprises a boxB sequence, an apI sequence or apII sequence, and a ribosome binding sequence; and said coding region comprises a sequence coding for a polypeptide subjected to be displayed, a Bap-coding sequence, a sequence of a binding domain to an apI sequence or an apII sequence of Rev, and a spacer-coding sequence, that are linked in frame.

4. The nucleic acid construct according to claim 1, wherein said 5'-untranslated region comprises a boxB sequence, a BIV TAR sequence, and a ribosome binding sequence; and said coding region comprises a sequence coding for a polypeptide subjected to be displayed, a Bap-coding sequence, a sequence of a binding domain to a BIV TAR sequence of BIV Tat, and a spacer-coding sequence that are linked in frame.

5. The nucleic acid construct according to claim 1, wherein said 5'-untranslated region comprises a ribosome binding sequence.

6. The nucleic acid construct according to claim 1, wherein said sequence coding for a polypeptide subjected to be displayed is a sequence coding for a random polypeptide.

7. An in vitro method of selecting a polypeptide sequence that binds to a target substance, comprising repeating the following steps (1) to (3):

(1) expressing fusion proteins of a random polypeptide, the first nucleic acid binding polypeptide, and the second nucleic acid binding polypeptide from the nucleic acid construct according to claim 6 to display a random polypeptide library on said RNA corresponding to said nucleic acid construct;

(2) bringing a target substance into contact with said library; and (3) selecting a fusion protein comprising a polypeptide sequence that binds to said target substance and amplifying the nucleic acid sequence coding for the selected fusion protein.

8. The method according to claim 7 further comprising dissociating a ribosome from said nucleic acid construct between the steps (1) and (2).

9. An in vitro method of displaying a polypeptide on a nucleic acid comprising introducing said nucleic acid construct according to claim 1 in a translation system to express a fusion protein encoded by said coding region, forming a complex of the fusion protein and an RNA corresponding to said nucleic acid construct via a bond between the first nucleic acid binding polypeptide and the first sequence and a bond of the second nucleic acid binding polypeptide and the second sequence; and thereby displaying a polypeptide subjected to be displayed on the RNA corresponding to said nucleic acid construct.

10. The method according to claim 9 further comprising dissociating a ribosome from said nucleic acid construct after forming said complex of said fusion protein and said RNA corresponding to said nucleic acid construct.

11. A kit for displaying a polypeptide on a nucleic acid, the kit comprising said nucleic acid construct according to claim 1.

12. The nucleic acid construct according to claim 1, wherein 3 to 15 bases exist between said first sequence and said second sequence.

13. A nucleic acid-protein complex comprising an RNA as a nucleic acid construct comprising a 5'-untranslated region and a coding region and a fusion protein translated from said coding region, wherein said coding region comprises a sequence coding for a polypeptide subjected to be displayed, a sequence coding for a first nucleic acid binding polypeptide and a sequence coding for a second nucleic acid binding polypeptide; and said 5'-untranslated region comprises a first sequence capable of binding to the first nucleic acid binding polypeptide and a second sequence capable of binding to the second nucleic acid binding polypeptide, wherein said second sequence is independent from said first sequence;

wherein said first nucleic acid binding polypeptide and said second nucleic acid binding polypeptide are Bap and a Cvap dimer; and said first sequence and said second sequence are a boxB sequence and a Cv sequence;

which nucleic acid-protein complex is formed by a bond between said first nucleic acid binding polypeptide and said first sequence, and a bond between said second nucleic acid binding polypeptide and said second sequence.

14. The nucleic acid-protein complex according to claim 13 that does not comprise a ribosome.

15. The nucleic acid-protein complex according to claim 13, wherein said sequence coding for a polypeptide subjected to be displayed is a sequence coding for a random polypeptide.

16. The nucleic acid-protein complex according to claim 13, wherein 3 to 15 bases exist between said first sequence and said second sequence.

\* \* \* \* \*

SEQUENCE LISTING

<160> NUMBER OF SEQ ID NOS: 67

<210> SEQ ID NO 1
<211> LENGTH: 5414
<212> TYPE: DNA
<213> ORGANISM: Artificial Sequence
<220> FEATURE:
<223> OTHER INFORMATION: Description of Artificial Sequence: Synthetic
      plasmid DNA I full polynucleotide
<220> FEATURE:
<221> NAME/KEY: misc_feature
<222> LOCATION: (3650)..(3662)
<223> OTHER INFORMATION: SfiI

<400> SEQUENCE: 1

```
cttccgcttc ctcgctcact gactcgctgc gctcggtcgt tcggctgcgg cgagcggtat      60
cagctcactc aaaggcggta atacggttat ccacagaatc aggggataac gcaggaaaga     120
acatgtgagc aaaaggccag caaaaggcca ggaaccgtaa aaaggccgcg ttgctggcgt     180
ttttccatag gctccgcccc cctgacgagc atcacaaaaa tcgacgctca agtcagaggt     240
ggcgaaaccc gacaggacta taaagatacc aggcgtttcc ccctggaagc tccctcgtgc     300
gctctcctgt tccgaccctg ccgcttaccg gatacctgtc cgcctttctc ccttcgggaa     360
gcgtggcgct ttctcatagc tcacgctgta ggtatctcag ttcggtgtag gtcgttcgct     420
ccaagctggg ctgtgtgcac gaaccccccg ttcagcccga ccgctgcgcc ttatccggta     480
actatcgtct tgagtccaac ccggtaagac acgacttatc gccactggca gcagccactg     540
gtaacaggat tagcagagcg aggtatgtag gcggtgctac agagttcttg aagtggtggc     600
ctaactacgg ctacactaga agaacagtat ttggtatctg cgctctgctg aagccagtta     660
ccttcggaaa aagagttggt agctcttgat ccggcaaaca aaccaccgct ggtagcggtg     720
gtttttttgt ttgcaagcag cagattacgc gcagaaaaaa aggatctcaa gaagatcctt     780
tgatcttttc tacggggtct gacgctcagt ggaacgaaaa ctcacgttaa gggattttgg     840
tcatgagatt atcaaaaagg atcttcacct agatcctttt aaattaaaaa tgaagtttta     900
aatcaatcta agtatatat gagtaaactt ggtctgacag ttaccaatgc ttaatcagtg     960
```

```
aggcacctat ctcagcgatc tgtctatttc gttcatccat agttgcctga ctccccgtcg    1020
tgtagataac tacgatacgg gagggcttac catctggccc cagtgctgca atgataccgc    1080
gagacccacg ctcaccggct ccagatttat cagcaataaa ccagccagcc ggaagggccg    1140
agcgcagaag tggtcctgca actttatccg cctccatcca gtctattaat tgttgccggg    1200
aagctagagt aagtagttcg ccagttaata gtttgcgcaa cgttgttgcc attgctacag    1260
gcatcgtggt gtcacgctcg tcgtttggta tggcttcatt cagctccggt tcccaacgat    1320
caaggcgagt tacatgatcc cccatgttgt gcaaaaaagc ggttagctcc ttcggtcctc    1380
cgatcgttgt cagaagtaag ttggccgcag tgttatcact catggttatg gcagcactgc    1440
ataattctct tactgtcatg ccatccgtaa gatgcttttc tgtgactggt gagtactcaa    1500
ccaagtcatt ctgagaatag tgtatgcggc gaccgagttg ctcttgcccg cgtcaatac    1560 gggataatac cgcgccacat agcagaactt taaaagtgct catcattgga aaacgttctt    1620
cggggcgaaa actctcaagg atcttaccgc tgttgagatc cagttcgatg taacccactc    1680
gtgcacccaa ctgatcttca gcatctttta ctttcaccag cgtttctggg tgagcaaaaa    1740
caggaaggca aaatgccgca aaaaagggaa taagggcgac acggaaatgt tgaatactca    1800
tactcttcct ttttcaattc agaagaactc gtcaagaagg cgatagaagg cgatgcgctg    1860
cgaatcggga gcggcgatac cgtaaagcac gaggaagcgg tcagcccatt cgccgccaag    1920
ctcttcagca atatcacggg tagccaacgc tatgtcctga tagcggtccg ccacacccag    1980
ccggccacag tcgatgaatc cagaaaagcg gccattttcc accatgatat tcggcaagca    2040
ggcatcgcca tgggtcacga cgagatcctc gccgtcgggc atgcgcgcct tgagcctggc    2100
gaacagttcg gctggcgcga gcccctgatg ctcttcgtcc agatcatcct gatcgacaag    2160
accggcttcc atccgagtac gtgctcgctc gatgcgatgt ttcgcttggt ggtcgaatgg    2220
gcaggtagcc ggatcaagcg tatgcagccg ccgcattgca tcagccatga tggatacttt    2280
ctcggcagga gcaaggtggg atgacaggag atcctgcccc ggcacttcgc ccaatagcag    2340
ccagtccctt cccgcttcag tgacaacgtc gagcacagct gcgcaaggaa cgcccgtcgt    2400
ggccagccac gatagccgcg ctgcctcgtc ctgcagttca ttcagggcac cggacaggtc    2460
ggtcttgaca aaaagaaccg ggcgcccctg cgctgacagc cggaacacgg cggcatcaga    2520
gcagccgatt gtctgttgtg cccagtcata gccgaatagc ctctccaccc aagcggccgg    2580
agaacctgcg tgcaatccat cttgttcaat catgcgaaac gatcctcatc ctgtctcttg    2640
atcagatctt gatcccctgc gccatcagat ccttggcggc aagaaagcca tccagtttac    2700
tttgcagggc ttcccaacct taccagaggg cgccccagct ggcaattccg gttcgcttgc    2760
tgtccataaa accgcccagt ctagctatcg ccatgtaagc ccactgcaag ctacctgctt    2820
tctctttgcg cttgcgtttt cccttgtcca gatagcccag tagctgacat tcatccgggg    2880
tcagcaccgt ttctgcggac tggctttcta cgtgttccgc ttcctttagc agcccttgcg    2940
ccctgaattt tgttaaaatt cgcgttaaat ttttgttaaa tcagctcatt ttttaaccaa    3000
taggccgaaa tcggcaaaat cccttataaa tcaaaagaat agaccgagat agggttgagt    3060
gttgttccag tttggaacaa gagtccacta ttaaagaacg tggactccaa cgtcaaaggg    3120
cgaaaaaccg tctatcaggg cgatggccca ctacgtgaac catcacccta atcaagtttt    3180
ttggggtcga ggtgccgtaa agcactaaat cggaacccta agggagcccc cgatttaga    3240 gcttgacggg gaaagccggc gaacgtggcg agaaaggaag ggaagaaagc gaaaggagcg    3300
```

```
ggcgctaggg cgctggcaag tgtagcggtc acgctgcgcg taaccaccac acccgccgcg    3360
cttaatgcgc cgctacaggg cgcgtccatt cgccattcag gctgcgcaac tgttgggaag    3420
ggcgatcggt gcgggcctct tcgctattac gccagctggc gaaaggggga tgtgctgcaa    3480
ggcgattaag ttgggtaacg ccagggtttt cccagtcacg acgttgtaaa acgacggcca    3540
gtgaattgta atacgactca ctatagggcg aattgggccc tctagatgca tgctcgagcg    3600
gccgcgtcga caataatttt gtttaacttt aagaaggaga tatacatatg gccatgcagg    3660
ccagctaggc cagtctagtg gaggtggaaa tgctcgtact cggcgacgtg aacgcagagc    3720
catggaacga gctacgctgc cacaagtgct gggaggtgga tctttcgaac gccagcacat    3780
ggacagccca gatctgggta ccgacgacga cgacaaggct gcatctatgg cttctaactt    3840
tactcagttc gttctcgtcg acaatggcgg aactggcgac gtgactgtcg ccccaagcaa    3900
cttcgctaac ggggtcgctg aatggatcag ctctaactcg cgatcacagg cttacaaagt    3960
aacctgtagc gttcgtcaga gctctgcgca gaatcgcaaa tacaccatca agtcgaggt    4020 gcctaaagtg gcaacccaga ctgttggtgg tgaagagctt cctgtagccg gatggagatc    4080
ttacttaaat atggaactaa ccattccaat tttcgccacg aattccgact gcgagcttat    4140
tgttaaggca atgcaaggtc tcctaaaaga tggaaaccg attccctcgg ccatcgcagc    4200
aaactccggc atctacggtg gtggttcagg tggtggttca tctgcatcta tggcttctaa    4260
ctttactcag ttcgttctcg tcgacaatgg cggaactggc gacgtgactg tcgccccaag    4320
caacttcgct aacggggtcg ctgaatggat cagctctaac tcgcgatcac aggcttacaa    4380
agtaacctgt agcgttcgtc agagctctgc gcagaatcgc aaatacacca tcaaagtcga    4440
ggtgcctaaa gtggcaaccc agactgttgg tggtgaagag cttcctgtag ccggatggag    4500
atcttactta aatatggaac taaccattcc aatttccgcc acgaattccg actgcgagct    4560
tattgttaag gcaatgcaag gtctcctaaa agatggaaac ccgattccct cagcaatcgc    4620
agcaaactcc ggcatctacg gtggtggttc aggtggtggt tcatctgcag gtatgatcag    4680
tctgattgcg gcgttagcgg tagatcgcgt tatcggcatg gaaaacgcca tgccgtggaa    4740
cctgcctgcc gatctcgcct ggtttaaacg caacaccta aataaacccg tgattatggg    4800
ccgccatacc tgggaatcaa tcggtcgtcc gttgccagga cgcaaaaata ttatcctcag    4860
cagtcaaccg ggtacggacg atcgcgtaac gtgggtgaag tcggtggatg aagccatcgc    4920
ggcgtgtggt gacgtaccag aaatcatggt gattggcggc ggtcgcgttt atgaacagtt    4980
cttgccaaaa gcgcaaaaac tgtatctgac gcatatcgac gcagaagtgg aaggcgacac    5040
ccatttcccg gattacgagc cggatgactg ggaatcggta ttcagcgagt ccacgatgc    5100 tgatgcgcag aactctcaca gctattgctt tgagattctg gagcggcgga actcgaggga    5160
tccgagctcg gtaccaagct tggcgtaatc atggtcatag ctgtttcctg tgtgaaattg    5220
ttatccgctc acaattccac acaacatacg agccggaagc ataaagtgta aagcctgggg    5280
tgcctaatga gtgagctaac tcacattaat tgcgttgcgc tcactgcccg ctttccagtc    5340
gggaaacctg tcgtgccagc tgcattaatg aatcggccaa cgcgcgggga gaggcggttt    5400
gcgtattggg cgct                                                     5414
```

<210> SEQ ID NO 2
<211> LENGTH: 5478
<212> TYPE: DNA
<213> ORGANISM: Artificial Sequence
<220> FEATURE:
<223> OTHER INFORMATION: Description of Artificial Sequence: Synthetic

```
        plasmid DNA II full polynucleotide
<220> FEATURE:
<221> NAME/KEY: misc_feature
<222> LOCATION: (3714)..(3726)
<223> OTHER INFORMATION: SfiI

<400> SEQUENCE: 2
cttccgcttc ctcgctcact gactcgctgc gctcggtcgt tcggctgcgg cgagcggtat      60
cagctcactc aaaggcggta atacggttat ccacagaatc aggggataac gcaggaaaga     120
acatgtgagc aaaaggccag caaaaggcca ggaaccgtaa aaaggccgcg ttgctggcgt     180
ttttccatag gctccgcccc cctgacgagc atcacaaaaa tcgacgctca agtcagaggt     240
ggcgaaaccc gacaggacta taaagatacc aggcgtttcc ccctggaagc tccctcgtgc     300
gctctcctgt tccgaccctg ccgcttaccg gatacctgtc cgcctttctc ccttcgggaa     360
gcgtggcgct ttctcatagc tcacgctgta ggtatctcag ttcggtgtag gtcgttcgct     420
ccaagctggg ctgtgtgcac gaaccccccg ttcagcccga ccgctgcgcc ttatccggta     480
actatcgtct tgagtccaac ccggtaagac acgacttatc gccactggca gcagccactg     540
gtaacaggat tagcagagcg aggtatgtag gcggtgctac agagttcttg aagtggtggc     600
ctaactacgg ctacactaga agaacagtat ttggtatctg cgctctgctg aagccagtta     660
ccttcggaaa aagagttggt agctcttgat ccggcaaaca aaccaccgct ggtagcggtg     720
gtttttttgt ttgcaagcag cagattacgc gcagaaaaaa aggatctcaa gaagatcctt     780
tgatcttttc tacggggtct gacgctcagt ggaacgaaaa ctcacgttaa gggattttgg     840
tcatgagatt atcaaaaagg atcttcacct agatcctttt aaattaaaaa tgaagtttta     900
aatcaatcta agtatatatg agtaaacttg gtctgacagt taccaatgct taatcagtg      960 aggcacctat ctcagcgatc tgtctatttc gttcatccat agttgcctga ctccccgtcg    1020
tgtagataac tacgatacgg gagggcttac catctggccc cagtgctgca atgataccgc    1080
gagacccacg ctcaccggct ccagatttat cagcaataaa ccagccagcc ggaagggccg    1140
agcgcagaag tggtcctgca actttatccg cctccatcca gtctattaat tgttgccggg    1200
aagctagagt aagtagttcg ccagttaata gtttgcgcaa cgttgttgcc attgctacag    1260
gcatcgtggt gtcacgctcg tcgtttggta tggcttcatt cagctccggt tcccaacgat    1320
caaggcgagt tacatgatcc cccatgttgt gcaaaaaagc ggttagctcc ttcggtcctc    1380
cgatcgttgt cagaagtaag ttggccgcag tgttatcact catggttatg gcagcactgc    1440
ataattctct tactgtcatg ccatccgtaa gatgcttttc tgtgactggt gagtactcaa    1500
ccaagtcatt ctgagaatag tgtatgcggc gaccgagttg ctcttgcccg gcgtcaatac    1560
gggataatac cgcgccacat agcagaactt taaaagtgct catcattgga aaacgttctt    1620
cggggcgaaa actctcaagg atcttaccgc tgttgagatc cagttcgatg taacccactc    1680
gtgcacccaa ctgatcttca gcatctttta ctttcaccag cgtttctggg tgagcaaaaa    1740
caggaaggca aaatgccgca aaaaagggaa taagggcgac acggaaatgt tgaatactca    1800
tactcttcct ttttcaattc agaagaactc gtcaagaagg cgatagaagg cgatgcgctg    1860
cgaatcggga gcggcgatac cgtaaagcac gaggaagcgg tcagcccatt cgccgccaag    1920
ctcttcagca atatcacggg tagccaacgc tatgtcctga tagcggtccg ccacacccag    1980
ccggccacag tcgatgaatc cagaaaagcg gccattttcc accatgatat tcggcaagca    2040
ggcatcgcca tgggtcacga cgagatcctc gccgtcgggc atgcgcgcct tgagcctggc    2100
gaacagttcg gctggcgcga gccctgatg ctcttcgtcc agatcatcct gatcgacaag    2160
```

```
accggcttcc atccgagtac gtgctcgctc gatgcgatgt ttcgcttggt ggtcgaatgg    2220
gcaggtagcc ggatcaagcg tatgcagccg ccgcattgca tcagccatga tggatacttt    2280
ctcggcagga gcaaggtggg atgacaggag atcctgcccc ggcacttcgc ccaatagcag    2340 ccagtcccctt cccgcttcag tgacaacgtc gagcacagct gcgcaaggaa cgcccgtcgt    2400
ggccagccac gatagccgcg ctgcctcgtc ctgcagttca ttcagggcac cggacaggtc    2460
ggtcttgaca aaagaaccg ggcgccctg cgctgacagc cggaacacgg cggcatcaga      2520
gcagccgatt gtctgttgtg cccagtcata gccgaatagc ctctccaccc aagcggccgg    2580
agaacctgcg tgcaatccat cttgttcaat catgcgaaac gatcctcatc ctgtctcttg    2640
atcagatctt gatcccctgc gccatcagat ccttggcggc aagaaagcca tccagtttac    2700
tttgcagggc ttcccaacct taccagaggg cgccccagct ggcaattccg gttcgcttgc    2760
tgtccataaa accgcccagt ctagctatcg ccatgtaagc ccactgcaag ctacctgctt    2820
tctctttgcg cttgcgtttt ccttgtcca gatagcccag tagctgacat tcatccgggg     2880
tcagcaccgt ttctgcggac tggctttcta cgtgttccgc ttccttttagc agcccttgcg   2940 ccctgaattt tgttaaaatt cgcgttaaat ttttgttaaa tcagctcatt ttttaaccaa    3000
taggccgaaa tcggcaaaat cccttataaa tcaaaagaat agaccgagat agggttgagt    3060
gttgttccag tttggaacaa gagtccacta ttaaagaacg tggactccaa cgtcaaaggg    3120
cgaaaaaccg tctatcaggg cgatggccca ctacgtgaac catcacccta atcaagtttt    3180
ttggggtcga ggtgccgtaa agcactaaat cggaaccta aagggagccc ccgatttaga     3240
gcttgacggg gaaagccggc gaacgtggcg agaaaggaag ggaagaaagc gaaggagcg     3300 ggcgctaggg cgctggcaag tgtagcggtc acgctgcgcg taaccaccac acccgccgcg    3360
cttaatgcgc cgctacaggg cgcgtccatt cgccattcag gctgcgcaac tgttgggaag    3420
ggcgatcggt gcgggcctct tcgctattac gccagctggc gaaagggga tgtgctgcaa    3480 ggcgattaag ttgggtaacg ccagggtttt cccagtcacg acgttgtaaa acgacggcca   3540
gtgaattgta atacgactca ctatagggcg aattgggccc tctagatgca tgctcgagcg   3600
gccgcttaat acgactcact atagaggccc tgaaaaggg ccaaaaacat gaggatcacc    3660
catgtaaaag tcgacaataa ttttgtttaa ctttaagaag gagatataca tatggccatg    3720
caggccagct aggccagtct agtggaggtg gaaatgctcg tactcggcga cgtgaacgca   3780
gagccatgga acgagctacg ctgccacaag tgctgggagg tggatctttc gaacgccagc    3840
acatggacag cccagatctg gtaccgacg acgacgacaa ggctgcatct atggcttcta    3900
actttactca gttcgttctc gtcgacaatg gcggaactgg cgacgtgact gtcgcccaa    3960 gcaacttcgc taacgggtc gctgaatgga tcagctctaa ctcgcgatca caggcttaca    4020
aagtaacctg tagcgttcgt cagagctctg cgcagaatcg caaatacacc atcaaagtcg    4080
aggtgcctaa agtggcaacc cagactgttg gtggtgaaga gcttcctgta gccggatgga    4140
gatcttactt aaatatggaa ctaaccattc caattttcgc cacgaattcc gactgcgagc    4200
ttattgttaa ggcaatgcaa ggtctcctaa aagatggaaa cccgattccc tcggccatcg    4260
cagcaaactc cggcatctac ggtggtggtt caggtggtgg ttcatctgca tctatggctt   4320
ctaactttac tcagttcgtt ctcgtcgaca atggcggaac tggcgacgtg actgtcgccc    4380
caagcaactt cgctaacggg gtcgctgaat ggatcagctc taactcgcga tcacaggctt    4440
acaaagtaac ctgtagcgtt cgtcagagct ctgcgcagaa tcgcaaatac accatcaaag    4500
```

```
tcgaggtgcc taaagtggca acccagactg ttggtggtga agagcttcct gtagccggat    4560
ggagatctta cttaaatatg gaactaacca ttccaatttt cgccacgaat tccgactgcg    4620
agcttattgt taaggcaatg caaggtctcc taaaagatgg aaacccgatt ccctcagcaa    4680
tcgcagcaaa ctccggcatc tacggtggtg gttcaggtgg tggttcatct gcaggtatga    4740
tcagtctgat tgcggcgtta gcggtagatc gcgttatcgg catggaaaac gccatgccgt    4800
ggaacctgcc tgccgatctc gcctggttta acgcaacac cttaaataaa cccgtgatta    4860
tgggccgcca tacctgggaa tcaatcggtc gtccgttgcc aggacgcaaa aatattatcc    4920
tcagcagtca accgggtacg gacgatcgcg taacgtgggt gaagtcggtg gatgaagcca    4980
tcgcggcgtg tggtgacgta ccagaaatca tggtgattgg cggcggtcgc gtttatgaac    5040
agttcttgcc aaaagcgcaa aaactgtatc tgacgcatat cgacgcagaa gtggaaggcg    5100
acacccattt cccggattac gagccggatg actgggaatc ggtattcagc gagttccacg    5160
atgctgatgc gcagaactct cacagctatt gctttgagat tctggagcgg cggaactcga    5220
gggatccgag ctcggtacca agcttggcgt aatcatggtc atagctgttt cctgtgtgaa    5280
attgttatcc gctcacaatt ccacacaaca tacgagccgg aagcataaag tgtaaagcct    5340
ggggtgccta atgagtgagc taactcacat taattgcgtt gcgctcactg cccgctttcc    5400
agtcgggaaa cctgtcgtgc cagctgcatt aatgaatcgg ccaacgcgcg gggagaggcg    5460
gtttgcgtat tgggcgct                                                  5478
```

<210> SEQ ID NO 3
<211> LENGTH: 1563
<212> TYPE: DNA
<213> ORGANISM: Artificial Sequence
<220> FEATURE:
<223> OTHER INFORMATION: Description of Artificial Sequence: Synthetic
      plasmid DNA I-FLAG partial polynucleotide
<220> FEATURE:
<221> NAME/KEY: RBS
<222> LOCATION: (29)..(34)
<220> FEATURE:
<221> NAME/KEY: CDS
<222> LOCATION: (43)..(1563)
<220> FEATURE:
<221> NAME/KEY: misc_feature
<222> LOCATION: (45)..(57)
<223> OTHER INFORMATION: SfiI
<220> FEATURE:
<221> NAME/KEY: misc_feature
<222> LOCATION: (58)..(81)
<223> OTHER INFORMATION: FLAG
<220> FEATURE:
<221> NAME/KEY: misc_feature
<222> LOCATION: (82)..(94)
<223> OTHER INFORMATION: SfiI
<220> FEATURE:
<221> NAME/KEY: misc_feature
<222> LOCATION: (109)..(174)
<223> OTHER INFORMATION: Bap
<220> FEATURE:
<221> NAME/KEY: misc_feature
<222> LOCATION: (250)..(639)
<223> OTHER INFORMATION: Cvap
<220> FEATURE:
<221> NAME/KEY: misc_feature
<222> LOCATION: (673)..(1062)
<223> OTHER INFORMATION: Cvap
<220> FEATURE:
<221> NAME/KEY: misc_feature
<222> LOCATION: (1063)..(1563)
<223> OTHER INFORMATION: Spacer

<400> SEQUENCE: 3

-continued

| | |
|---|---|
| gtcgacaata attttgttta actttaagaa ggagatatac at atg gcc atg cag<br>                                                                           Met Ala Met Gln<br>                                                                           1 | 54 |
| gcc gac tac aag gac gat gac aag ggc cag cta ggc cag tct agt<br>Ala Asp Tyr Lys Asp Asp Asp Lys Gly Gln Leu Gly Gln Ser Ser<br>5                           10                           15                      20 | 102 |
| gga ggt gga aat gct cgt act cgg cga cgt gaa cgc aga gcc atg gaa<br>Gly Gly Gly Asn Ala Arg Thr Arg Arg Glu Arg Arg Ala Met Glu<br>                 25                           30                         35 | 150 |
| cga gct acg ctg cca caa gtg ctg gga ggt gga tct ttc gaa cgc cag<br>Arg Ala Thr Leu Pro Gln Val Leu Gly Gly Gly Ser Phe Glu Arg Gln<br>           40                        45                         50 | 198 |
| cac atg gac agc cca gat ctg ggt acc gac gac gac aag gct gca<br>His Met Asp Ser Pro Asp Leu Gly Thr Asp Asp Asp Lys Ala Ala<br>             55                     60                     65 | 246 |
| tct atg gct tct aac ttt act cag ttc gtt ctc gtc gac aat ggc gga<br>Ser Met Ala Ser Asn Phe Thr Gln Phe Val Leu Val Asp Asn Gly Gly<br>70                         75                          80 | 294 |
| act ggc gac gtg act gtc gcc cca agc aac ttc gct aac ggg gtc gct<br>Thr Gly Asp Val Thr Val Ala Pro Ser Asn Phe Ala Asn Gly Val Ala<br>85                         90                          95                     100 | 342 |
| gaa tgg atc agc tct aac tcg cga tca cag gct tac aaa gta acc tgt<br>Glu Trp Ile Ser Ser Asn Ser Arg Ser Gln Ala Tyr Lys Val Thr Cys<br>                 105                      110                    115 | 390 |
| agc gtt cgt cag agc tct gcg cag aat cgc aaa tac acc atc aaa gtc<br>Ser Val Arg Gln Ser Ser Ala Gln Asn Arg Lys Tyr Thr Ile Lys Val<br>         120                      125                    130 | 438 |
| gag gtg cct aaa gtg gca acc cag act gtt ggt ggt gaa gag ctt cct<br>Glu Val Pro Lys Val Ala Thr Gln Thr Val Gly Gly Glu Glu Leu Pro<br>          135                     140                    145 | 486 |
| gta gcc gga tgg aga tct tac tta aat atg gaa cta acc att cca att<br>Val Ala Gly Trp Arg Ser Tyr Leu Asn Met Glu Leu Thr Ile Pro Ile<br>        150                      155                    160 | 534 |
| ttc gcc acg aat tcc gac tgc gag ctt att gtt aag gca atg caa ggt<br>Phe Ala Thr Asn Ser Asp Cys Glu Leu Ile Val Lys Ala Met Gln Gly<br>165                        170                        175                    180 | 582 |
| ctc cta aaa gat gga aac ccg att ccc tcg gcc atc gca gca aac tcc<br>Leu Leu Lys Asp Gly Asn Pro Ile Pro Ser Ala Ile Ala Ala Asn Ser<br>                 185                      190                    195 | 630 |
| ggc atc tac ggt ggt ggt tca ggt ggt ggt tca tct gca tct atg gct<br>Gly Ile Tyr Gly Gly Gly Ser Gly Gly Gly Ser Ser Ala Ser Met Ala<br>         200                      205                    210 | 678 |
| tct aac ttt act cag ttc gtt ctc gtc gac aat ggc gga act ggc gac<br>Ser Asn Phe Thr Gln Phe Val Leu Val Asp Asn Gly Gly Thr Gly Asp<br>         215                      220                    225 | 726 |
| gtg act gtc gcc cca agc aac ttc gct aac ggg gtc gct gaa tgg atc<br>Val Thr Val Ala Pro Ser Asn Phe Ala Asn Gly Val Ala Glu Trp Ile<br>230                        235                        240 | 774 |
| agc tct aac tcg cga tca cag gct tac aaa gta acc tgt agc gtt cgt<br>Ser Ser Asn Ser Arg Ser Gln Ala Tyr Lys Val Thr Cys Ser Val Arg<br>245                        250                        255                    260 | 822 |
| cag agc tct gcg cag aat cgc aaa tac acc atc aaa gtc gag gtg cct<br>Gln Ser Ser Ala Gln Asn Arg Lys Tyr Thr Ile Lys Val Glu Val Pro<br>                 265                      270                    275 | 870 |
| aaa gtg gca acc cag act gtt ggt ggt gaa gag ctt cct gta gcc gga<br>Lys Val Ala Thr Gln Thr Val Gly Gly Glu Glu Leu Pro Val Ala Gly<br>             280                      285                    290 | 918 |
| tgg aga tct tac tta aat atg gaa cta acc att cca att ttc gcc acg<br>Trp Arg Ser Tyr Leu Asn Met Glu Leu Thr Ile Pro Ile Phe Ala Thr<br>         295                      300                    305 | 966 |

```
aat tcc gac tgc gag ctt att gtt aag gca atg caa ggt ctc cta aaa    1014
Asn Ser Asp Cys Glu Leu Ile Val Lys Ala Met Gln Gly Leu Leu Lys
    310                 315                 320 gat gga aac ccg att ccc tca gca atc gca gca aac tcc ggc atc tac    1062
Asp Gly Asn Pro Ile Pro Ser Ala Ile Ala Ala Asn Ser Gly Ile Tyr
325                 330                 335                 340 ggt ggt ggt tca ggt ggt ggt tca tct gca ggt atg atc agt ctg att    1110
Gly Gly Gly Ser Gly Gly Gly Ser Ser Ala Gly Met Ile Ser Leu Ile
                345                 350                 355 gcg gcg tta gcg gta gat cgc gtt atc ggc atg gaa aac gcc atg ccg    1158
Ala Ala Leu Ala Val Asp Arg Val Ile Gly Met Glu Asn Ala Met Pro
            360                 365                 370 tgg aac ctg cct gcc gat ctc gcc tgg ttt aaa cgc aac acc tta aat    1206
Trp Asn Leu Pro Ala Asp Leu Ala Trp Phe Lys Arg Asn Thr Leu Asn
        375                 380                 385 aaa ccc gtg att atg ggc cgc cat acc tgg gaa tca atc ggt cgt ccg    1254
Lys Pro Val Ile Met Gly Arg His Thr Trp Glu Ser Ile Gly Arg Pro
    390                 395                 400 ttg cca gga cgc aaa aat att atc ctc agc agt caa ccg ggt acg gac    1302
Leu Pro Gly Arg Lys Asn Ile Ile Leu Ser Ser Gln Pro Gly Thr Asp
405                 410                 415                 420 gat cgc gta acg tgg gtg aag tcg gtg gat gaa gcc atc gcg gcg tgt    1350
Asp Arg Val Thr Trp Val Lys Ser Val Asp Glu Ala Ile Ala Ala Cys
                425                 430                 435 ggt gac gta cca gaa atc atg gtg att ggc ggc ggt cgc gtt tat gaa    1398
Gly Asp Val Pro Glu Ile Met Val Ile Gly Gly Gly Arg Val Tyr Glu
            440                 445                 450 cag ttc ttg cca aaa gcg caa aaa ctg tat ctg acg cat atc gac gca    1446
Gln Phe Leu Pro Lys Ala Gln Lys Leu Tyr Leu Thr His Ile Asp Ala
        455                 460                 465 gaa gtg gaa ggc gac acc cat ttc ccg gat tac gag ccg gat gac tgg    1494
Glu Val Glu Gly Asp Thr His Phe Pro Asp Tyr Glu Pro Asp Asp Trp
    470                 475                 480 gaa tcg gta ttc agc gag ttc cac gat gct gat gcg cag aac tct cac    1542
Glu Ser Val Phe Ser Glu Phe His Asp Ala Asp Ala Gln Asn Ser His
485                 490                 495                 500 agc tat tgc ttt gag att ctg                                        1563
Ser Tyr Cys Phe Glu Ile Leu
                505

<210> SEQ ID NO 4
<211> LENGTH: 507
<212> TYPE: PRT
<213> ORGANISM: Artificial Sequence
<220> FEATURE:
<223> OTHER INFORMATION: Description of Artificial Sequence: Synthetic
      plasmid DNA I-FLAG partial polypeptide

<400> SEQUENCE: 4

Met Ala Met Gln Ala Asp Tyr Lys Asp Asp Asp Asp Lys Gly Gln Leu
1               5                   10                  15

Gly Gln Ser Ser Gly Gly Gly Asn Ala Arg Thr Arg Arg Glu Arg
            20                  25                  30

Arg Ala Met Glu Arg Ala Thr Leu Pro Gln Val Leu Gly Gly Gly Ser
            35                  40                  45

Phe Glu Arg Gln His Met Asp Ser Pro Asp Leu Gly Thr Asp Asp Asp
    50                  55                  60

Asp Lys Ala Ala Ser Met Ala Ser Asn Phe Thr Gln Phe Val Leu Val
65                  70                  75                  80
```

-continued

```
Asp Asn Gly Gly Thr Gly Asp Val Thr Val Ala Pro Ser Asn Phe Ala
                85                  90                  95

Asn Gly Val Ala Glu Trp Ile Ser Ser Asn Ser Arg Ser Gln Ala Tyr
            100                 105                 110

Lys Val Thr Cys Ser Val Arg Gln Ser Ser Ala Gln Asn Arg Lys Tyr
        115                 120                 125

Thr Ile Lys Val Glu Val Pro Lys Val Ala Thr Gln Thr Val Gly Gly
    130                 135                 140

Glu Glu Leu Pro Val Ala Gly Trp Arg Ser Tyr Leu Asn Met Glu Leu
145                 150                 155                 160

Thr Ile Pro Ile Phe Ala Thr Asn Ser Asp Cys Glu Leu Ile Val Lys
                165                 170                 175

Ala Met Gln Gly Leu Leu Lys Asp Gly Asn Pro Ile Pro Ser Ala Ile
            180                 185                 190

Ala Ala Asn Ser Gly Ile Tyr Gly Gly Gly Ser Gly Gly Gly Ser Ser
        195                 200                 205

Ala Ser Met Ala Ser Asn Phe Thr Gln Phe Val Leu Val Asp Asn Gly
    210                 215                 220

Gly Thr Gly Asp Val Thr Val Ala Pro Ser Asn Phe Ala Asn Gly Val
225                 230                 235                 240

Ala Glu Trp Ile Ser Ser Asn Ser Arg Ser Gln Ala Tyr Lys Val Thr
                245                 250                 255

Cys Ser Val Arg Gln Ser Ser Ala Gln Asn Arg Lys Tyr Thr Ile Lys
            260                 265                 270

Val Glu Val Pro Lys Val Ala Thr Gln Thr Val Gly Gly Glu Glu Leu
        275                 280                 285

Pro Val Ala Gly Trp Arg Ser Tyr Leu Asn Met Glu Leu Thr Ile Pro
    290                 295                 300

Ile Phe Ala Thr Asn Ser Asp Cys Glu Leu Ile Val Lys Ala Met Gln
305                 310                 315                 320

Gly Leu Leu Lys Asp Gly Asn Pro Ile Pro Ser Ala Ile Ala Ala Asn
                325                 330                 335

Ser Gly Ile Tyr Gly Gly Gly Ser Gly Gly Gly Ser Ser Ala Gly Met
            340                 345                 350

Ile Ser Leu Ile Ala Ala Leu Ala Val Asp Arg Val Ile Gly Met Glu
        355                 360                 365

Asn Ala Met Pro Trp Asn Leu Pro Ala Asp Leu Ala Trp Phe Lys Arg
    370                 375                 380

Asn Thr Leu Asn Lys Pro Val Ile Met Gly Arg His Thr Trp Glu Ser
385                 390                 395                 400

Ile Gly Arg Pro Leu Pro Gly Arg Lys Asn Ile Ile Leu Ser Ser Gln
                405                 410                 415

Pro Gly Thr Asp Asp Arg Val Thr Trp Val Lys Ser Val Asp Glu Ala
            420                 425                 430

Ile Ala Ala Cys Gly Asp Val Pro Glu Ile Met Val Ile Gly Gly Gly
        435                 440                 445

Arg Val Tyr Glu Gln Phe Leu Pro Lys Ala Gln Lys Leu Tyr Leu Thr
    450                 455                 460

His Ile Asp Ala Glu Val Glu Gly Asp Thr His Phe Pro Asp Tyr Glu
465                 470                 475                 480

Pro Asp Asp Trp Glu Ser Val Phe Ser Glu Phe His Asp Ala Asp Ala
                485                 490                 495

Gln Asn Ser His Ser Tyr Cys Phe Glu Ile Leu
```

<210> SEQ ID NO 5
<211> LENGTH: 1626
<212> TYPE: DNA
<213> ORGANISM: Artificial Sequence
<220> FEATURE:
<223> OTHER INFORMATION: Description of Artificial Sequence: Synthetic plasmid DNA II-FLAG partial polynucleotide
<220> FEATURE:
<221> NAME/KEY: promoter
<222> LOCATION: (1)..(17)
<220> FEATURE:
<221> NAME/KEY: misc_feature
<222> LOCATION: (20)..(35)
<223> OTHER INFORMATION: boxB
<220> FEATURE:
<221> NAME/KEY: misc_feature
<222> LOCATION: (41)..(59)
<223> OTHER INFORMATION: Cv
<220> FEATURE:
<221> NAME/KEY: RBS
<222> LOCATION: (92)..(97)
<220> FEATURE:
<221> NAME/KEY: CDS
<222> LOCATION: (106)..(1626)
<220> FEATURE:
<221> NAME/KEY: misc_feature
<222> LOCATION: (108)..(120)
<223> OTHER INFORMATION: SfiI
<220> FEATURE:
<221> NAME/KEY: misc_feature
<222> LOCATION: (121)..(144)
<223> OTHER INFORMATION: FLAG
<220> FEATURE:
<221> NAME/KEY: misc_feature
<222> LOCATION: (145)..(157)
<223> OTHER INFORMATION: SfiI
<220> FEATURE:
<221> NAME/KEY: misc_feature
<222> LOCATION: (172)..(240)
<223> OTHER INFORMATION: Bap
<220> FEATURE:
<221> NAME/KEY: misc_feature
<222> LOCATION: (313)..(702)
<223> OTHER INFORMATION: Cvap
<220> FEATURE:
<221> NAME/KEY: misc_feature
<222> LOCATION: (736)..(1125)
<223> OTHER INFORMATION: Cvap
<220> FEATURE:
<221> NAME/KEY: misc_feature
<222> LOCATION: (1126)..(1626)
<223> OTHER INFORMATION: Spacer

<400> SEQUENCE: 5

```
taatacgact cactatagag gccctgaaaa agggccaaaa acatgaggat cacccatgta      60
aaagtcgaca ataattttgt ttaactttaa gaaggagata tacat atg gcc atg cag     117
                                                   Met Ala Met Gln
                                                    1 gcc gac tac aag gac gat gac gac aag ggc cag cta ggc cag tct agt      165
Ala Asp Tyr Lys Asp Asp Asp Asp Lys Gly Gln Leu Gly Gln Ser Ser
 5                  10                  15                  20 gga ggt gga aat gct cgt act cgg cga cgt gaa cgc aga gcc atg gaa      213
Gly Gly Gly Asn Ala Arg Thr Arg Arg Arg Glu Arg Arg Ala Met Glu
             25                  30                  35 cga gct acg ctg cca caa gtg ctg gga ggt gga tct ttc gaa cgc cag      261
Arg Ala Thr Leu Pro Gln Val Leu Gly Gly Gly Ser Phe Glu Arg Gln
         40                  45                  50 cac atg gac agc cca gat ctg ggt acc gac gac gac gac aag gct gca      309
His Met Asp Ser Pro Asp Leu Gly Thr Asp Asp Asp Asp Lys Ala Ala
     55                  60                  65
```

| | | |
|---|---|---|
| tct atg gct tct aac ttt act cag ttc gtt ctc gtc gac aat ggc gga<br>Ser Met Ala Ser Asn Phe Thr Gln Phe Val Leu Val Asp Asn Gly Gly<br>70 75 80 | 357 | |
| act ggc gac gtg act gtc gcc cca agc aac ttc gct aac ggg gtc gct<br>Thr Gly Asp Val Thr Val Ala Pro Ser Asn Phe Ala Asn Gly Val Ala<br>85 90 95 100 | 405 | |
| gaa tgg atc agc tct aac tcg cga tca cag gct tac aaa gta acc tgt<br>Glu Trp Ile Ser Ser Asn Ser Arg Ser Gln Ala Tyr Lys Val Thr Cys<br>105 110 115 | 453 | |
| agc gtt cgt cag agc tct gcg cag aat cgc aaa tac acc atc aaa gtc<br>Ser Val Arg Gln Ser Ser Ala Gln Asn Arg Lys Tyr Thr Ile Lys Val<br>120 125 130 | 501 | |
| gag gtg cct aaa gtg gca acc cag act gtt ggt ggt gaa gag ctt cct<br>Glu Val Pro Lys Val Ala Thr Gln Thr Val Gly Gly Glu Glu Leu Pro<br>135 140 145 | 549 | |
| gta gcc gga tgg aga tct tac tta aat atg gaa cta acc att cca att<br>Val Ala Gly Trp Arg Ser Tyr Leu Asn Met Glu Leu Thr Ile Pro Ile<br>150 155 160 | 597 | |
| ttc gcc acg aat tcc gac tgc gag ctt att gtt aag gca atg caa ggt<br>Phe Ala Thr Asn Ser Asp Cys Glu Leu Ile Val Lys Ala Met Gln Gly<br>165 170 175 180 | 645 | |
| ctc cta aaa gat gga aac ccg att ccc tcg gcc atc gca gca aac tcc<br>Leu Leu Lys Asp Gly Asn Pro Ile Pro Ser Ala Ile Ala Ala Asn Ser<br>185 190 195 | 693 | |
| ggc atc tac ggt ggt ggt tca ggt ggt ggt tca tct gca tct atg gct<br>Gly Ile Tyr Gly Gly Gly Ser Gly Gly Gly Ser Ser Ala Ser Met Ala<br>200 205 210 | 741 | |
| tct aac ttt act cag ttc gtt ctc gtc gac aat ggc gga act ggc gac<br>Ser Asn Phe Thr Gln Phe Val Leu Val Asp Asn Gly Gly Thr Gly Asp<br>215 220 225 | 789 | |
| gtg act gtc gcc cca agc aac ttc gct aac ggg gtc gct gaa tgg atc<br>Val Thr Val Ala Pro Ser Asn Phe Ala Asn Gly Val Ala Glu Trp Ile<br>230 235 240 | 837 | |
| agc tct aac tcg cga tca cag gct tac aaa gta acc tgt agc gtt cgt<br>Ser Ser Asn Ser Arg Ser Gln Ala Tyr Lys Val Thr Cys Ser Val Arg<br>245 250 255 260 | 885 | |
| cag agc tct gcg cag aat cgc aaa tac acc atc aaa gtc gag gtg cct<br>Gln Ser Ser Ala Gln Asn Arg Lys Tyr Thr Ile Lys Val Glu Val Pro<br>265 270 275 | 933 | |
| aaa gtg gca acc cag act gtt ggt ggt gaa gag ctt cct gta gcc gga<br>Lys Val Ala Thr Gln Thr Val Gly Gly Glu Glu Leu Pro Val Ala Gly<br>280 285 290 | 981 | |
| tgg aga tct tac tta aat atg gaa cta acc att cca att ttc gcc acg<br>Trp Arg Ser Tyr Leu Asn Met Glu Leu Thr Ile Pro Ile Phe Ala Thr<br>295 300 305 | 1029 | |
| aat tcc gac tgc gag ctt att gtt aag gca atg caa ggt ctc cta aaa<br>Asn Ser Asp Cys Glu Leu Ile Val Lys Ala Met Gln Gly Leu Leu Lys<br>310 315 320 | 1077 | |
| gat gga aac ccg att ccc tca gca atc gca gca aac tcc ggc atc tac<br>Asp Gly Asn Pro Ile Pro Ser Ala Ile Ala Ala Asn Ser Gly Ile Tyr<br>325 330 335 340 | 1125 | |
| ggt ggt ggt tca ggt ggt ggt tca tct gca ggt atg atc agt ctg att<br>Gly Gly Gly Ser Gly Gly Gly Ser Ser Ala Gly Met Ile Ser Leu Ile<br>345 350 355 | 1173 | |
| gcg gcg tta gcg gta gat cgc gtt atc ggc atg gaa aac gcc atg ccg<br>Ala Ala Leu Ala Val Asp Arg Val Ile Gly Met Glu Asn Ala Met Pro<br>360 365 370 | 1221 | |
| tgg aac ctg cct gcc gat ctc gcc tgg ttt aaa cgc aac acc tta aat<br>Trp Asn Leu Pro Ala Asp Leu Ala Trp Phe Lys Arg Asn Thr Leu Asn | 1269 | |

```
                375                 380                 385
aaa ccc gtg att atg ggc cgc cat acc tgg gaa tca atc ggt cgt ccg    1317
Lys Pro Val Ile Met Gly Arg His Thr Trp Glu Ser Ile Gly Arg Pro
    390                 395                 400 ttg cca gga cgc aaa aat att atc ctc agc agt caa ccg ggt acg gac    1365
Leu Pro Gly Arg Lys Asn Ile Ile Leu Ser Ser Gln Pro Gly Thr Asp
405                 410                 415                 420 gat cgc gta acg tgg gtg aag tcg gtg gat gaa gcc atc gcg gcg tgt    1413
Asp Arg Val Thr Trp Val Lys Ser Val Asp Glu Ala Ile Ala Ala Cys
                425                 430                 435 ggt gac gta cca gaa atc atg gtg att ggc ggc ggt cgc gtt tat gaa    1461
Gly Asp Val Pro Glu Ile Met Val Ile Gly Gly Gly Arg Val Tyr Glu
            440                 445                 450 cag ttc ttg cca aaa gcg caa aaa ctg tat ctg acg cat atc gac gca    1509
Gln Phe Leu Pro Lys Ala Gln Lys Leu Tyr Leu Thr His Ile Asp Ala
        455                 460                 465 gaa gtg gaa ggc gac acc cat ttc ccg gat tac gag ccg gat gac tgg    1557
Glu Val Glu Gly Asp Thr His Phe Pro Asp Tyr Glu Pro Asp Asp Trp
    470                 475                 480 gaa tcg gta ttc agc gag ttc cac gat gct gat gcg cag aac tct cac    1605
Glu Ser Val Phe Ser Glu Phe His Asp Ala Asp Ala Gln Asn Ser His
485                 490                 495                 500 agc tat tgc ttt gag att ctg                                        1626
Ser Tyr Cys Phe Glu Ile Leu
                505

<210> SEQ ID NO 6
<211> LENGTH: 507
<212> TYPE: PRT
<213> ORGANISM: Artificial Sequence
<220> FEATURE:
<223> OTHER INFORMATION: Description of Artificial Sequence: Synthetic
      plasmid DNA II-FLAG partial polypeptide

<400> SEQUENCE: 6

Met Ala Met Gln Ala Asp Tyr Lys Asp Asp Asp Asp Lys Gly Gln Leu
1               5                   10                  15

Gly Gln Ser Ser Gly Gly Gly Asn Ala Arg Thr Arg Arg Glu Arg
            20                  25                  30

Arg Ala Met Glu Arg Ala Thr Leu Pro Gln Val Leu Gly Gly Gly Ser
        35                  40                  45

Phe Glu Arg Gln His Met Asp Ser Pro Asp Leu Gly Thr Asp Asp Asp
    50                  55                  60

Asp Lys Ala Ala Ser Met Ala Ser Asn Phe Thr Gln Phe Val Leu Val
65                  70                  75                  80

Asp Asn Gly Gly Thr Gly Asp Val Thr Val Ala Pro Ser Asn Phe Ala
                85                  90                  95

Asn Gly Val Ala Glu Trp Ile Ser Ser Asn Ser Arg Ser Gln Ala Tyr
            100                 105                 110

Lys Val Thr Cys Ser Val Arg Gln Ser Ala Gln Asn Arg Lys Tyr
        115                 120                 125

Thr Ile Lys Val Glu Val Pro Lys Val Ala Thr Gln Thr Val Gly Gly
    130                 135                 140

Glu Glu Leu Pro Val Ala Gly Trp Arg Ser Tyr Leu Asn Met Glu Leu
145                 150                 155                 160

Thr Ile Pro Ile Phe Ala Thr Asn Ser Asp Cys Glu Leu Ile Val Lys
                165                 170                 175

Ala Met Gln Gly Leu Leu Lys Asp Gly Asn Pro Ile Pro Ser Ala Ile
```

180                 185                 190
Ala Ala Asn Ser Gly Ile Tyr Gly Gly Gly Ser Gly Gly Gly Ser Ser
                    195                 200                 205

Ala Ser Met Ala Ser Asn Phe Thr Gln Phe Val Leu Val Asp Asn Gly
        210                 215                 220

Gly Thr Gly Asp Val Thr Val Ala Pro Ser Asn Phe Ala Asn Gly Val
225                 230                 235                 240

Ala Glu Trp Ile Ser Ser Asn Ser Arg Ser Gln Ala Tyr Lys Val Thr
                245                 250                 255

Cys Ser Val Arg Gln Ser Ser Ala Gln Asn Arg Lys Tyr Thr Ile Lys
            260                 265                 270

Val Glu Val Pro Lys Val Ala Thr Gln Thr Val Gly Gly Glu Glu Leu
        275                 280                 285

Pro Val Ala Gly Trp Arg Ser Tyr Leu Asn Met Glu Leu Thr Ile Pro
    290                 295                 300

Ile Phe Ala Thr Asn Ser Asp Cys Glu Leu Ile Val Lys Ala Met Gln
305                 310                 315                 320

Gly Leu Leu Lys Asp Gly Asn Pro Ile Pro Ser Ala Ile Ala Ala Asn
                325                 330                 335

Ser Gly Ile Tyr Gly Gly Gly Ser Gly Gly Ser Ser Ala Gly Met
                340                 345                 350

Ile Ser Leu Ile Ala Ala Leu Ala Val Asp Arg Val Ile Gly Met Glu
            355                 360                 365

Asn Ala Met Pro Trp Asn Leu Pro Ala Asp Leu Ala Trp Phe Lys Arg
        370                 375                 380

Asn Thr Leu Asn Lys Pro Val Ile Met Gly Arg His Thr Trp Glu Ser
385                 390                 395                 400

Ile Gly Arg Pro Leu Pro Gly Arg Lys Asn Ile Ile Leu Ser Ser Gln
                405                 410                 415

Pro Gly Thr Asp Asp Arg Val Thr Trp Val Lys Ser Val Asp Glu Ala
            420                 425                 430

Ile Ala Ala Cys Gly Asp Val Pro Glu Ile Met Val Ile Gly Gly Gly
        435                 440                 445

Arg Val Tyr Glu Gln Phe Leu Pro Lys Ala Gln Lys Leu Tyr Leu Thr
    450                 455                 460

His Ile Asp Ala Glu Val Glu Gly Asp Thr His Phe Pro Asp Tyr Glu
465                 470                 475                 480

Pro Asp Asp Trp Glu Ser Val Phe Ser Glu Phe His Asp Ala Asp Ala
                485                 490                 495

Gln Asn Ser His Ser Tyr Cys Phe Glu Ile Leu
            500                 505

<210> SEQ ID NO 7
<211> LENGTH: 5442
<212> TYPE: DNA
<213> ORGANISM: Artificial Sequence
<220> FEATURE:
<223> OTHER INFORMATION: Description of Artificial Sequence: Synthetic
      plasmid DNAI-FLAG full polynucleotide

<400> SEQUENCE: 7
cttccgcttc ctcgctcact gactcgctgc gctcggtcgt tcggctgcgg cgagcggtat     60
cagctcactc aaaggcggta atacggttat ccacagaatc aggggataac gcaggaaaga   120
acatgtgagc aaaaggccag caaaaggcca ggaaccgtaa aaaggccgcg ttgctggcgt   180

```
ttttccatag gctccgcccc cctgacgagc atcacaaaaa tcgacgctca agtcagaggt    240
ggcgaaaccc gacaggacta taaagatacc aggcgtttcc ccctggaagc tccctcgtgc    300
gctctcctgt tccgaccctg ccgcttaccg gatacctgtc cgcctttctc ccttcgggaa    360
gcgtggcgct ttctcatagc tcacgctgta ggtatctcag ttcggtgtag gtcgttcgct    420
ccaagctggg ctgtgtgcac gaaccccccg ttcagcccga ccgctgcgcc ttatccggta    480
actatcgtct tgagtccaac ccggtaagac acgacttatc gccactggca gcagccactg    540
gtaacaggat tagcagagcg aggtatgtag gcggtgctac agagttcttg aagtggtggc    600
ctaactacgg ctacactaga agaacagtat ttggtatctg cgctctgctg aagccagtta    660
ccttcggaaa aagagttggt agctcttgat ccggcaaaca aaccaccgct ggtagcggtg    720
gtttttttgt ttgcaagcag cagattacgc gcagaaaaaa aggatctcaa gaagatcctt    780
tgatcttttc tacggggtct gacgctcagt ggaacgaaaa ctcacgttaa gggattttgg    840
tcatgagatt atcaaaaagg atcttcacct agatcctttt aaattaaaaa tgaagtttta    900
aatcaatcta aagtatatat gagtaaactt ggtctgacag ttaccaatgc ttaatcagtg    960
aggcacctat ctcagcgatc tgtctatttc gttcatccat agttgcctga ctccccgtcg   1020
tgtagataac tacgatacgg gagggcttac catctggccc cagtgctgca atgataccgc   1080
gagacccacg ctcaccggct ccagatttat cagcaataaa ccagccagcc ggaagggccg   1140
agcgcagaag tggtcctgca actttatccg cctccatcca gtctattaat tgttgccggg   1200
aagctagagt aagtagttcg ccagttaata gtttgcgcaa cgttgttgcc attgctacag   1260
gcatcgtggt gtcacgctcg tcgtttggta tggcttcatt cagctccggt tcccaacgat   1320
caaggcgagt tacatgatcc cccatgttgt gcaaaaaagc ggttagctcc ttcggtcctc   1380
cgatcgttgt cagaagtaag ttggccgcag tgttatcact catggttatg gcagcactgc   1440
ataattctct tactgtcatg ccatccgtaa gatgcttttc tgtgactggt gagtactcaa   1500
ccaagtcatt ctgagaatag tgtatgcggc gaccgagttg ctcttgcccg gcgtcaatac   1560
gggataatac cgcgccacat agcagaactt taaaagtgct catcattgga aaacgttctt   1620
cggggcgaaa actctcaagg atcttaccgc tgttgagatc cagttcgatg taacccactc   1680
gtgcacccaa ctgatcttca gcatctttta ctttcaccag cgtttctggg tgagcaaaaa   1740
caggaaggca aaatgccgca aaaaagggaa taagggcgac acggaaatgt tgaatactca   1800
tactcttcct ttttcaattc agaagaactc gtcaagaagg cgatagaagg cgatgcgctg   1860
cgaatcggga gcggcgatac cgtaaagcac gaggaagcgg tcagcccatt cgccgccaag   1920
ctcttcagca atatcacggg tagccaacgc tatgtcctga tagcggtccg ccacacccag   1980
ccggccacag tcgatgaatc cagaaaagcg gccattttcc accatgatat tcggcaagca   2040
ggcatcgcca tgggtcacga cgagatcctc gccgtcgggc atgcgcgcct tgagcctggc   2100
gaacagttcg gctggcgcga gcccctgatg ctcttcgtcc agatcatcct gatcgacaag   2160
accggcttcc atccgagtac gtgctcgctc gatgcgatgt ttcgcttggt ggtcgaatgg   2220
gcaggtagcc ggatcaagcg tatgcagccg ccgcattgca tcagccatga tggatacttt   2280
ctcggcagga gcaaggtggg atgacaggag atcctgcccc ggcacttcgc ccaatagcag   2340
ccagtccctt cccgcttcag tgacaacgtc gagcacagct gcgcaaggaa cgcccgtcgt   2400
ggccagccac gatagccgcg ctgcctcgtc ctgcagttca ttcagggcac cggacaggtc   2460
ggtcttgaca aaaagaaccg ggcgcccctg cgctgacagc cggaacacgg cggcatcaga   2520
gcagccgatt gtctgttgtg cccagtcata gccgaatagc ctctccaccc aagcggccgg   2580
```

```
agaacctgcg tgcaatccat cttgttcaat catgcgaaac gatcctcatc ctgtctcttg    2640
atcagatctt gatcccctgc gccatcagat ccttggcggc aagaaagcca tccagtttac    2700
tttgcagggc ttcccaacct taccagaggg cgccccagct ggcaattccg gttcgcttgc    2760
tgtccataaa accgcccagt ctagctatcg ccatgtaagc ccactgcaag ctacctgctt    2820
tctctttgcg cttgcgtttt cccttgtcca gatagcccag tagctgacat tcatccgggg    2880
tcagcaccgt ttctgcggac tggctttcta cgtgttccgc ttcctttagc agcccttgcg    2940
ccctgaattt tgttaaaatt cgcgttaaat ttttgttaaa tcagctcatt ttttaaccaa    3000
taggccgaaa tcggcaaaat cccttataaa tcaaaagaat agaccgagat agggttgagt    3060
gttgttccag tttggaacaa gagtccacta ttaagaacg tggactccaa cgtcaagggg    3120 cgaaaaccg tctatcaggg cgatggccca ctacgtgaac catcaccta atcaagtttt    3180 ttggggtcga ggtgccgtaa agcactaaat cggaaccta agggagccc ccgatttaga    3240 gcttgacgg gaaagccggc gaacgtggcg agaaaggaag gaagaaagc gaaggagcg    3300 ggcgctaggg cgctggcaag tgtagcggtc acgctgcgcg taaccaccac acccgccgcg    3360
cttaatgcgc cgctacaggg cgcgtccatt cgccattcag gctgcgcaac tgttgggaag    3420
ggcgatcggt gcgggcctct tcgctattac gccagctggc gaaaggggga tgtgctgcaa    3480
ggcgattaag ttgggtaacg ccagggtttt cccagtcacg acgttgtaaa acgacggcca    3540
gtgaattgta atacgactca ctatagggcg aattgggccc tctagatgca tgctcgagcg    3600
gccgcgtcga caataatttt gtttaacttt aagaaggaga tatacatatg gccatgcagg    3660
ccgactacaa ggacgatgac gacaagggcc agctaggcca gtctagtgga ggtggaaatg    3720
ctcgtactcg gcgacgtgaa cgcagagcca tggaacgagc tacgctgcca caagtgctgg    3780
gaggtggatc tttcgaacgc cagcacatgg acagcccaga tctgggtacc gacgacgacg    3840
acaaggctgc atctatggct tctaacttta ctcagttcgt tctcgtcgac aatggcggaa    3900
ctggcgacgt gactgtcgcc ccaagcaact tcgctaacgg ggtcgctgaa tggatcagct    3960
ctaactcgcg atcacaggct acaaagtaa cctgtagcgt tcgtcagagc tctgcgcaga    4020
atcgcaaata caccatcaaa gtcgaggtgc ctaaagtggc aacccagact gttggtggtg    4080
aagagcttcc tgtagccgga tgagatctt acttaaatat ggaactaacc attccaattt    4140
tcgccacgaa ttccgactgc gagcttattg ttaaggcaat gcaaggtctc ctaaaagatg    4200
gaaacccgat tccctcggcc atcgcagcaa actccggcat ctacggtggt ggttcaggtg    4260
gtggttcatc tgcatctatg gcttctaact ttactcagtt cgttctcgtc gacaatggcg    4320
gaactggcga cgtgactgtc gccccaagca acttcgctaa cggggtcgct gaatggatca    4380
gctctaactc gcgatcacag gcttacaaag taacctgtag cgttcgtcag agctctgcgc    4440
agaatcgcaa atacaccatc aaagtcgagg tgcctaaagt ggcaacccag actgttggtg    4500
gtgaagagct tcctgtagcc ggatggagat cttacttaaa tatggaacta accattccaa    4560
ttttcgccac gaattccgac tgcgagctta ttgttaaggc aatgcaaggt ctcctaaaag    4620
atggaaaccc gattccctca gcaatcgcag caaactccgg catctacggt ggtggttcag    4680
gtggtggttc atctgcaggt atgatcagtc tgattgcggc gttagcggta gatcgcgtta    4740
tcggcatgga aaacgccatg ccgtggaacc tgcctgccga tctcgcctgg tttaaacgca    4800
acaccttaaa taaacccgtg attatgggcc gccatacctg ggaatcaatc ggtcgtccgt    4860
tgccaggacg caaaaatatt atcctcagca gtcaaccggg tacggacgat cgcgtaacgt    4920
```

| | |
|---|---|
| gggtgaagtc ggtggatgaa gccatcgcgg cgtgtggtga cgtaccagaa atcatggtga | 4980 |
| ttggcggcgg tcgcgtttat gaacagttct tgccaaaagc gcaaaaactg tatctgacgc | 5040 |
| atatcgacgc agaagtggaa ggcgacaccc atttcccgga ttacgagccg gatgactggg | 5100 |
| aatcggtatt cagcgagttc cacgatgctg atgcgcagaa ctctcacagc tattgctttg | 5160 |
| agattctgga gcggcggaac tcgagggatc cgagctcggt accaagcttg gcgtaatcat | 5220 |
| ggtcatagct gtttcctgtg tgaaattgtt atccgctcac aattccacac aacatacgag | 5280 |
| ccggaagcat aaagtgtaaa gcctggggtg cctaatgagt gagctaactc acattaattg | 5340 |
| cgttgcgctc actgcccgct ttccagtcgg gaaacctgtc gtgccagctg cattaatgaa | 5400 |
| tcggccaacg cgcggggaga ggcggtttgc gtattgggcg ct | 5442 |

<210> SEQ ID NO 8
<211> LENGTH: 5506
<212> TYPE: DNA
<213> ORGANISM: Artificial Sequence
<220> FEATURE:
<223> OTHER INFORMATION: Description of Artificial Sequence: Synthetic
      plasmid DNAII-FLAG full polynucleotide

<400> SEQUENCE: 8

| | |
|---|---|
| cttccgcttc ctcgctcact gactcgctgc gctcggtcgt tcggctgcgg cgagcggtat | 60 |
| cagctcactc aaaggcggta atacggttat ccacagaatc aggggataac gcaggaaaga | 120 |
| acatgtgagc aaaaggccag caaaaggcca ggaaccgtaa aaaggccgcg ttgctggcgt | 180 |
| ttttccatag gctccgcccc cctgacgagc atcacaaaaa tcgacgctca agtcagaggt | 240 |
| ggcgaaaccc gacaggacta taaagatacc aggcgtttcc ccctggaagc tccctcgtgc | 300 |
| gctctcctgt tccgaccctg ccgcttaccg gatacctgtc cgcctttctc ccttcgggaa | 360 |
| gcgtggcgct ttctcatagc tcacgctgta ggtatctcag ttcggtgtag tcgttcgct | 420 |
| ccaagctggg ctgtgtgcac gaaccccccg ttcagcccga ccgctgcgcc ttatccggta | 480 |
| actatcgtct gagtccaac ccggtaagac acgacttatc gccactggca gcagccactg | 540 |
| gtaacaggat tagcagagcg aggtatgtag gcggtgctac agagttcttg aagtggtggc | 600 |
| ctaactacgg ctacactaga agaacagtat ttggtatctg cgctctgctg aagccagtta | 660 |
| ccttcggaaa aagagttggt agctcttgat ccggcaaaca aaccaccgct ggtagcggtg | 720 |
| gtttttttgt ttgcaagcag cagattacgc gcagaaaaaa aggatctcaa gaagatcctt | 780 |
| tgatcttttc tacggggtct gacgctcagt ggaacgaaaa ctcacgttaa gggattttgg | 840 |
| tcatgagatt atcaaaaagg atcttcacct agatcctttt aaattaaaaa tgaagtttta | 900 |
| aatcaatcta agtatatat gagtaaactt ggtctgacag ttaccaatgc ttaatcagtg | 960 |
| aggcacctat ctcagcgatc tgtctatttc gttcatccat agttgcctga ctccccgtcg | 1020 |
| tgtagataac tacgatacgg gagggcttac catctggccc cagtgctgca atgataccgc | 1080 |
| gagacccacg ctcaccggct ccagatttat cagcaataaa ccagccagcc ggaagggccg | 1140 |
| agcgcagaag tggtcctgca actttatccg cctccatcca gtctattaat tgttgccggg | 1200 |
| aagctagagt aagtagttcg ccagttaata gtttgcgcaa cgttgttgcc attgctacag | 1260 |
| gcatcgtggt gtcacgctcg tcgtttggta tggcttcatt cagctccggt tcccaacgat | 1320 |
| caaggcgagt tacatgatcc cccatgttgt gcaaaaaagc ggttagctcc ttcggtcctc | 1380 |
| cgatcgttgt cagaagtaag ttggccgcag tgttatcact catggttatg gcagcactgc | 1440 |
| ataattctct tactgtcatg ccatccgtaa gatgcttttc tgtgactggt gagtactcaa | 1500 |

| | |
|---|---|
| ccaagtcatt ctgagaatag tgtatgcggc gaccgagttg ctcttgcccg gcgtcaatac | 1560 |
| gggataatac cgcgccacat agcagaactt taaaagtgct catcattgga aaacgttctt | 1620 |
| cggggcgaaa actctcaagg atcttaccgc tgttgagatc cagttcgatg taacccactc | 1680 |
| gtgcacccaa ctgatcttca gcatctttta ctttcaccag cgtttctggg tgagcaaaaa | 1740 |
| caggaaggca aaatgccgca aaaaagggaa taagggcgac acggaaatgt tgaatactca | 1800 |
| tactcttcct ttttcaattc agaagaactc gtcaagaagg cgatagaagg cgatgcgctg | 1860 |
| cgaatcggga gcggcgatac cgtaaagcac gaggaagcgg tcagcccatt cgccgccaag | 1920 |
| ctcttcagca atatcacggg tagccaacgc tatgtcctga tagcggtccg ccacacccag | 1980 |
| ccggccacag tcgatgaatc cagaaaagcg gccattttcc accatgatat tcggcaagca | 2040 |
| ggcatcgcca tgggtcacga cgagatcctc gccgtcgggc atgcgcgcct tgagcctggc | 2100 |
| gaacagttcg gctggcgcga gcccctgatg ctcttcgtcc agatcatcct gatcgacaag | 2160 |
| accggcttcc atccgagtac gtgctcgctc gatgcgatgt ttcgcttggt ggtcgaatgg | 2220 |
| gcaggtagcc ggatcaagcg tatgcagccg ccgcattgca tcagccatga tggatacttt | 2280 |
| ctcggcagga gcaaggtggg atgacaggag atcctgcccc ggcacttcgc ccaatagcag | 2340 |
| ccagtcccct cccgcttcag tgacaacgtc gagcacagct gcgcaaggaa cgcccgtcgt | 2400 |
| ggccagccac gatagccgcg ctgcctcgtc ctgcagttca ttcagggcac cggacaggtc | 2460 |
| ggtcttgaca aaaagaaccg ggcgcccctg cgctgacagc cggaacacgg cggcatcaga | 2520 |
| gcagccgatt gtctgttgtg cccagtcata gccgaatagc ctctccaccc aagcggccgg | 2580 |
| agaacctgcg tgcaatccat cttgttcaat catgcgaaac gatcctcatc ctgtctcttg | 2640 |
| atcagatctt gatcccctgc gccatcagat ccttggcggc aagaaagcca tccagtttac | 2700 |
| tttgcagggc ttcccaacct taccagaggg cgccccagct ggcaattccg gttcgcttgc | 2760 |
| tgtccataaa accgcccagt ctagctatcg ccatgtaagc ccactgcaag ctacctgctt | 2820 |
| tctctttgcg cttgcgtttt cccttgtcca gatagcccag tagctgacat tcatccgggg | 2880 |
| tcagcaccgt ttctgcggac tggctttcta cgtgttccgc ttcctttagc agcccttgcg | 2940 |
| ccctgaattt tgttaaaatt cgcgttaaat ttttgttaaa tcagctcatt ttttaaccaa | 3000 |
| taggccgaaa tcggcaaaat cccttataaa tcaaaagaat agaccgagat agggttgagt | 3060 |
| gttgttccag tttggaacaa gagtccacta ttaaagaacg tggactccaa cgtcaaaggg | 3120 |
| cgaaaaaccg tctatcaggg cgatggccca ctacgtgaac catcacccta atcaagtttt | 3180 |
| ttggggtcga ggtgccgtaa agcactaaat cggaacccta aagggagccc cgatttaga | 3240 |
| gcttgacggg gaaagccggc gaacgtggcg agaaggaag ggaagaaagc gaaaggagcg | 3300 |
| ggcgctaggg cgctggcaag tgtagcggtc acgctgcgcg taaccaccac acccgccgcg | 3360 |
| cttaatgcgc cgctacaggg cgcgtccatt cgccattcag gctgcgcaac tgttgggaag | 3420 |
| ggcgatcggt gcgggcctct tcgctattac gccagctggc gaaaggggga tgtgctgcaa | 3480 |
| ggcgattaag ttgggtaacg ccagggtttt cccagtcacg acgttgtaaa acgacggcca | 3540 |
| gtgaattgta atacgactca ctatagggcg aattgggccc tctagatgca tgctcgagcg | 3600 |
| gccgcttaat acgactcact atagaggccc tgaaaaaggg ccaaaaacat gaggatcacc | 3660 |
| catgtaaaag tcgacaataa ttttgtttaa ctttaagaag gagatataca tatggccatg | 3720 |
| caggccgact acaaggacga tgacgacaag ggccagctag gccagtctag tggaggtgga | 3780 |
| aatgctcgta ctcggcgacg tgaacgcaga gccatggaac gagctacgct gccacaagtg | 3840 |
| ctgggaggtg gatctttcga acgccagcac atggacagcc cagatctggg taccgacgac | 3900 |

```
gacgacaagg ctgcatctat ggcttctaac tttactcagt tcgttctcgt cgacaatggc   3960
ggaactggcg acgtgactgt cgccccaagc aacttcgcta acggggtcgc tgaatggatc   4020
agctctaact cgcgatcaca ggcttacaaa gtaacctgta gcgttcgtca gagctctgcg   4080
cagaatcgca aatacaccat caaagtcgag gtgcctaaag tggcaaccca gactgttggt   4140
ggtgaagagc ttcctgtagc cggatggaga tcttacttaa atatggaact aaccattcca   4200
attttcgcca cgaattccga ctgcgagctt attgttaagg caatgcaagg tctcctaaaa   4260
gatggaaacc cgattccctc ggccatcgca gcaaactccg gcatctacgg tggtggttca   4320
ggtggtggtt catctgcatc tatggcttct aactttactc agttcgttct cgtcgacaat   4380
ggcggaactg gcgacgtgac tgtcgcccca agcaacttcg ctaacggggt cgctgaatgg   4440
atcagctcta actcgcgatc acaggcttac aaagtaacct gtagcgttcg tcagagctct   4500
gcgcagaatc gcaaatacac catcaaagtc gaggtgccta aagtggcaac ccagactgtt   4560
ggtggtgaag agcttcctgt agccggatgg agatcttact taaatatgga actaaccatt   4620
ccaattttcg ccacgaattc cgactgcgag cttattgtta aggcaatgca aggtctccta   4680
aaagatggaa acccgattcc ctcagcaatc gcagcaaact ccggcatcta cggtggtggt   4740
tcaggtggtg gttcatctgc aggtatgatc agtctgattg cggcgttagc ggtagatcgc   4800
gttatcggca tggaaaacgc catgccgtgg aacctgcctg ccgatctcgc ctggtttaaa   4860
cgcaacacct aaataaacc cgtgattatg gccgccata cctgggaatc aatcggtcgt   4920
ccgttgccag gacgcaaaaa tattatcctc agcagtcaac cgggtacgga cgatcgcgta   4980
acgtgggtga gtcggtgga tgaagccatc gcggcgtgtg gtgacgtacc agaaatcatg   5040
gtgattggcg gcggtcgcgt ttatgaacag ttcttgccaa aagcgcaaaa actgtatctg   5100
acgcatatcg acgcagaagt ggaaggcgac acccatttcc cggattacga gccggatgac   5160
tgggaatcgg tattcagcga gttccacgat gctgatgcgc agaactctca cagctattgc   5220
tttgagattc tggagcggcg gaactcgagg gatccgagct cggtaccaag cttggcgtaa   5280
tcatggtcat agctgtttcc tgtgtgaaat tgttatccgc tcacaattcc acacaacata   5340
cgagccggaa gcataaagtg taaagcctgg ggtgcctaat gagtgagcta actcacatta   5400
attgcgttgc gctcactgcc cgctttccag tcgggaaacc tgtcgtgcca gctgcattaa   5460
tgaatcggcc aacgcgcggg gagaggcggt ttgcgtattg ggcgct            5506
```

```
<210> SEQ ID NO 9
<211> LENGTH: 1141
<212> TYPE: DNA
<213> ORGANISM: Artificial Sequence
<220> FEATURE:
<223> OTHER INFORMATION: Description of Artificial Sequence: Synthetic
      DNAI-fp1-rp1 polynucleotide
<220> FEATURE:
<221> NAME/KEY: promoter
<222> LOCATION: (1)..(17)
<220> FEATURE:
<221> NAME/KEY: RBS
<222> LOCATION: (51)..(56)
<220> FEATURE:
<221> NAME/KEY: CDS
<222> LOCATION: (65)..(1135)
<220> FEATURE:
<221> NAME/KEY: misc_feature
<222> LOCATION: (80)..(103)
<223> OTHER INFORMATION: Flag
<220> FEATURE:
<221> NAME/KEY: misc_feature
<222> LOCATION: (131)..(196)
```

<223> OTHER INFORMATION: Bap
<220> FEATURE:
<221> NAME/KEY: misc_feature
<222> LOCATION: (272)..(661)
<223> OTHER INFORMATION: Cvap
<220> FEATURE:
<221> NAME/KEY: misc_feature
<222> LOCATION: (695)..(1084)
<223> OTHER INFORMATION: Cvap
<220> FEATURE:
<221> NAME/KEY: misc_feature
<222> LOCATION: (1085)..(1135)
<223> OTHER INFORMATION: Spacer

<400> SEQUENCE: 9

```
taatacgact cactatagaa agtcgacaa taattttgtt taactttaag aaggagatat        60 acat atg gcc atg cag gcc gac tac aag gac gat gac gac aag ggc cag      109
     Met Ala Met Gln Ala Asp Tyr Lys Asp Asp Asp Asp Lys Gly Gln
     1               5                  10                  15 cta ggc cag tct agt gga ggt gga aat gct cgt act cgg cga cgt gaa      157
Leu Gly Gln Ser Ser Gly Gly Gly Asn Ala Arg Thr Arg Arg Arg Glu
                 20                  25                  30 cgc aga gcc atg gaa cga gct acg ctg cca caa gtg ctg gga ggt gga      205
Arg Arg Ala Met Glu Arg Ala Thr Leu Pro Gln Val Leu Gly Gly Gly
             35                  40                  45 tct ttc gaa cgc cag cac atg gac agc cca gat ctg ggt acc gac gac      253
Ser Phe Glu Arg Gln His Met Asp Ser Pro Asp Leu Gly Thr Asp Asp
         50                  55                  60 gac gac aag gct gca tct atg gct tct aac ttt act cag ttc gtt ctc      301
Asp Asp Lys Ala Ala Ser Met Ala Ser Asn Phe Thr Gln Phe Val Leu
     65                  70                  75 gtc gac aat ggc gga act ggc gac gtg act gtc gcc cca agc aac ttc      349
Val Asp Asn Gly Gly Thr Gly Asp Val Thr Val Ala Pro Ser Asn Phe
80                  85                  90                  95 gct aac ggg gtc gct gaa tgg atc agc tct aac tcg cga tca cag gct      397
Ala Asn Gly Val Ala Glu Trp Ile Ser Ser Asn Ser Arg Ser Gln Ala
                100                 105                 110 tac aaa gta acc tgt agc gtt cgt cag agc tct gcg cag aat cgc aaa      445
Tyr Lys Val Thr Cys Ser Val Arg Gln Ser Ser Ala Gln Asn Arg Lys
            115                 120                 125 tac acc atc aaa gtc gag gtg cct aaa gtg gca acc cag act gtt ggt      493
Tyr Thr Ile Lys Val Glu Val Pro Lys Val Ala Thr Gln Thr Val Gly
        130                 135                 140 ggt gaa gag ctt cct gta gcc gga tgg aga tct tac tta aat atg gaa      541
Gly Glu Glu Leu Pro Val Ala Gly Trp Arg Ser Tyr Leu Asn Met Glu
145                 150                 155 cta acc att cca att ttc gcc acg aat tcc gac tgc gag ctt att gtt      589
Leu Thr Ile Pro Ile Phe Ala Thr Asn Ser Asp Cys Glu Leu Ile Val
160                 165                 170                 175 aag gca atg caa ggt ctc cta aaa gat gga aac ccg att ccc tcg gcc      637
Lys Ala Met Gln Gly Leu Leu Lys Asp Gly Asn Pro Ile Pro Ser Ala
                180                 185                 190 atc gca gca aac tcc ggc atc tac ggt ggt ggt tca ggt ggt ggt tca      685
Ile Ala Ala Asn Ser Gly Ile Tyr Gly Gly Gly Ser Gly Gly Gly Ser
            195                 200                 205 tct gca tct atg gct tct aac ttt act cag ttc gtt ctc gtc gac aat      733
Ser Ala Ser Met Ala Ser Asn Phe Thr Gln Phe Val Leu Val Asp Asn
        210                 215                 220 ggc gga act ggc gac gtg act gtc gcc cca agc aac ttc gct aac ggg      781
Gly Gly Thr Gly Asp Val Thr Val Ala Pro Ser Asn Phe Ala Asn Gly
225                 230                 235 gtc gct gaa tgg atc agc tct aac tcg cga tca cag gct tac aaa gta      829
```

```
Val Ala Glu Trp Ile Ser Ser Asn Ser Arg Ser Gln Ala Tyr Lys Val
240                 245                 250                 255 acc tgt agc gtt cgt cag agc tct gcg cag aat cgc aaa tac acc atc      877
Thr Cys Ser Val Arg Gln Ser Ser Ala Gln Asn Arg Lys Tyr Thr Ile
                    260                 265                 270 aaa gtc gag gtg cct aaa gtg gca acc cag act gtt ggt ggt gaa gag      925
Lys Val Glu Val Pro Lys Val Ala Thr Gln Thr Val Gly Gly Glu Glu
                275                 280                 285 ctt cct gta gcc gga tgg aga tct tac tta aat atg gaa cta acc att      973
Leu Pro Val Ala Gly Trp Arg Ser Tyr Leu Asn Met Glu Leu Thr Ile
            290                 295                 300 cca att ttc gcc acg aat tcc gac tgc gag ctt att gtt aag gca atg     1021
Pro Ile Phe Ala Thr Asn Ser Asp Cys Glu Leu Ile Val Lys Ala Met
305                 310                 315 caa ggt ctc cta aaa gat gga aac ccg att ccc tca gca atc gca gca     1069
Gln Gly Leu Leu Lys Asp Gly Asn Pro Ile Pro Ser Ala Ile Ala Ala
320                 325                 330                 335 aac tcc ggc atc tac ggt ggt ggt tca ggt ggt ggt tca tct gca ggt     1117
Asn Ser Gly Ile Tyr Gly Gly Gly Ser Gly Gly Gly Ser Ser Ala Gly
                340                 345                 350 atg atc agt ctg att gcg taatga                                      1141
Met Ile Ser Leu Ile Ala
            355
```

```
<210> SEQ ID NO 10
<211> LENGTH: 357
<212> TYPE: PRT
<213> ORGANISM: Artificial Sequence
<220> FEATURE:
<223> OTHER INFORMATION: Description of Artificial Sequence: Synthetic
      DNAI-fp1-rp1 polypeptide

<400> SEQUENCE: 10

Met Ala Met Gln Ala Asp Tyr Lys Asp Asp Asp Lys Gly Gln Leu
1               5                   10                  15

Gly Gln Ser Ser Gly Gly Gly Asn Ala Arg Thr Arg Arg Glu Arg
                20                  25                  30

Arg Ala Met Glu Arg Ala Thr Leu Pro Gln Val Leu Gly Gly Gly Ser
            35                  40                  45

Phe Glu Arg Gln His Met Asp Ser Pro Asp Leu Gly Thr Asp Asp Asp
50                  55                  60

Asp Lys Ala Ala Ser Met Ala Ser Asn Phe Thr Gln Phe Val Leu Val
65                  70                  75                  80

Asp Asn Gly Gly Thr Gly Asp Val Thr Val Ala Pro Ser Asn Phe Ala
                85                  90                  95

Asn Gly Val Ala Glu Trp Ile Ser Ser Asn Ser Arg Ser Gln Ala Tyr
            100                 105                 110

Lys Val Thr Cys Ser Val Arg Gln Ser Ser Ala Gln Asn Arg Lys Tyr
        115                 120                 125

Thr Ile Lys Val Glu Val Pro Lys Val Ala Thr Gln Thr Val Gly Gly
    130                 135                 140

Glu Glu Leu Pro Val Ala Gly Trp Arg Ser Tyr Leu Asn Met Glu Leu
145                 150                 155                 160

Thr Ile Pro Ile Phe Ala Thr Asn Ser Asp Cys Glu Leu Ile Val Lys
                165                 170                 175

Ala Met Gln Gly Leu Leu Lys Asp Gly Asn Pro Ile Pro Ser Ala Ile
            180                 185                 190

Ala Ala Asn Ser Gly Ile Tyr Gly Gly Gly Ser Gly Gly Gly Ser Ser
```

195                 200                 205

Ala Ser Met Ala Ser Asn Phe Thr Gln Phe Val Leu Val Asp Asn Gly
    210                 215                 220

Gly Thr Gly Asp Val Thr Val Ala Pro Ser Asn Phe Ala Asn Gly Val
225                 230                 235                 240

Ala Glu Trp Ile Ser Ser Asn Ser Arg Ser Gln Ala Tyr Lys Val Thr
                245                 250                 255

Cys Ser Val Arg Gln Ser Ser Ala Gln Asn Arg Lys Tyr Thr Ile Lys
            260                 265                 270

Val Glu Val Pro Lys Val Ala Thr Gln Thr Val Gly Gly Glu Glu Leu
        275                 280                 285

Pro Val Ala Gly Trp Arg Ser Tyr Leu Asn Met Glu Leu Thr Ile Pro
    290                 295                 300

Ile Phe Ala Thr Asn Ser Asp Cys Glu Leu Ile Val Lys Ala Met Gln
305                 310                 315                 320

Gly Leu Leu Lys Asp Gly Asn Pro Ile Pro Ser Ala Ile Ala Ala Asn
                325                 330                 335

Ser Gly Ile Tyr Gly Gly Gly Ser Gly Gly Ser Ser Ala Gly Met
            340                 345                 350

Ile Ser Leu Ile Ala
        355

<210> SEQ ID NO 11
<211> LENGTH: 1159
<212> TYPE: DNA
<213> ORGANISM: Artificial Sequence
<220> FEATURE:
<223> OTHER INFORMATION: Description of Artificial Sequence: Synthetic
      DNAI-fp2-rp1 polynucleotide
<220> FEATURE:
<221> NAME/KEY: promoter
<222> LOCATION: (1)..(17)
<220> FEATURE:
<221> NAME/KEY: misc_feature
<222> LOCATION: (21)..(35)
<223> OTHER INFORMATION: boxB
<220> FEATURE:
<221> NAME/KEY: RBS
<222> LOCATION: (69)..(74)
<220> FEATURE:
<221> NAME/KEY: CDS
<222> LOCATION: (83)..(1153)
<220> FEATURE:
<221> NAME/KEY: misc_feature
<222> LOCATION: (98)..(121)
<223> OTHER INFORMATION: Flag
<220> FEATURE:
<221> NAME/KEY: misc_feature
<222> LOCATION: (149)..(214)
<223> OTHER INFORMATION: Bap
<220> FEATURE:
<221> NAME/KEY: misc_feature
<222> LOCATION: (290)..(679)
<223> OTHER INFORMATION: Cvap
<220> FEATURE:
<221> NAME/KEY: misc_feature
<222> LOCATION: (713)..(1102)
<223> OTHER INFORMATION: Cvap
<220> FEATURE:
<221> NAME/KEY: misc_feature
<222> LOCATION: (1103)..(1153)
<223> OTHER INFORMATION: Spacer

<400> SEQUENCE: 11
taatacgact cactatagag gccctgaaaa agggccaaaa gtcgacaata attttgttta    60
actttaagaa ggagatatac at atg gcc atg cag gcc gac tac aag gac gat   112

```
                  Met Ala Met Gln Ala Asp Tyr Lys Asp Asp
                   1               5                  10 gac gac aag ggc cag cta ggc cag tct agt gga ggt gga aat gct cgt        160
Asp Asp Lys Gly Gln Leu Gly Gln Ser Ser Gly Gly Gly Asn Ala Arg
             15                  20                  25 act cgg cga cgt gaa cgc aga gcc atg gaa cga gct acg ctg cca caa        208
Thr Arg Arg Arg Glu Arg Arg Ala Met Glu Arg Ala Thr Leu Pro Gln
         30                  35                  40 gtg ctg gga ggt gga tct ttc gaa cgc cag cac atg gac agc cca gat        256
Val Leu Gly Gly Gly Ser Phe Glu Arg Gln His Met Asp Ser Pro Asp
             45                  50                  55 ctg ggt acc gac gac gac gac aag gct gca tct atg gct tct aac ttt        304
Leu Gly Thr Asp Asp Asp Asp Lys Ala Ala Ser Met Ala Ser Asn Phe
         60                  65                  70 act cag ttc gtt ctc gtc gac aat ggc gga act ggc gac gtg act gtc        352
Thr Gln Phe Val Leu Val Asp Asn Gly Gly Thr Gly Asp Val Thr Val
 75                  80                  85                  90 gcc cca agc aac ttc gct aac ggg gtc gct gaa tgg atc agc tct aac        400
Ala Pro Ser Asn Phe Ala Asn Gly Val Ala Glu Trp Ile Ser Ser Asn
                 95                 100                 105 tcg cga tca cag gct tac aaa gta acc tgt agc gtt cgt cag agc tct        448
Ser Arg Ser Gln Ala Tyr Lys Val Thr Cys Ser Val Arg Gln Ser Ser
             110                 115                 120 gcg cag aat cgc aaa tac acc atc aaa gtc gag gtg cct aaa gtg gca        496
Ala Gln Asn Arg Lys Tyr Thr Ile Lys Val Glu Val Pro Lys Val Ala
         125                 130                 135 acc cag act gtt ggt ggt gaa gag ctt cct gta gcc gga tgg aga tct        544
Thr Gln Thr Val Gly Gly Glu Glu Leu Pro Val Ala Gly Trp Arg Ser
     140                 145                 150 tac tta aat atg gaa cta acc att cca att ttc gcc acg aat tcc gac        592
Tyr Leu Asn Met Glu Leu Thr Ile Pro Ile Phe Ala Thr Asn Ser Asp
155                 160                 165                 170 tgc gag ctt att gtt aag gca atg caa ggt ctc cta aaa gat gga aac        640
Cys Glu Leu Ile Val Lys Ala Met Gln Gly Leu Leu Lys Asp Gly Asn
                 175                 180                 185 ccg att ccc tcg gcc atc gca gca aac tcc ggc atc tac ggt ggt ggt        688
Pro Ile Pro Ser Ala Ile Ala Ala Asn Ser Gly Ile Tyr Gly Gly Gly
             190                 195                 200 tca ggt ggt ggt tca tct gca tct atg gct tct aac ttt act cag ttc        736
Ser Gly Gly Gly Ser Ser Ala Ser Met Ala Ser Asn Phe Thr Gln Phe
         205                 210                 215 gtt ctc gtc gac aat ggc gga act ggc gac gtg act gtc gcc cca agc        784
Val Leu Val Asp Asn Gly Gly Thr Gly Asp Val Thr Val Ala Pro Ser
     220                 225                 230 aac ttc gct aac ggg gtc gct gaa tgg atc agc tct aac tcg cga tca        832
Asn Phe Ala Asn Gly Val Ala Glu Trp Ile Ser Ser Asn Ser Arg Ser
235                 240                 245                 250 cag gct tac aaa gta acc tgt agc gtt cgt cag agc tct gcg cag aat        880
Gln Ala Tyr Lys Val Thr Cys Ser Val Arg Gln Ser Ser Ala Gln Asn
                 255                 260                 265 cgc aaa tac acc atc aaa gtc gag gtg cct aaa gtg gca acc cag act        928
Arg Lys Tyr Thr Ile Lys Val Glu Val Pro Lys Val Ala Thr Gln Thr
             270                 275                 280 gtt ggt ggt gaa gag ctt cct gta gcc gga tgg aga tct tac tta aat        976
Val Gly Gly Glu Glu Leu Pro Val Ala Gly Trp Arg Ser Tyr Leu Asn
         285                 290                 295 atg gaa cta acc att cca att ttc gcc acg aat tcc gac tgc gag ctt       1024
Met Glu Leu Thr Ile Pro Ile Phe Ala Thr Asn Ser Asp Cys Glu Leu
     300                 305                 310
```

```
att gtt aag gca atg caa ggt ctc cta aaa gat gga aac ccg att ccc    1072
Ile Val Lys Ala Met Gln Gly Leu Leu Lys Asp Gly Asn Pro Ile Pro
315                 320                 325                 330 tca gca atc gca gca aac tcc ggc atc tac ggt ggt ggt tca ggt ggt    1120
Ser Ala Ile Ala Ala Asn Ser Gly Ile Tyr Gly Gly Gly Ser Gly Gly
            335                 340                 345 ggt tca tct gca ggt atg atc agt ctg att gcg taatga                 1159
Gly Ser Ser Ala Gly Met Ile Ser Leu Ile Ala
        350                 355
```

<210> SEQ ID NO 12
<211> LENGTH: 357
<212> TYPE: PRT
<213> ORGANISM: Artificial Sequence
<220> FEATURE:
<223> OTHER INFORMATION: Description of Artificial Sequence: Synthetic
      DNAI-fp2-rp1 polypeptide

<400> SEQUENCE: 12

```
Met Ala Met Gln Ala Asp Tyr Lys Asp Asp Asp Lys Gly Gln Leu
1               5                   10                  15

Gly Gln Ser Ser Gly Gly Gly Asn Ala Arg Thr Arg Arg Glu Arg
                20                  25                  30

Arg Ala Met Glu Arg Ala Thr Leu Pro Gln Val Leu Gly Gly Ser
            35                  40                  45

Phe Glu Arg Gln His Met Asp Ser Pro Asp Leu Gly Thr Asp Asp
50                  55                  60

Asp Lys Ala Ala Ser Met Ala Ser Asn Phe Thr Gln Phe Val Leu Val
65                  70                  75                  80

Asp Asn Gly Gly Thr Gly Asp Val Thr Val Ala Pro Ser Asn Phe Ala
                85                  90                  95

Asn Gly Val Ala Glu Trp Ile Ser Ser Asn Ser Arg Ser Gln Ala Tyr
            100                 105                 110

Lys Val Thr Cys Ser Val Arg Gln Ser Ser Ala Gln Asn Arg Lys Tyr
        115                 120                 125

Thr Ile Lys Val Glu Val Pro Lys Val Ala Thr Gln Thr Val Gly Gly
    130                 135                 140

Glu Glu Leu Pro Val Ala Gly Trp Arg Ser Tyr Leu Asn Met Glu Leu
145                 150                 155                 160

Thr Ile Pro Ile Phe Ala Thr Asn Ser Asp Cys Glu Leu Ile Val Lys
                165                 170                 175

Ala Met Gln Gly Leu Leu Lys Asp Gly Asn Pro Ile Pro Ser Ala Ile
            180                 185                 190

Ala Ala Asn Ser Gly Ile Tyr Gly Gly Gly Ser Gly Gly Gly Ser Ser
        195                 200                 205

Ala Ser Met Ala Ser Asn Phe Thr Gln Phe Val Leu Val Asp Asn Gly
    210                 215                 220

Gly Thr Gly Asp Val Thr Val Ala Pro Ser Asn Phe Ala Asn Gly Val
225                 230                 235                 240

Ala Glu Trp Ile Ser Ser Asn Ser Arg Ser Gln Ala Tyr Lys Val Thr
                245                 250                 255

Cys Ser Val Arg Gln Ser Ser Ala Gln Asn Arg Lys Tyr Thr Ile Lys
            260                 265                 270

Val Glu Val Pro Lys Val Ala Thr Gln Thr Val Gly Gly Glu Glu Leu
        275                 280                 285

Pro Val Ala Gly Trp Arg Ser Tyr Leu Asn Met Glu Leu Thr Ile Pro
    290                 295                 300
```

```
Ile Phe Ala Thr Asn Ser Asp Cys Glu Leu Ile Val Lys Ala Met Gln
305                 310                 315                 320

Gly Leu Leu Lys Asp Gly Asn Pro Ile Pro Ser Ala Ile Ala Ala Asn
            325                 330                 335

Ser Gly Ile Tyr Gly Gly Gly Ser Gly Gly Gly Ser Ser Ala Gly Met
        340                 345                 350

Ile Ser Leu Ile Ala
        355

<210> SEQ ID NO 13
<211> LENGTH: 1161
<212> TYPE: DNA
<213> ORGANISM: Artificial Sequence
<220> FEATURE:
<223> OTHER INFORMATION: Description of Artificial Sequence: Synthetic
      DNAI-fp3-rp1 polynucleotide
<220> FEATURE:
<221> NAME/KEY: promoter
<222> LOCATION: (1)..(17)
<220> FEATURE:
<221> NAME/KEY: misc_feature
<222> LOCATION: (20)..(38)
<223> OTHER INFORMATION: Cv
<220> FEATURE:
<221> NAME/KEY: RBS
<222> LOCATION: (71)..(76)
<220> FEATURE:
<221> NAME/KEY: CDS
<222> LOCATION: (85)..(1155)
<220> FEATURE:
<221> NAME/KEY: misc_feature
<222> LOCATION: (100)..(123)
<223> OTHER INFORMATION: Flag
<220> FEATURE:
<221> NAME/KEY: misc_feature
<222> LOCATION: (151)..(216)
<223> OTHER INFORMATION: Bap
<220> FEATURE:
<221> NAME/KEY: misc_feature
<222> LOCATION: (292)..(681)
<223> OTHER INFORMATION: Cvap
<220> FEATURE:
<221> NAME/KEY: misc_feature
<222> LOCATION: (715)..(1104)
<223> OTHER INFORMATION: Cvap
<220> FEATURE:
<221> NAME/KEY: misc_feature
<222> LOCATION: (1105)..(1155)
<223> OTHER INFORMATION: Spacer

<400> SEQUENCE: 13
taatacgact cactatagaa catgaggatc acccatgtaa aagtcgacaa taattttgtt      60
taactttaag aaggagatat acat atg gcc atg cag gcc gac tac aag gac       111
                          Met Ala Met Gln Ala Asp Tyr Lys Asp
                            1               5 gat gac gac aag ggc cag cta ggc cag tct agt gga ggt gga aat gct      159
Asp Asp Asp Lys Gly Gln Leu Gly Gln Ser Ser Gly Gly Gly Asn Ala
 10              15                  20                  25 cgt act cgg cga cgt gaa cgc aga gcc atg gaa cga gct acg ctg cca      207
Arg Thr Arg Arg Arg Glu Arg Arg Ala Met Glu Arg Ala Thr Leu Pro
             30                  35                  40 caa gtg ctg gga ggt gga tct ttc gaa cgc cag cac atg gac agc cca      255
Gln Val Leu Gly Gly Gly Ser Phe Glu Arg Gln His Met Asp Ser Pro
         45                  50                  55 gat ctg ggt acc gac gac gac gac aag gct gca tct atg gct tct aac      303
Asp Leu Gly Thr Asp Asp Asp Asp Lys Ala Ala Ser Met Ala Ser Asn
     60                  65                  70
```

```
ttt act cag ttc gtt ctc gtc gac aat ggc gga act ggc gac gtg act      351
Phe Thr Gln Phe Val Leu Val Asp Asn Gly Gly Thr Gly Asp Val Thr
 75                  80                  85 gtc gcc cca agc aac ttc gct aac ggg gtc gct gaa tgg atc agc tct      399
Val Ala Pro Ser Asn Phe Ala Asn Gly Val Ala Glu Trp Ile Ser Ser
 90                  95                 100                 105 aac tcg cga tca cag gct tac aaa gta acc tgt agc gtt cgt cag agc      447
Asn Ser Arg Ser Gln Ala Tyr Lys Val Thr Cys Ser Val Arg Gln Ser
                110                 115                 120 tct gcg cag aat cgc aaa tac acc atc aaa gtc gag gtg cct aaa gtg      495
Ser Ala Gln Asn Arg Lys Tyr Thr Ile Lys Val Glu Val Pro Lys Val
            125                 130                 135 gca acc cag act gtt ggt ggt gaa gag ctt cct gta gcc gga tgg aga      543
Ala Thr Gln Thr Val Gly Gly Glu Glu Leu Pro Val Ala Gly Trp Arg
            140                 145                 150 tct tac tta aat atg gaa cta acc att cca att ttc gcc acg aat tcc      591
Ser Tyr Leu Asn Met Glu Leu Thr Ile Pro Ile Phe Ala Thr Asn Ser
155                 160                 165 gac tgc gag ctt att gtt aag gca atg caa ggt ctc cta aaa gat gga      639
Asp Cys Glu Leu Ile Val Lys Ala Met Gln Gly Leu Leu Lys Asp Gly
170                 175                 180                 185 aac ccg att ccc tcg gcc atc gca gca aac tcc ggc atc tac ggt ggt      687
Asn Pro Ile Pro Ser Ala Ile Ala Ala Asn Ser Gly Ile Tyr Gly Gly
                190                 195                 200 ggt tca ggt ggt ggt tca tct gca tct atg gct tct aac ttt act cag      735
Gly Ser Gly Gly Gly Ser Ser Ala Ser Met Ala Ser Asn Phe Thr Gln
            205                 210                 215 ttc gtt ctc gtc gac aat ggc gga act ggc gac gtg act gtc gcc cca      783
Phe Val Leu Val Asp Asn Gly Gly Thr Gly Asp Val Thr Val Ala Pro
            220                 225                 230 agc aac ttc gct aac ggg gtc gct gaa tgg atc agc tct aac tcg cga      831
Ser Asn Phe Ala Asn Gly Val Ala Glu Trp Ile Ser Ser Asn Ser Arg
235                 240                 245 tca cag gct tac aaa gta acc tgt agc gtt cgt cag agc tct gcg cag      879
Ser Gln Ala Tyr Lys Val Thr Cys Ser Val Arg Gln Ser Ser Ala Gln
250                 255                 260                 265 aat cgc aaa tac acc atc aaa gtc gag gtg cct aaa gtg gca acc cag      927
Asn Arg Lys Tyr Thr Ile Lys Val Glu Val Pro Lys Val Ala Thr Gln
                270                 275                 280 act gtt ggt ggt gaa gag ctt cct gta gcc gga tgg aga tct tac tta      975
Thr Val Gly Gly Glu Glu Leu Pro Val Ala Gly Trp Arg Ser Tyr Leu
            285                 290                 295 aat atg gaa cta acc att cca att ttc gcc acg aat tcc gac tgc gag     1023
Asn Met Glu Leu Thr Ile Pro Ile Phe Ala Thr Asn Ser Asp Cys Glu
            300                 305                 310 ctt att gtt aag gca atg caa ggt ctc cta aaa gat gga aac ccg att     1071
Leu Ile Val Lys Ala Met Gln Gly Leu Leu Lys Asp Gly Asn Pro Ile
315                 320                 325 ccc tca gca atc gca gca aac tcc ggc atc tac ggt ggt ggt tca ggt     1119
Pro Ser Ala Ile Ala Ala Asn Ser Gly Ile Tyr Gly Gly Gly Ser Gly
330                 335                 340                 345 ggt ggt tca tct gca ggt atg atc agt ctg att gcg taatga              1161
Gly Gly Ser Ser Ala Gly Met Ile Ser Leu Ile Ala
            350                 355
```

<210> SEQ ID NO 14
<211> LENGTH: 357
<212> TYPE: PRT
<213> ORGANISM: Artificial Sequence
<220> FEATURE:
<223> OTHER INFORMATION: Description of Artificial Sequence: Synthetic DNAI-fp3-rp1 polypeptide

<400> SEQUENCE: 14

Met Ala Met Gln Ala Asp Tyr Lys Asp Asp Asp Lys Gly Gln Leu
1               5                   10                  15

Gly Gln Ser Ser Gly Gly Gly Asn Ala Arg Thr Arg Arg Glu Arg
            20                  25                  30

Arg Ala Met Glu Arg Ala Thr Leu Pro Gln Val Leu Gly Gly Ser
        35                  40                  45

Phe Glu Arg Gln His Met Asp Ser Pro Asp Leu Gly Thr Asp Asp
50                  55                  60

Asp Lys Ala Ala Ser Met Ala Ser Asn Phe Thr Gln Phe Val Leu Val
65                  70                  75                  80

Asp Asn Gly Gly Thr Gly Asp Val Thr Val Ala Pro Ser Asn Phe Ala
                    85                  90                  95

Asn Gly Val Ala Glu Trp Ile Ser Ser Asn Ser Arg Ser Gln Ala Tyr
                100                 105                 110

Lys Val Thr Cys Ser Val Arg Gln Ser Ser Ala Gln Asn Arg Lys Tyr
            115                 120                 125

Thr Ile Lys Val Glu Val Pro Lys Val Ala Thr Gln Thr Val Gly Gly
130                 135                 140

Glu Glu Leu Pro Val Ala Gly Trp Arg Ser Tyr Leu Asn Met Glu Leu
145                 150                 155                 160

Thr Ile Pro Ile Phe Ala Thr Asn Ser Asp Cys Glu Leu Ile Val Lys
                165                 170                 175

Ala Met Gln Gly Leu Leu Lys Asp Gly Asn Pro Ile Pro Ser Ala Ile
                180                 185                 190

Ala Ala Asn Ser Gly Ile Tyr Gly Gly Ser Gly Gly Gly Ser Ser
            195                 200                 205

Ala Ser Met Ala Ser Asn Phe Thr Gln Phe Val Leu Val Asp Asn Gly
210                 215                 220

Gly Thr Gly Asp Val Thr Val Ala Pro Ser Asn Phe Ala Asn Gly Val
225                 230                 235                 240

Ala Glu Trp Ile Ser Ser Asn Ser Arg Ser Gln Ala Tyr Lys Val Thr
                245                 250                 255

Cys Ser Val Arg Gln Ser Ser Ala Gln Asn Arg Lys Tyr Thr Ile Lys
                260                 265                 270

Val Glu Val Pro Lys Val Ala Thr Gln Thr Val Gly Gly Glu Glu Leu
            275                 280                 285

Pro Val Ala Gly Trp Arg Ser Tyr Leu Asn Met Glu Leu Thr Ile Pro
290                 295                 300

Ile Phe Ala Thr Asn Ser Asp Cys Glu Leu Ile Val Lys Ala Met Gln
305                 310                 315                 320

Gly Leu Leu Lys Asp Gly Asn Pro Ile Pro Ser Ala Ile Ala Ala Asn
                325                 330                 335

Ser Gly Ile Tyr Gly Gly Gly Ser Gly Gly Gly Ser Ser Ala Gly Met
                340                 345                 350

Ile Ser Leu Ile Ala
        355

<210> SEQ ID NO 15
<211> LENGTH: 1182
<212> TYPE: DNA
<213> ORGANISM: Artificial Sequence
<220> FEATURE:

```
<223> OTHER INFORMATION: Description of Artificial Sequence: Synthetic
      DNAII-fp4-rp1 polynucleotide
<220> FEATURE:
<221> NAME/KEY: promoter
<222> LOCATION: (1)..(17)
<220> FEATURE:
<221> NAME/KEY: misc_feature
<222> LOCATION: (20)..(35)
<223> OTHER INFORMATION: boxB
<220> FEATURE:
<221> NAME/KEY: misc_feature
<222> LOCATION: (41)..(59)
<223> OTHER INFORMATION: Cv
<220> FEATURE:
<221> NAME/KEY: RBS
<222> LOCATION: (92)..(97)
<220> FEATURE:
<221> NAME/KEY: CDS
<222> LOCATION: (106)..(1176)
<220> FEATURE:
<221> NAME/KEY: misc_feature
<222> LOCATION: (121)..(144)
<223> OTHER INFORMATION: Flag
<220> FEATURE:
<221> NAME/KEY: misc_feature
<222> LOCATION: (172)..(237)
<223> OTHER INFORMATION: Bap
<220> FEATURE:
<221> NAME/KEY: misc_feature
<222> LOCATION: (313)..(702)
<223> OTHER INFORMATION: Cvap
<220> FEATURE:
<221> NAME/KEY: misc_feature
<222> LOCATION: (736)..(1125)
<223> OTHER INFORMATION: Cvap
<220> FEATURE:
<221> NAME/KEY: misc_feature
<222> LOCATION: (1126)..(1176)
<223> OTHER INFORMATION: Spacer

<400> SEQUENCE: 15
taatacgact cactatagag gccctgaaaa agggccaaaa acatgaggat cacccatgta      60
aaagtcgaca ataattttgt ttaactttaa gaaggagata tacat atg gcc atg cag    117
                                                 Met Ala Met Gln
                                                  1 gcc gac tac aag gac gat gac gac aag ggc cag cta ggc cag tct agt      165
Ala Asp Tyr Lys Asp Asp Asp Asp Lys Gly Gln Leu Gly Gln Ser Ser
 5                  10                  15                  20 gga ggt gga aat gct cgt act cgg cga cgt gaa cgc aga gcc atg gaa      213
Gly Gly Gly Asn Ala Arg Thr Arg Arg Arg Glu Arg Arg Ala Met Glu
                 25                  30                  35 cga gct acg ctg cca caa gtg ctg gga ggt gga tct ttc gaa cgc cag      261
Arg Ala Thr Leu Pro Gln Val Leu Gly Gly Gly Ser Phe Glu Arg Gln
             40                  45                  50 cac atg gac agc cca gat ctg ggt acc gac gac gac gac aag gct gca      309
His Met Asp Ser Pro Asp Leu Gly Thr Asp Asp Asp Asp Lys Ala Ala
         55                  60                  65 tct atg gct tct aac ttt act cag ttc gtt ctc gtc gac aat ggc gga      357
Ser Met Ala Ser Asn Phe Thr Gln Phe Val Leu Val Asp Asn Gly Gly
     70                  75                  80 act ggc gac gtg act gtc gcc cca agc aac ttc gct aac ggg gtc gct      405
Thr Gly Asp Val Thr Val Ala Pro Ser Asn Phe Ala Asn Gly Val Ala
 85                  90                  95                 100 gaa tgg atc agc tct aac tcg cga tca cag gct tac aaa gta acc tgt      453
Glu Trp Ile Ser Ser Asn Ser Arg Ser Gln Ala Tyr Lys Val Thr Cys
                105                 110                 115 agc gtt cgt cag agc tct gcg cag aat cgc aaa tac acc atc aaa gtc      501
Ser Val Arg Gln Ser Ser Ala Gln Asn Arg Lys Tyr Thr Ile Lys Val
            120                 125                 130
```

```
gag gtg cct aaa gtg gca acc cag act gtt ggt ggt gaa gag ctt cct        549
Glu Val Pro Lys Val Ala Thr Gln Thr Val Gly Gly Glu Glu Leu Pro
        135                 140                 145 gta gcc gga tgg aga tct tac tta aat atg gaa cta acc att cca att        597
Val Ala Gly Trp Arg Ser Tyr Leu Asn Met Glu Leu Thr Ile Pro Ile
    150                 155                 160 ttc gcc acg aat tcc gac tgc gag ctt att gtt aag gca atg caa ggt        645
Phe Ala Thr Asn Ser Asp Cys Glu Leu Ile Val Lys Ala Met Gln Gly
165                 170                 175                 180 ctc cta aaa gat gga aac ccg att ccc tcg gcc atc gca gca aac tcc        693
Leu Leu Lys Asp Gly Asn Pro Ile Pro Ser Ala Ile Ala Ala Asn Ser
                185                 190                 195 ggc atc tac ggt ggt ggt tca ggt ggt ggt tca tct gca tct atg gct        741
Gly Ile Tyr Gly Gly Gly Ser Gly Gly Gly Ser Ser Ala Ser Met Ala
            200                 205                 210 tct aac ttt act cag ttc gtt ctc gtc gac aat ggc gga act ggc gac        789
Ser Asn Phe Thr Gln Phe Val Leu Val Asp Asn Gly Gly Thr Gly Asp
        215                 220                 225 gtg act gtc gcc cca agc aac ttc gct aac ggg gtc gct gaa tgg atc        837
Val Thr Val Ala Pro Ser Asn Phe Ala Asn Gly Val Ala Glu Trp Ile
    230                 235                 240 agc tct aac tcg cga tca cag gct tac aaa gta acc tgt agc gtt cgt        885
Ser Ser Asn Ser Arg Ser Gln Ala Tyr Lys Val Thr Cys Ser Val Arg
245                 250                 255                 260 cag agc tct gcg cag aat cgc aaa tac acc atc aaa gtc gag gtg cct        933
Gln Ser Ser Ala Gln Asn Arg Lys Tyr Thr Ile Lys Val Glu Val Pro
                265                 270                 275 aaa gtg gca acc cag act gtt ggt ggt gaa gag ctt cct gta gcc gga        981
Lys Val Ala Thr Gln Thr Val Gly Gly Glu Glu Leu Pro Val Ala Gly
            280                 285                 290 tgg aga tct tac tta aat atg gaa cta acc att cca att ttc gcc acg       1029
Trp Arg Ser Tyr Leu Asn Met Glu Leu Thr Ile Pro Ile Phe Ala Thr
        295                 300                 305 aat tcc gac tgc gag ctt att gtt aag gca atg caa ggt ctc cta aaa       1077
Asn Ser Asp Cys Glu Leu Ile Val Lys Ala Met Gln Gly Leu Leu Lys
    310                 315                 320 gat gga aac ccg att ccc tca gca atc gca gca aac tcc ggc atc tac       1125
Asp Gly Asn Pro Ile Pro Ser Ala Ile Ala Ala Asn Ser Gly Ile Tyr
325                 330                 335                 340 ggt ggt ggt tca ggt ggt ggt tca tct gca ggt atg atc agt ctg att       1173
Gly Gly Gly Ser Gly Gly Gly Ser Ser Ala Gly Met Ile Ser Leu Ile
                345                 350                 355 gcg taatga                                                             1182
Ala

<210> SEQ ID NO 16
<211> LENGTH: 357
<212> TYPE: PRT
<213> ORGANISM: Artificial Sequence
<220> FEATURE:
<223> OTHER INFORMATION: Description of Artificial Sequence: Synthetic
      DNAII-fp4-rp1 polypeptide

<400> SEQUENCE: 16

Met Ala Met Gln Ala Asp Tyr Lys Asp Asp Asp Lys Gly Gln Leu
1               5                   10                  15

Gly Gln Ser Ser Gly Gly Gly Asn Ala Arg Thr Arg Arg Glu Arg
            20                  25                  30

Arg Ala Met Glu Arg Ala Thr Leu Pro Gln Val Leu Gly Gly Ser
        35                  40                  45
```

```
Phe Glu Arg Gln His Met Asp Ser Pro Asp Leu Gly Thr Asp Asp
 50                  55                  60

Asp Lys Ala Ala Ser Met Ala Ser Asn Phe Thr Gln Phe Val Leu Val
 65                  70                  75                  80

Asp Asn Gly Gly Thr Gly Asp Val Thr Val Ala Pro Ser Asn Phe Ala
                 85                  90                  95

Asn Gly Val Ala Glu Trp Ile Ser Ser Asn Ser Arg Ser Gln Ala Tyr
             100                 105                 110

Lys Val Thr Cys Ser Val Arg Gln Ser Ser Ala Gln Asn Arg Lys Tyr
         115                 120                 125

Thr Ile Lys Val Glu Val Pro Lys Val Ala Thr Gln Thr Val Gly Gly
     130                 135                 140

Glu Glu Leu Pro Val Ala Gly Trp Arg Ser Tyr Leu Asn Met Glu Leu
145                 150                 155                 160

Thr Ile Pro Ile Phe Ala Thr Asn Ser Asp Cys Glu Leu Ile Val Lys
                165                 170                 175

Ala Met Gln Gly Leu Leu Lys Asp Gly Asn Pro Ile Pro Ser Ala Ile
            180                 185                 190

Ala Ala Asn Ser Gly Ile Tyr Gly Gly Gly Ser Gly Gly Gly Ser Ser
        195                 200                 205

Ala Ser Met Ala Ser Asn Phe Thr Gln Phe Val Leu Val Asp Asn Gly
    210                 215                 220

Gly Thr Gly Asp Val Thr Val Ala Pro Ser Asn Phe Ala Asn Gly Val
225                 230                 235                 240

Ala Glu Trp Ile Ser Ser Asn Ser Arg Ser Gln Ala Tyr Lys Val Thr
                245                 250                 255

Cys Ser Val Arg Gln Ser Ser Ala Gln Asn Arg Lys Tyr Thr Ile Lys
            260                 265                 270

Val Glu Val Pro Lys Val Ala Thr Gln Thr Val Gly Gly Glu Glu Leu
        275                 280                 285

Pro Val Ala Gly Trp Arg Ser Tyr Leu Asn Met Glu Leu Thr Ile Pro
    290                 295                 300

Ile Phe Ala Thr Asn Ser Asp Cys Glu Leu Ile Val Lys Ala Met Gln
305                 310                 315                 320

Gly Leu Leu Lys Asp Gly Asn Pro Ile Pro Ser Ala Ile Ala Ala Asn
                325                 330                 335

Ser Gly Ile Tyr Gly Gly Gly Ser Gly Gly Gly Ser Ser Ala Gly Met
            340                 345                 350

Ile Ser Leu Ile Ala
        355

<210> SEQ ID NO 17
<211> LENGTH: 5500
<212> TYPE: DNA
<213> ORGANISM: Artificial Sequence
<220> FEATURE:
<223> OTHER INFORMATION: Description of Artificial Sequence: Synthetic
      plasmid DNAII-H6 full polynucleotide
<220> FEATURE:
<221> NAME/KEY: CDS
<222> LOCATION: (3712)..(4776)

<400> SEQUENCE: 17
cttccgcttc ctcgctcact gactcgctgc gctcggtcgt tcggctgcgg cgagcggtat     60
cagctcactc aaaggcggta atacggttat ccacagaatc aggggataac gcaggaaaga    120
```

```
acatgtgagc aaaaggccag caaaaggcca ggaaccgtaa aaaggccgcg ttgctggcgt    180
ttttccatag gctccgcccc cctgacgagc atcacaaaaa tcgacgctca agtcagaggt    240
ggcgaaaccc gacaggacta taaagatacc aggcgtttcc ccctggaagc tccctcgtgc    300
gctctcctgt tccgaccctg ccgcttaccg gatacctgtc cgcctttctc ccttcgggaa    360
gcgtggcgct ttctcatagc tcacgctgta ggtatctcag ttcggtgtag gtcgttcgct    420
ccaagctggg ctgtgtgcac gaaccccccg ttcagcccga ccgctgcgcc ttatccggta    480
actatcgtct tgagtccaac ccggtaagac acgacttatc gccactggca gcagccactg    540
gtaacaggat tagcagagcg aggtatgtag gcggtgctac agagttcttg aagtggtggc    600
ctaactacgg ctacactaga agaacagtat ttggtatctg cgctctgctg aagccagtta    660
ccttcggaaa aagagttggt agctcttgat ccggcaaaca aaccaccgct ggtagcggtg    720
gtttttttgt ttgcaagcag cagattacgc gcagaaaaaa aggatctcaa gaagatcctt    780
tgatcttttc tacggggtct gacgctcagt ggaacgaaaa ctcacgttaa gggattttgg    840
tcatgagatt atcaaaaagg atcttcacct agatcctttt aaattaaaaa tgaagtttta    900
aatcaatcta agtatatat gagtaaactt ggtctgacag ttaccaatgc ttaatcagtg    960
aggcacctat ctcagcgatc tgtctatttc gttcatccat agttgcctga ctccccgtcg   1020
tgtagataac tacgatacgg gagggcttac catctggccc cagtgctgca atgataccgc   1080
gagacccacg ctcaccggct ccagatttat cagcaataaa ccagccagcc ggaagggccg   1140
agcgcagaag tggtcctgca actttatccg cctccatcca gtctattaat tgttgccggg   1200
aagctagagt aagtagttcg ccagttaata gtttgcgcaa cgttgttgcc attgctacag   1260
gcatcgtggt gtcacgctcg tcgtttggta tggcttcatt cagctccggt tcccaacgat   1320
caaggcgagt tacatgatcc cccatgttgt gcaaaaaagc ggttagctcc ttcggtcctc   1380
cgatcgttgt cagaagtaag ttggccgcag tgttatcact catggttatg gcagcactgc   1440
ataattctct tactgtcatg ccatccgtaa gatgcttttc tgtgactggt gagtactcaa   1500
ccaagtcatt ctgagaatag tgtatgcggc gaccgagttg ctcttgcccg gcgtcaatac   1560
gggataatac cgcgccacat agcagaactt taaaagtgct catcattgga aaacgttctt   1620
cggggcgaaa actctcaagg atcttaccgc tgttgagatc cagttcgatg taacccactc   1680
gtgcacccaa ctgatcttca gcatctttta ctttcaccag cgtttctggg tgagcaaaaa   1740
caggaaggca aaatgccgca aaaaagggaa taagggcgac acggaaatgt tgaatactca   1800
tactcttcct ttttcaattc agaagaactc gtcaagaagg cgatagaagg cgatgcgctg   1860
cgaatcggga gcggcgatac cgtaaagcac gaggaagcgg tcagcccatt cgccgccaag   1920
ctcttcagca atatcacggg tagccaacgc tatgtcctga tagcggtccg ccacacccag   1980
ccggccacag tcgatgaatc cagaaaagcg gccattttcc accatgatat tcggcaagca   2040
ggcatcgcca tgggtcacga cgagatcctc gccgtcgggc atgcgcgcct tgagcctggc   2100
gaacagttcg gctggcgcga gcccctgatg ctcttcgtcc agatcatcct gatcgacaag   2160
accggcttcc atccgagtac gtgctcgctc gatgcgatgt ttcgcttggt ggtcgaatgg   2220
gcaggtagcc ggatcaagcg tatgcagccg ccgcattgca tcagccatga tggatacttt   2280
ctcggcagga gcaaggtggg atgacaggag atcctgcccc ggcacttcgc ccaatagcag   2340
ccagtccctt cccgcttcag tgacaacgtc gagcacagct gcgcaaggaa cgcccgtcgt   2400
ggccagccac gatagccgcg ctgcctcgtc ctgcagttca ttcagggcac cggacaggtc   2460
ggtcttgaca aaaagaaccg ggcgcccctg cgctgacagc cggaacacgg cggcatcaga   2520
```

-continued

```
gcagccgatt gtctgttgtg cccagtcata gccgaatagc ctctccaccc aagcggccgg    2580
agaacctgcg tgcaatccat cttgttcaat catgcgaaac gatcctcatc ctgtctcttg    2640
atcagatctt gatccctgc gccatcagat ccttggcggc aagaaagcca tccagtttac     2700 tttgcaggc ttcccaacct taccagaggg cgccccagct ggcaattccg gttcgcttgc     2760
tgtccataaa accgccagt ctagctatcg ccatgtaagc ccactgcaag ctacctgctt     2820
tctctttgcg cttgcgtttt ccttgtcca gatagcccag tagctgacat tcatccgggg     2880
tcagcaccgt ttctgcggac tggctttcta cgtgttccgc ttcctttagc agcccttgcg    2940
ccctgaattt tgttaaaatt cgcgttaaat ttttgttaaa tcagctcatt ttttaaccaa    3000
taggccgaaa tcggcaaaat cccttataaa tcaaagaat agaccgagat agggttgagt     3060
gttgttccag tttggaacaa gagtccacta ttaaagaacg tggactccaa cgtcaaaggg    3120 cgaaaaccg tctatcaggg cgatggccca ctacgtgaac catcacccta atcaagtttt     3180
ttggggtcga ggtgccgtaa agcactaaat cggaaccta aagggagccc ccgatttaga     3240
gcttgacggg gaaagccggc gaacgtggcg agaaaggaag ggaagaaagc gaaaggagcg    3300
ggcgctaggg cgctggcaag tgtagcggtc acgctgcgcg taaccaccac acccgccgcg    3360
cttaatgcgc cgctacaggg cgcgtccatt cgccattcag gctgcgcaac tgttgggaag    3420
ggcgatcggt gcgggcctct tcgctattac gccagctggc gaaagggga tgtgctgcaa     3480 ggcgattaag ttgggtaacg ccagggtttt cccagtcacg acgttgtaaa acgacggcca    3540
gtgaattgta atacgactca ctatagggcg aattgggccc tctagatgca tgctcgagcg    3600
gccgcttaat acgactcact atagaggccc tgaaaaaggg ccaaaaacat gaggatcacc    3660
catgtaaaag tcgacaataa ttttgtttaa ctttaagaag gagatataca t atg gcc    3717
                                                           Met Ala
                                                             1 atg cag gcc cat cat cat cat cac cat ggc cag cta ggc cag tct agt     3765
Met Gln Ala His His His His His His Gly Gln Leu Gly Gln Ser Ser
      5                  10                 15 gga ggt gga aat gct cgt act cgg cga cgt gaa cgc aga gcc atg gaa     3813
Gly Gly Gly Asn Ala Arg Thr Arg Arg Arg Glu Arg Arg Ala Met Glu
 20                  25                  30 cga gct acg ctg cca caa gtg ctg gga ggt gga tct ttc gaa cgc cag     3861
Arg Ala Thr Leu Pro Gln Val Leu Gly Gly Gly Ser Phe Glu Arg Gln
35                  40                  45                  50 cac atg gac agc cca gat ctg ggt acc gac gac gac gac aag gct gca     3909
His Met Asp Ser Pro Asp Leu Gly Thr Asp Asp Asp Asp Lys Ala Ala
             55                  60                  65 tct atg gct tct aac ttt act cag ttc gtt ctc gtc gac aat ggc gga    3957
Ser Met Ala Ser Asn Phe Thr Gln Phe Val Leu Val Asp Asn Gly Gly
         70                  75                  80 act ggc gac gtg act gtc gcc cca agc aac ttc gct aac ggg gtc gct    4005
Thr Gly Asp Val Thr Val Ala Pro Ser Asn Phe Ala Asn Gly Val Ala
     85                  90                  95 gaa tgg atc agc tct aac tcg cga tca cag gct tac aaa gta acc tgt    4053
Glu Trp Ile Ser Ser Asn Ser Arg Ser Gln Ala Tyr Lys Val Thr Cys
100                 105                 110 agc gtt cgt cag agc tct gcg cag aat cgc aaa tac acc atc aaa gtc    4101
Ser Val Arg Gln Ser Ser Ala Gln Asn Arg Lys Tyr Thr Ile Lys Val
115                 120                 125                 130 gag gtg cct aaa gtg gca acc cag act gtt ggt ggt gaa gag ctt cct    4149
Glu Val Pro Lys Val Ala Thr Gln Thr Val Gly Gly Glu Glu Leu Pro
            135                 140                 145
```

|  |  |
|---|---|
| gta gcc gga tgg aga tct tac tta aat atg gaa cta acc att cca att<br>Val Ala Gly Trp Arg Ser Tyr Leu Asn Met Glu Leu Thr Ile Pro Ile<br>150                          155                          160 | 4197 |
| ttc gcc acg aat tcc gac tgc gag ctt att gtt aag gca atg caa ggt<br>Phe Ala Thr Asn Ser Asp Cys Glu Leu Ile Val Lys Ala Met Gln Gly<br>165                          170                          175 | 4245 |
| ctc cta aaa gat gga aac ccg att ccc tcg gcc atc gca gca aac tcc<br>Leu Leu Lys Asp Gly Asn Pro Ile Pro Ser Ala Ile Ala Ala Asn Ser<br>180                          185                     190 | 4293 |
| ggc atc tac ggt ggt ggt tca ggt ggt ggt tca tct gca tct atg gct<br>Gly Ile Tyr Gly Gly Gly Ser Gly Gly Gly Ser Ser Ala Ser Met Ala<br>195                          200                      205           210 | 4341 |
| tct aac ttt act cag ttc gtt ctc gtc gac aat ggc gga act ggc gac<br>Ser Asn Phe Thr Gln Phe Val Leu Val Asp Asn Gly Gly Thr Gly Asp<br>                215                     220                     225 | 4389 |
| gtg act gtc gcc cca agc aac ttc gct aac ggg gtc gct gaa tgg atc<br>Val Thr Val Ala Pro Ser Asn Phe Ala Asn Gly Val Ala Glu Trp Ile<br>          230                     235                     240 | 4437 |
| agc tct aac tcg cga tca cag gct tac aaa gta acc tgt agc gtt cgt<br>Ser Ser Asn Ser Arg Ser Gln Ala Tyr Lys Val Thr Cys Ser Val Arg<br>               245                     250                     255 | 4485 |
| cag agc tct gcg cag aat cgc aaa tac acc atc aaa gtc gag gtg cct<br>Gln Ser Ser Ala Gln Asn Arg Lys Tyr Thr Ile Lys Val Glu Val Pro<br>260                          265                     270 | 4533 |
| aaa gtg gca acc cag act gtt ggt ggt gaa gag ctt cct gta gcc gga<br>Lys Val Ala Thr Gln Thr Val Gly Gly Glu Glu Leu Pro Val Ala Gly<br>275                          280                     285           290 | 4581 |
| tgg aga tct tac tta aat atg gaa cta acc att cca att ttc gcc acg<br>Trp Arg Ser Tyr Leu Asn Met Glu Leu Thr Ile Pro Ile Phe Ala Thr<br>               295                     300                     305 | 4629 |
| aat tcc gac tgc gag ctt att gtt aag gca atg caa ggt ctc cta aaa<br>Asn Ser Asp Cys Glu Leu Ile Val Lys Ala Met Gln Gly Leu Leu Lys<br>          310                     315                     320 | 4677 |
| gat gga aac ccg att ccc tca gca atc gca gca aac tcc ggc atc tac<br>Asp Gly Asn Pro Ile Pro Ser Ala Ile Ala Ala Asn Ser Gly Ile Tyr<br>               325                     330                     335 | 4725 |
| ggt ggt ggt tca ggt ggt ggt tca tct gca ggt atg atc agt ctg att<br>Gly Gly Gly Ser Gly Gly Gly Ser Ser Ala Gly Met Ile Ser Leu Ile<br>340                          345                     350 | 4773 |
| gcg gcgttagcgg tagatcgcgt tatcggcatg gaaaacgcca tgccgtggaa<br>Ala<br>355 | 4826 |
| cctgcctgcc gatctcgcct ggtttaaacg caacaccctta aataaacccg tgattatggg | 4886 |
| ccgccatacc tgggaatcaa tcggtcgtcc gttgccagga cgcaaaaata ttatcctcag | 4946 |
| cagtcaaccg ggtacggacg atcgcgtaac gtgggtgaag tcggtggatg aagccatcgc | 5006 |
| ggcgtgtggt gacgtaccag aaatcatggt gattggcggc ggtcgcgttt atgaacagtt | 5066 |
| cttgccaaaa gcgcaaaaac tgtatctgac gcatatcgac gcagaagtgg aaggcgacac | 5126 |
| ccatttcccg gattacgagc cggatgactg ggaatcggta ttcagcgagt ccacgatgc | 5186 |
| tgatgcgcag aactctcaca gctattgctt tgagattctg gagcggcgga actcgaggga | 5246 |
| tccgagctcg gtaccaagct tggcgtaatc atggtcatag ctgtttcctg tgtgaaattg | 5306 |
| ttatccgctc acaattccac acaacatacg agccggaagc ataaagtgta aagcctgggg | 5366 |
| tgcctaatga gtgagctaac tcacattaat tgcgttgcgc tcactgcccg ctttccagtc | 5426 |
| gggaaacctg tcgtgccagc tgcattaatg aatcggccaa cgcgcgggga gaggcggttt | 5486 |
| gcgtattggg cgct | 5500 |

<210> SEQ ID NO 18
<211> LENGTH: 355
<212> TYPE: PRT
<213> ORGANISM: Artificial Sequence
<220> FEATURE:
<223> OTHER INFORMATION: Description of Artificial Sequence: Synthetic plasmid DNAII-H6 full polypeptide

<400> SEQUENCE: 18

Met Ala Met Gln Ala His His His His His Gly Gln Leu Gly Gln
1               5                   10                  15

Ser Ser Gly Gly Gly Asn Ala Arg Thr Arg Arg Glu Arg Arg Ala
                20                  25                  30

Met Glu Arg Ala Thr Leu Pro Gln Val Leu Gly Gly Ser Phe Glu
            35                  40                  45

Arg Gln His Met Asp Ser Pro Asp Leu Gly Thr Asp Asp Asp Lys
        50                  55                  60

Ala Ala Ser Met Ala Ser Asn Phe Thr Gln Phe Val Leu Val Asp Asn
65                  70                  75                  80

Gly Gly Thr Gly Asp Val Thr Val Ala Pro Ser Asn Phe Ala Asn Gly
                85                  90                  95

Val Ala Glu Trp Ile Ser Ser Asn Ser Arg Ser Gln Ala Tyr Lys Val
            100                 105                 110

Thr Cys Ser Val Arg Gln Ser Ser Ala Gln Asn Arg Lys Tyr Thr Ile
            115                 120                 125

Lys Val Glu Val Pro Lys Val Ala Thr Gln Thr Val Gly Gly Glu Glu
130                 135                 140

Leu Pro Val Ala Gly Trp Arg Ser Tyr Leu Asn Met Glu Leu Thr Ile
145                 150                 155                 160

Pro Ile Phe Ala Thr Asn Ser Asp Cys Glu Leu Ile Val Lys Ala Met
                165                 170                 175

Gln Gly Leu Leu Lys Asp Gly Asn Pro Ile Pro Ser Ala Ile Ala Ala
            180                 185                 190

Asn Ser Gly Ile Tyr Gly Gly Gly Ser Gly Gly Gly Ser Ser Ala Ser
            195                 200                 205

Met Ala Ser Asn Phe Thr Gln Phe Val Leu Val Asp Asn Gly Gly Thr
210                 215                 220

Gly Asp Val Thr Val Ala Pro Ser Asn Phe Ala Asn Gly Val Ala Glu
225                 230                 235                 240

Trp Ile Ser Ser Asn Ser Arg Ser Gln Ala Tyr Lys Val Thr Cys Ser
                245                 250                 255

Val Arg Gln Ser Ser Ala Gln Asn Arg Lys Tyr Thr Ile Lys Val Glu
            260                 265                 270

Val Pro Lys Val Ala Thr Gln Thr Val Gly Gly Glu Glu Leu Pro Val
        275                 280                 285

Ala Gly Trp Arg Ser Tyr Leu Asn Met Glu Leu Thr Ile Pro Ile Phe
    290                 295                 300

Ala Thr Asn Ser Asp Cys Glu Leu Ile Val Lys Ala Met Gln Gly Leu
305                 310                 315                 320

Leu Lys Asp Gly Asn Pro Ile Pro Ser Ala Ile Ala Ala Asn Ser Gly
                325                 330                 335

Ile Tyr Gly Gly Gly Ser Gly Gly Gly Ser Ser Ala Gly Met Ile Ser
            340                 345                 350

Leu Ile Ala

355

<210> SEQ ID NO 19
<211> LENGTH: 5641
<212> TYPE: DNA
<213> ORGANISM: Artificial Sequence
<220> FEATURE:
<223> OTHER INFORMATION: Description of Artificial Sequence: Synthetic
      plasmid DNAII-EGF full polynucleotide
<220> FEATURE:
<221> NAME/KEY: CDS
<222> LOCATION: (3712)..(4917)

<400> SEQUENCE: 19

```
cttccgcttc ctcgctcact gactcgctgc gctcggtcgt tcggctgcgg cgagcggtat      60
cagctcactc aaaggcggta atacggttat ccacagaatc aggggataac gcaggaaaga     120
acatgtgagc aaaaggccag caaaaggcca ggaaccgtaa aaaggccgcg ttgctggcgt     180
ttttccatag gctccgcccc cctgacgagc atcacaaaaa tcgacgctca agtcagaggt     240
ggcgaaaccc gacaggacta taaagatacc aggcgtttcc ccctggaagc tccctcgtgc     300
gctctcctgt tccgaccctg ccgcttaccg gatacctgtc cgcctttctc ccttcgggaa     360
gcgtggcgct ttctcatagc tcacgctgta ggtatctcag ttcggtgtag tcgttcgct     420 ccaagctggg ctgtgtgcac gaaccccccg ttcagcccga ccgctgcgcc ttatccggta     480
actatcgtct tgagtccaac ccggtaagac acgacttatc gccactggca gcagccactg     540
gtaacaggat tagcagagcg aggtatgtag gcggtgctac agagttcttg aagtggtggc     600
ctaactacgg ctacactaga agaacagtat ttggtatctg cgctctgctg aagccagtta     660
ccttcggaaa aagagttggt agctcttgat ccggcaaaca aaccaccgct ggtagcggtg     720
gtttttttgt ttgcaagcag cagattacgc gcagaaaaaa aggatctcaa gaagatcctt     780
tgatcttttc tacggggtct gacgctcagt ggaacgaaaa ctcacgttaa gggattttgg     840
tcatgagatt atcaaaaagg atcttcacct agatcctttt aaattaaaaa tgaagtttta     900
aatcaatcta aagtatatat gagtaaactt ggtctgacag ttaccaatgc ttaatcagtg     960
aggcacctat ctcagcgatc tgtctatttc gttcatccat agttgcctga ctccccgtcg    1020
tgtagataac tacgatacgg gagggcttac catctggccc cagtgctgca atgataccgc    1080
gagacccacg ctcaccggct ccagatttat cagcaataaa ccagccagcc ggaagggccg    1140
agcgcagaag tggtcctgca actttatccg cctccatcca gtctattaat tgttgccggg    1200
aagctagagt aagtagttcg ccagttaata gtttgcgcaa cgttgttgcc attgctacag    1260
gcatcgtggt gtcacgctcg tcgtttggta tggcttcatt cagctccggt tcccaacgat    1320
caaggcgagt tacatgatcc cccatgttgt gcaaaaaagc ggttagctcc ttcggtcctc    1380
cgatcgttgt cagaagtaag ttggccgcag tgttatcact catggttatg gcagcactgc    1440
ataattctct tactgtcatg ccatccgtaa gatgcttttc tgtgactggt gagtactcaa    1500
ccaagtcatt ctgagaatag tgtatgcggc gaccgagttg ctcttgcccg gcgtcaatac    1560
gggataatac cgcgccacat agcagaactt taaaagtgct catcattgga aaacgttctt    1620
cggggcgaaa actctcaagg atcttaccgc tgttgagatc cagttcgatg taacccactc    1680
gtgcacccaa ctgatcttca gcatctttta ctttcaccag cgtttctggg tgagcaaaaa    1740
caggaaggca aaatgccgca aaaaagggaa taagggcgac acggaaatgt tgaatactca    1800
tactcttcct ttttcaattc agaagaactc gtcaagaagg cgatagaagg cgatgcgctg    1860
cgaatcggga gcggcgatac cgtaaagcac gaggaagcgg tcagcccatt cgccgccaag    1920
```

-continued

```
ctcttcagca atatcacggg tagccaacgc tatgtcctga tagcggtccg ccacacccag      1980
ccggccacag tcgatgaatc cagaaaagcg gccattttcc accatgatat tcggcaagca      2040
ggcatcgcca tgggtcacga cgagatcctc gccgtcgggc atgcgcgcct tgagcctggc      2100
gaacagttcg gctggcgcga gcccctgatg ctcttcgtcc agatcatcct gatcgacaag      2160
accggcttcc atccgagtac gtgctcgctc gatgcgatgt tcgcttggt ggtcgaatgg       2220 gcaggtagcc ggatcaagcg tatgcagccg ccgcattgca tcagccatga tggatacttt      2280
ctcggcagga gcaaggtggg atgacaggag atcctgcccc ggcacttcgc ccaatagcag      2340
ccagtcccct cccgcttcag tgacaacgtc gagcacagct gcgcaaggaa cgcccgtcgt      2400
ggccagccac gatagccgcg ctgcctcgtc ctgcagttca ttcagggcac cggacaggtc      2460
ggtcttgaca aaagaaccg gcgcccctg cgctgacagc cggaacacgg cggcatcaga       2520
gcagccgatt gtctgttgtg cccagtcata gccgaatagc ctctccaccc aagcggccgg      2580
agaacctgcg tgcaatccat cttgttcaat catgcgaaac gatcctcatc ctgtctcttg      2640
atcagatctt gatcccctgc gccatcagat ccttggcggc aagaaagcca tccagtttac      2700
tttgcagggc ttcccaacct taccagaggg cgccccagct ggcaattccg gttcgcttgc      2760
tgtccataaa accgccagt ctagctatcg ccatgtaagc ccactgcaag ctacctgctt       2820
tctctttgcg cttgcgtttt cccttgtcca gatagcccag tagctgacat tcatccgggg      2880
tcagcaccgt ttctgcggac tggctttcta cgtgttccgc ttcctttagc agcccttgcg      2940
ccctgaattt tgttaaaatt cgcgttaaat ttttgttaaa tcagctcatt ttttaaccaa      3000
taggccgaaa tcggcaaaat cccttataaa tcaaaagaat agaccgagat agggttgagt      3060
gttgttccag tttggaacaa gagtccacta ttaaagaacg tggactccaa cgtcaaaggg      3120
cgaaaaaccg tctatcaggg cgatggccca ctacgtgaac catcacccta atcaagtttt      3180
ttggggtcga ggtgccgtaa agcactaaat cggaacccta aagggagccc ccgatttaga      3240
gcttgacggg gaaagccggc gaacgtggcg agaaaggaag ggaagaaagc gaaaggagcg      3300
ggcgctaggg cgctggcaag tgtagcggtc acgctgcgcg taaccaccac acccgccgcg      3360
cttaatgcgc cgctacaggg cgcgtccatt cgccattcag gctgcgcaac tgttgggaag      3420
ggcgatcggt gcgggcctct tcgctattac gccagctggc gaaaggggga tgtgctgcaa      3480
ggcgattaag ttgggtaacg ccagggtttt cccagtcacg acgttgtaaa acgacggcca      3540
gtgaattgta atacgactca ctatagggcg aattgggccc tctagatgca tgctcgagcg      3600
gccgcttaat acgactcact atagaggccc tgaaaaaggg ccaaaaacat gaggatcacc      3660
catgtaaaag tcgacaataa ttttgtttaa ctttaagaag gagatataca t atg gcc      3717
                                                         Met Ala
                                                           1 atg cag gcc aat agt gac tct gaa tgt ccc ctg tcc cac gat ggg tac      3765
Met Gln Ala Asn Ser Asp Ser Glu Cys Pro Leu Ser His Asp Gly Tyr
          5                  10                  15 tgc ctc cat gat ggt gtg tgc atg tat att gaa gca ttg gac aag tat      3813
Cys Leu His Asp Gly Val Cys Met Tyr Ile Glu Ala Leu Asp Lys Tyr
     20                  25                  30 gca tgc aac tgt gtt gtt ggc tac atc ggg gag cga tgt cag tac cga      3861
Ala Cys Asn Cys Val Val Gly Tyr Ile Gly Glu Arg Cys Gln Tyr Arg
35                   40                  45                  50 gac ctg aag tgg tgg gaa ctg cgc ggc cag cta ggc cag tct agt gga      3909
Asp Leu Lys Trp Trp Glu Leu Arg Gly Gln Leu Gly Gln Ser Ser Gly
                 55                  60                  65
```

-continued

| | |
|---|---|
| ggt gga aat gct cgt act cgg cga cgt gaa cgc aga gcc atg gaa cga<br>Gly Gly Asn Ala Arg Thr Arg Arg Arg Glu Arg Arg Ala Met Glu Arg<br>              70                     75                 80 | 3957 |
| gct acg ctg cca caa gtg ctg gga ggt gga tct ttc gaa cgc cag cac<br>Ala Thr Leu Pro Gln Val Leu Gly Gly Gly Ser Phe Glu Arg Gln His<br>        85                     90                     95 | 4005 |
| atg gac agc cca gat ctg ggt acc gac gac gac aag gct gca tct<br>Met Asp Ser Pro Asp Leu Gly Thr Asp Asp Asp Lys Ala Ala Ser<br>100                     105                   110 | 4053 |
| atg gct tct aac ttt act cag ttc gtt ctc gtc gac aat ggc gga act<br>Met Ala Ser Asn Phe Thr Gln Phe Val Leu Val Asp Asn Gly Gly Thr<br>115                    120                   125                 130 | 4101 |
| ggc gac gtg act gtc gcc cca agc aac ttc gct aac ggg gtc gct gaa<br>Gly Asp Val Thr Val Ala Pro Ser Asn Phe Ala Asn Gly Val Ala Glu<br>              135                   140                   145 | 4149 |
| tgg atc agc tct aac tcg cga tca cag gct tac aaa gta acc tgt agc<br>Trp Ile Ser Ser Asn Ser Arg Ser Gln Ala Tyr Lys Val Thr Cys Ser<br>                150                   155                   160 | 4197 |
| gtt cgt cag agc tct gcg cag aat cgc aaa tac acc atc aaa gtc gag<br>Val Arg Gln Ser Ser Ala Gln Asn Arg Lys Tyr Thr Ile Lys Val Glu<br>        165                     170                     175 | 4245 |
| gtg cct aaa gtg gca acc cag act gtt ggt ggt gaa gag ctt cct gta<br>Val Pro Lys Val Ala Thr Gln Thr Val Gly Gly Glu Glu Leu Pro Val<br>180                     185                   190 | 4293 |
| gcc gga tgg aga tct tac tta aat atg gaa cta acc att cca att ttc<br>Ala Gly Trp Arg Ser Tyr Leu Asn Met Glu Leu Thr Ile Pro Ile Phe<br>195                     200                   205                 210 | 4341 |
| gcc acg aat tcc gac tgc gag ctt att gtt aag gca atg caa ggt ctc<br>Ala Thr Asn Ser Asp Cys Glu Leu Ile Val Lys Ala Met Gln Gly Leu<br>              215                   220                   225 | 4389 |
| cta aaa gat gga aac ccg att ccc tcg gcc atc gca gca aac tcc ggc<br>Leu Lys Asp Gly Asn Pro Ile Pro Ser Ala Ile Ala Ala Asn Ser Gly<br>                230                   235                   240 | 4437 |
| atc tac ggt ggt ggt tca ggt ggt ggt tca tct gca tct atg gct tct<br>Ile Tyr Gly Gly Gly Ser Gly Gly Gly Ser Ser Ala Ser Met Ala Ser<br>        245                     250                     255 | 4485 |
| aac ttt act cag ttc gtt ctc gtc gac aat ggc gga act ggc gac gtg<br>Asn Phe Thr Gln Phe Val Leu Val Asp Asn Gly Gly Thr Gly Asp Val<br>260                     265                   270 | 4533 |
| act gtc gcc cca agc aac ttc gct aac ggg gtc gct gaa tgg atc agc<br>Thr Val Ala Pro Ser Asn Phe Ala Asn Gly Val Ala Glu Trp Ile Ser<br>275                     280                   285                 290 | 4581 |
| tct aac tcg cga tca cag gct tac aaa gta acc tgt agc gtt cgt cag<br>Ser Asn Ser Arg Ser Gln Ala Tyr Lys Val Thr Cys Ser Val Arg Gln<br>                     295                   300                   305 | 4629 |
| agc tct gcg cag aat cgc aaa tac acc atc aaa gtc gag gtg cct aaa<br>Ser Ser Ala Gln Asn Arg Lys Tyr Thr Ile Lys Val Glu Val Pro Lys<br>                310                   315                   320 | 4677 |
| gtg gca acc cag act gtt ggt ggt gaa gag ctt cct gta gcc gga tgg<br>Val Ala Thr Gln Thr Val Gly Gly Glu Glu Leu Pro Val Ala Gly Trp<br>        325                     330                     335 | 4725 |
| aga tct tac tta aat atg gaa cta acc att cca att ttc gcc acg aat<br>Arg Ser Tyr Leu Asn Met Glu Leu Thr Ile Pro Ile Phe Ala Thr Asn<br>340                     345                   350 | 4773 |
| tcc gac tgc gag ctt att gtt aag gca atg caa ggt ctc cta aaa gat<br>Ser Asp Cys Glu Leu Ile Val Lys Ala Met Gln Gly Leu Leu Lys Asp<br>355                     360                   365                 370 | 4821 |
| gga aac ccg att ccc tca gca atc gca gca aac tcc ggc atc tac ggt<br>Gly Asn Pro Ile Pro Ser Ala Ile Ala Ala Asn Ser Gly Ile Tyr Gly<br>                375                   380                   385 | 4869 |

-continued

```
ggt ggt tca ggt ggt ggt tca tct gca ggt atg atc agt ctg att gcg    4917
Gly Gly Ser Gly Gly Gly Ser Ser Ala Gly Met Ile Ser Leu Ile Ala
            390                 395                 400 gcgttagcgg tagatcgcgt tatcggcatg gaaaacgcca tgccgtggaa cctgcctgcc    4977
gatctcgcct ggtttaaacg caacaccttA ataaacccg tgattatggg ccgccatacc    5037
tgggaatcaa tcggtcgtcc gttgccagga cgcaaaaata ttatcctcag cagtcaaccg    5097
ggtacggacg atcgcgtaac gtgggtgaag tcggtggatg aagccatcgc ggcgtgtggt    5157
gacgtaccag aaatcatggt gattggcggc ggtcgcgttt atgaacagtt cttgccaaaa    5217
gcgcaaaaac tgtatctgac gcatatcgac gcagaagtgg aaggcgacac ccatttcccg    5277
gattacgagc cggatgactg ggaatcggta ttcagcgagt ccacgatgc tgatgcgcag     5337 aactctcaca gctattgctt tgagattctg gagcggcgga actcgaggga tccgagctcg    5397
gtaccaagct tggcgtaatc atggtcatag ctgtttcctg tgtgaaattg ttatccgctc    5457
acaattccac acaacatacg agccggaagc ataaagtgta aagcctgggg tgcctaatga    5517
gtgagctaac tcacattaat tgcgttgcgc tcactgcccg ctttccagtc gggaaacctg    5577
tcgtgccagc tgcattaatg aatcggccaa cgcgcgggga gaggcggttt gcgtattggg    5637
cgct                                                                 5641
```

<210> SEQ ID NO 20
<211> LENGTH: 402
<212> TYPE: PRT
<213> ORGANISM: Artificial Sequence
<220> FEATURE:
<223> OTHER INFORMATION: Description of Artificial Sequence: Synthetic
    plasmid DNAII-EGF full polypeptide

<400> SEQUENCE: 20

```
Met Ala Met Gln Ala Asn Ser Asp Ser Glu Cys Pro Leu Ser His Asp
1               5                   10                  15

Gly Tyr Cys Leu His Asp Gly Val Cys Met Tyr Ile Glu Ala Leu Asp
            20                  25                  30

Lys Tyr Ala Cys Asn Cys Val Val Gly Tyr Ile Gly Glu Arg Cys Gln
        35                  40                  45

Tyr Arg Asp Leu Lys Trp Trp Glu Leu Arg Gly Gln Leu Gly Gln Ser
    50                  55                  60

Ser Gly Gly Gly Asn Ala Arg Thr Arg Arg Glu Arg Arg Ala Met
65                  70                  75                  80

Glu Arg Ala Thr Leu Pro Gln Val Leu Gly Gly Gly Ser Phe Glu Arg
                85                  90                  95

Gln His Met Asp Ser Pro Asp Leu Gly Thr Asp Asp Asp Lys Ala
            100                 105                 110

Ala Ser Met Ala Ser Asn Phe Thr Gln Phe Val Leu Val Asp Asn Gly
        115                 120                 125

Gly Thr Gly Asp Val Thr Val Ala Pro Ser Asn Phe Ala Asn Gly Val
    130                 135                 140

Ala Glu Trp Ile Ser Ser Asn Ser Arg Ser Gln Ala Tyr Lys Val Thr
145                 150                 155                 160

Cys Ser Val Arg Gln Ser Ser Ala Gln Asn Arg Lys Tyr Thr Ile Lys
                165                 170                 175

Val Glu Val Pro Lys Val Ala Thr Gln Thr Val Gly Gly Glu Glu Leu
            180                 185                 190

Pro Val Ala Gly Trp Arg Ser Tyr Leu Asn Met Glu Leu Thr Ile Pro
```

```
            195                 200                 205
Ile Phe Ala Thr Asn Ser Asp Cys Glu Leu Ile Val Lys Ala Met Gln
210                 215                 220

Gly Leu Leu Lys Asp Gly Asn Pro Ile Pro Ser Ala Ile Ala Ala Asn
225                 230                 235                 240

Ser Gly Ile Tyr Gly Gly Ser Gly Gly Ser Ser Ala Ser Met
                245                 250                 255

Ala Ser Asn Phe Thr Gln Phe Val Leu Val Asp Asn Gly Gly Thr Gly
            260                 265                 270

Asp Val Thr Val Ala Pro Ser Asn Phe Ala Asn Gly Val Ala Glu Trp
        275                 280                 285

Ile Ser Ser Asn Ser Arg Ser Gln Ala Tyr Lys Val Thr Cys Ser Val
290                 295                 300

Arg Gln Ser Ser Ala Gln Asn Arg Lys Tyr Thr Ile Lys Val Glu Val
305                 310                 315                 320

Pro Lys Val Ala Thr Gln Thr Val Gly Gly Glu Glu Leu Pro Val Ala
                325                 330                 335

Gly Trp Arg Ser Tyr Leu Asn Met Glu Leu Thr Ile Pro Ile Phe Ala
            340                 345                 350

Thr Asn Ser Asp Cys Glu Leu Ile Val Lys Ala Met Gln Gly Leu Leu
        355                 360                 365

Lys Asp Gly Asn Pro Ile Pro Ser Ala Ile Ala Ala Asn Ser Gly Ile
370                 375                 380

Tyr Gly Gly Gly Ser Gly Gly Ser Ser Ala Gly Met Ile Ser Leu
385                 390                 395                 400

Ile Ala

<210> SEQ ID NO 21
<211> LENGTH: 5803
<212> TYPE: DNA
<213> ORGANISM: Artificial Sequence
<220> FEATURE:
<223> OTHER INFORMATION: Description of Artificial Sequence: Synthetic
      plasmid DNAII-FKBP full polynucleotide
<220> FEATURE:
<221> NAME/KEY: CDS
<222> LOCATION: (3712)..(5079)

<400> SEQUENCE: 21
cttccgcttc ctcgctcact gactcgctgc gctcggtcgt tcggctgcgg cgagcggtat    60
cagctcactc aaaggcggta atacggttat ccacagaatc aggggataac gcaggaaaga   120
acatgtgagc aaaaggccag caaaaggcca ggaaccgtaa aaaggccgcg ttgctggcgt   180
ttttccatag gctccgcccc cctgacgagc atcacaaaaa tcgacgctca agtcagaggt   240
ggcgaaaccc gacaggacta taaagatacc aggcgtttcc ccctggaagc tccctcgtgc   300
gctctcctgt tccgaccctg ccgcttaccg gatacctgtc cgcctttctc ccttcgggaa   360
gcgtggcgct ttctcatagc tcacgctgta ggtatctcag ttcggtgtag gtcgttcgct   420
ccaagctggg ctgtgtgcac gaaccccccg ttcagcccga ccgctgcgcc ttatccggta   480
actatcgtct tgagtccaac ccggtaagac acgacttatc gccactggca gcagccactg   540
gtaacaggat tagcagagcg aggtatgtag gcggtgctac agagttcttg aagtggtggc   600
ctaactacgg ctacactaga agaacagtat ttggtatctg cgctctgctg aagccagtta   660
ccttcggaaa aagagttggt agctcttgat ccggcaaaca aaccaccgct ggtagcggtg   720
gtttttttgt ttgcaagcag cagattacgc gcagaaaaaa aggatctcaa gaagatcctt   780
```

```
tgatcttttc tacggggtct gacgctcagt ggaacgaaaa ctcacgttaa gggattttgg      840
tcatgagatt atcaaaaagg atcttcacct agatccttt aaattaaaaa tgaagtttta      900
aatcaatcta agtatatat gagtaaactt ggtctgacag ttaccaatgc ttaatcagtg      960
aggcacctat ctcagcgatc tgtctatttc gttcatccat agttgcctga ctccccgtcg     1020
tgtagataac tacgatacgg gagggcttac catctggccc cagtgctgca atgataccgc     1080
gagacccacg ctcaccggct ccagatttat cagcaataaa ccagccagcc ggaagggccg     1140
agcgcagaag tggtcctgca actttatccg cctccatcca gtctattaat tgttgccggg     1200
aagctagagt aagtagttcg ccagttaata gtttgcgcaa cgttgttgcc attgctacag     1260
gcatcgtggt gtcacgctcg tcgtttggta tggcttcatt cagctccggt tcccaacgat     1320
caaggcgagt tacatgatcc cccatgttgt gcaaaaaagc ggttagctcc ttcggtcctc     1380
cgatcgttgt cagaagtaag ttggccgcag tgttatcact catggttatg gcagcactgc     1440
ataattctct tactgtcatg ccatccgtaa gatgcttttc tgtgactggt gagtactcaa     1500
ccaagtcatt ctgagaatag tgtatgcggc gaccgagttg ctcttgcccg cgtcaatac     1560 gggataatac cgcgccacat agcagaactt taaaagtgct catcattgga aaacgttctt     1620
cggggcgaaa actctcaagg atcttaccgc tgttgagatc cagttcgatg taacccactc     1680
gtgcacccaa ctgatcttca gcatcttta ctttcaccag cgtttctggg tgagcaaaaa     1740
caggaaggca aaatgccgca aaaaagggaa taagggcgac acggaaatgt tgaatactca     1800
tactcttcct ttttcaattc agaagaactc gtcaagaagg cgatagaagg cgatgcgctg     1860
cgaatcggga gcggcgatac cgtaaagcac gaggaagcgg tcagcccatt cgccgccaag     1920
ctcttcagca atatcacggg tagccaacgc tatgtcctga tagcggtccg ccacacccag     1980
ccggccacag tcgatgaatc cagaaaagcg gccattttcc accatgatat tcggcaagca     2040
ggcatcgcca tgggtcacga cgagatcctc gccgtcgggc atgcgcgcct tgagcctggc     2100
gaacagttcg gctggcgcga gcccctgatg ctcttcgtcc agatcatcct gatcgacaag     2160
accggcttcc atccgagtac gtgctcgctc gatgcgatgt ttcgcttggt ggtcgaatgg     2220
gcaggtagcc ggatcaagcg tatgcagccg ccgcattgca tcagccatga tggatacttt     2280
ctcggcagga gcaaggtggg atgacaggag atcctgcccc ggcacttcgc ccaatagcag     2340
ccagtccctt cccgcttcag tgacaacgtc gagcacagct gcgcaaggaa cgcccgtcgt     2400
ggccagccac gatagccgcg ctgcctcgtc ctgcagttca ttcagggcac cggacaggtc     2460
ggtcttgaca aaaagaaccg ggcgcccctg cgctgacagc cggaacacgg cggcatcaga     2520
gcagccgatt gtctgttgtg cccagtcata gccgaatagc ctctccaccc aagcggccgg     2580
agaacctgcg tgcaatccat cttgttcaat catgcgaaac gatcctcatc ctgtctcttg     2640
atcagatctt gatcccctgc gccatcagat ccttggcggc aagaaagcca tccagtttac     2700
tttgcagggc ttcccaacct taccagaggg cgccccagct ggcaattccg ttcgcttgc      2760 tgtccataaa accgcccagt ctagctatcg ccatgtaagc ccactgcaag ctacctgctt     2820
tctctttgcg cttgcgtttt cccttgtcca gatagcccag tagctgacat tcatccgggg     2880
tcagcaccgt ttctgcggac tggctttcta cgtgttccgc ttcctttagc agcccttgcg     2940
ccctgaattt tgttaaaatt cgcgttaaat ttttgttaaa tcagctcatt ttttaaccaa     3000
taggccgaaa tcggcaaaat cccttataaa tcaaaagaat agaccgagat agggttgagt     3060
gttgttccag tttggaacaa gagtccacta ttaaagaacg tggactccaa cgtcaaaggg     3120
```

| | |
|---|---|
| cgaaaaaccg tctatcaggg cgatggccca ctacgtgaac catcacccta atcaagtttt | 3180 |
| ttggggtcga ggtgccgtaa agcactaaat cggaacccta aagggagccc ccgatttaga | 3240 |
| gcttgacggg gaaagccggc gaacgtggcg agaaaggaag ggaagaaagc gaaaggagcg | 3300 |
| ggcgctaggg cgctggcaag tgtagcggtc acgctgcgcg taaccaccac acccgccgcg | 3360 |
| cttaatgcgc cgctacaggg cgcgtccatt cgccattcag gctgcgcaac tgttgggaag | 3420 |
| ggcgatcggt gcgggcctct tcgctattac gccagctggc gaaaggggga tgtgctgcaa | 3480 |
| ggcgattaag ttgggtaacg ccagggtttt cccagtcacg acgttgtaaa acgacggcca | 3540 |
| gtgaattgta atacgactca ctatagggcg aattgggccc tctagatgca tgctcgagcg | 3600 |
| gccgcttaat acgactcact atagaggccc tgaaaaaggg ccaaaaacat gaggatcacc | 3660 |
| catgtaaaag tcgacaataa ttttgtttaa ctttaagaag gagatataca t atg gcc | 3717 |
| | Met Ala |
| | 1 |

```
atg cag gcc gga gtg cag gtg gaa acc atc tcc cca gga gac ggg cgc      3765
Met Gln Ala Gly Val Gln Val Glu Thr Ile Ser Pro Gly Asp Gly Arg
         5                  10                  15 acc ttc ccc aag cgc ggc cag acc tgc gtg gtg cac tac acc ggg atg      3813
Thr Phe Pro Lys Arg Gly Gln Thr Cys Val Val His Tyr Thr Gly Met
     20                  25                  30 ctt gaa gat gga aag aaa ttt gat tcc tcc cgg gac aga aac aag ccc      3861
Leu Glu Asp Gly Lys Lys Phe Asp Ser Ser Arg Asp Arg Asn Lys Pro
 35                  40                  45                  50 ttt aag ttt atg cta ggc aag cag gag gtg atc cga ggc tgg gaa gaa      3909
Phe Lys Phe Met Leu Gly Lys Gln Glu Val Ile Arg Gly Trp Glu Glu
                 55                  60                  65 ggg gtt gcc cag atg agt gtg ggt cag aga gcc aaa ctg act ata tct      3957
Gly Val Ala Gln Met Ser Val Gly Gln Arg Ala Lys Leu Thr Ile Ser
             70                  75                  80 cca gat tat gcc tat ggt gcc act ggg cac cca ggc atc atc cca cca      4005
Pro Asp Tyr Ala Tyr Gly Ala Thr Gly His Pro Gly Ile Ile Pro Pro
         85                  90                  95 cat gcc act ctc gtc ttc gat gtg gag ctt cta aaa ctg gaa ggc cag      4053
His Ala Thr Leu Val Phe Asp Val Glu Leu Leu Lys Leu Glu Gly Gln
    100                 105                 110 cta ggc cag tct agt gga ggt gga aat gct cgt act cgg cga cgt gaa      4101
Leu Gly Gln Ser Ser Gly Gly Gly Asn Ala Arg Thr Arg Arg Arg Glu
115                 120                 125                 130 cgc aga gcc atg gaa cga gct acg ctg cca caa gtg ctg gga ggt gga      4149
Arg Arg Ala Met Glu Arg Ala Thr Leu Pro Gln Val Leu Gly Gly Gly
                135                 140                 145 tct ttc gaa cgc cag cac atg gac agc cca gat ctg ggt acc gac gac      4197
Ser Phe Glu Arg Gln His Met Asp Ser Pro Asp Leu Gly Thr Asp Asp
            150                 155                 160 gac gac aag gct gca tct atg gct tct aac ttt act cag ttc gtt ctc      4245
Asp Asp Lys Ala Ala Ser Met Ala Ser Asn Phe Thr Gln Phe Val Leu
        165                 170                 175 gtc gac aat ggc gga act ggc gac gtg act gtc gcc cca agc aac ttc      4293
Val Asp Asn Gly Gly Thr Gly Asp Val Thr Val Ala Pro Ser Asn Phe
    180                 185                 190 gct aac ggg gtc gct gaa tgg atc agc tct aac tcg cga tca cag gct      4341
Ala Asn Gly Val Ala Glu Trp Ile Ser Ser Asn Ser Arg Ser Gln Ala
195                 200                 205                 210 tac aaa gta acc tgt agc gtt cgt cag agc tct gcg cag aat cgc aaa      4389
Tyr Lys Val Thr Cys Ser Val Arg Gln Ser Ser Ala Gln Asn Arg Lys
                215                 220                 225 tac acc atc aaa gtc gag gtg cct aaa gtg gca acc cag act gtt ggt      4437
```

```
Tyr Thr Ile Lys Val Glu Val Pro Lys Val Ala Thr Gln Thr Val Gly
            230                 235                 240 ggt gaa gag ctt cct gta gcc gga tgg aga tct tac tta aat atg gaa    4485
Gly Glu Glu Leu Pro Val Ala Gly Trp Arg Ser Tyr Leu Asn Met Glu
        245                 250                 255 cta acc att cca att ttc gcc acg aat tcc gac tgc gag ctt att gtt    4533
Leu Thr Ile Pro Ile Phe Ala Thr Asn Ser Asp Cys Glu Leu Ile Val
    260                 265                 270 aag gca atg caa ggt ctc cta aaa gat gga aac ccg att ccc tcg gcc    4581
Lys Ala Met Gln Gly Leu Leu Lys Asp Gly Asn Pro Ile Pro Ser Ala
275                 280                 285                 290 atc gca gca aac tcc ggc atc tac ggt ggt ggt tca ggt ggt ggt tca    4629
Ile Ala Ala Asn Ser Gly Ile Tyr Gly Gly Gly Ser Gly Gly Gly Ser
                295                 300                 305 tct gca tct atg gct tct aac ttt act cag ttc gtt ctc gtc gac aat    4677
Ser Ala Ser Met Ala Ser Asn Phe Thr Gln Phe Val Leu Val Asp Asn
            310                 315                 320 ggc gga act ggc gac gtg act gtc gcc cca agc aac ttc gct aac ggg    4725
Gly Gly Thr Gly Asp Val Thr Val Ala Pro Ser Asn Phe Ala Asn Gly
        325                 330                 335 gtc gct gaa tgg atc agc tct aac tcg cga tca cag gct tac aaa gta    4773
Val Ala Glu Trp Ile Ser Ser Asn Ser Arg Ser Gln Ala Tyr Lys Val
    340                 345                 350 acc tgt agc gtt cgt cag agc tct gcg cag aat cgc aaa tac acc atc    4821
Thr Cys Ser Val Arg Gln Ser Ser Ala Gln Asn Arg Lys Tyr Thr Ile
355                 360                 365                 370 aaa gtc gag gtg cct aaa gtg gca acc cag act gtt ggt ggt gaa gag    4869
Lys Val Glu Val Pro Lys Val Ala Thr Gln Thr Val Gly Gly Glu Glu
                375                 380                 385 ctt cct gta gcc gga tgg aga tct tac tta aat atg gaa cta acc att    4917
Leu Pro Val Ala Gly Trp Arg Ser Tyr Leu Asn Met Glu Leu Thr Ile
            390                 395                 400 cca att ttc gcc acg aat tcc gac tgc gag ctt att gtt aag gca atg    4965
Pro Ile Phe Ala Thr Asn Ser Asp Cys Glu Leu Ile Val Lys Ala Met
        405                 410                 415 caa ggt ctc cta aaa gat gga aac ccg att ccc tca gca atc gca gca    5013
Gln Gly Leu Leu Lys Asp Gly Asn Pro Ile Pro Ser Ala Ile Ala Ala
    420                 425                 430 aac tcc ggc atc tac ggt ggt ggt tca ggt ggt ggt tca tct gca ggt    5061
Asn Ser Gly Ile Tyr Gly Gly Gly Ser Gly Gly Gly Ser Ser Ala Gly
435                 440                 445                 450 atg atc agt ctg att gcg gcgttagcgg tagatcgcgt tatcggcatg           5109
Met Ile Ser Leu Ile Ala
            455 gaaaacgcca tgccgtggaa cctgcctgcc gatctcgcct ggtttaaacg caacaccttta    5169 aataaacccg tgattatggg ccgccatacc tgggaatcaa tcggtcgtcc gttgccagga    5229 cgcaaaaata ttatcctcag cagtcaaccg ggtacggacg atcgcgtaac gtgggtgaag    5289 tcggtggatg aagccatcgc ggcgtgtggt gacgtaccag aaatcatggt gattggcggc    5349 ggtcgcgttt atgaacagtt cttgccaaaa gcgcaaaaac tgtatctgac gcatatcgac    5409 gcagaagtgg aaggcgacac ccatttcccg gattacgagc cggatgactg ggaatcggta    5469 ttcagcgagt ccacgatgc tgatgcgcag aactctcaca gctattgctt tgagattctg    5529 gagcggcgga actcgaggga tccgagctcg gtaccaagct tggcgtaatc atggtcatag    5589 ctgtttcctg tgtgaaattg ttatccgctc acaattccac acaacatacg agccggaagc    5649 ataaagtgta aagcctgggg tgcctaatga gtgagctaac tcacattaat tgcgttgcgc    5709
```

```
tcactgcccg ctttccagtc gggaaacctg tcgtgccagc tgcattaatg aatcggccaa   5769
cgcgcgggga gaggcggttt gcgtattggg cgct                              5803
```

<210> SEQ ID NO 22
<211> LENGTH: 456
<212> TYPE: PRT
<213> ORGANISM: Artificial Sequence
<220> FEATURE:
<223> OTHER INFORMATION: Description of Artificial Sequence: Synthetic
      plasmid DNAII-FKBP full polypeptide

<400> SEQUENCE: 22

```
Met Ala Met Gln Ala Gly Val Gln Val Glu Thr Ile Ser Pro Gly Asp
1               5                   10                  15

Gly Arg Thr Phe Pro Lys Arg Gly Gln Thr Cys Val Val His Tyr Thr
            20                  25                  30

Gly Met Leu Glu Asp Gly Lys Lys Phe Asp Ser Ser Arg Asp Arg Asn
        35                  40                  45

Lys Pro Phe Lys Phe Met Leu Gly Lys Gln Glu Val Ile Arg Gly Trp
    50                  55                  60

Glu Glu Gly Val Ala Gln Met Ser Val Gly Gln Arg Ala Lys Leu Thr
65                  70                  75                  80

Ile Ser Pro Asp Tyr Ala Tyr Gly Ala Thr Gly His Pro Gly Ile Ile
                85                  90                  95

Pro Pro His Ala Thr Leu Val Phe Asp Val Glu Leu Leu Lys Leu Glu
            100                 105                 110

Gly Gln Leu Gly Gln Ser Ser Gly Gly Gly Asn Ala Arg Thr Arg Arg
        115                 120                 125

Arg Glu Arg Arg Ala Met Glu Arg Ala Thr Leu Pro Gln Val Leu Gly
    130                 135                 140

Gly Gly Ser Phe Glu Arg Gln His Met Asp Ser Pro Asp Leu Gly Thr
145                 150                 155                 160

Asp Asp Asp Asp Lys Ala Ala Ser Met Ala Ser Asn Phe Thr Gln Phe
                165                 170                 175

Val Leu Val Asp Asn Gly Gly Thr Gly Asp Val Thr Val Ala Pro Ser
            180                 185                 190

Asn Phe Ala Asn Gly Val Ala Glu Trp Ile Ser Ser Asn Ser Arg Ser
        195                 200                 205

Gln Ala Tyr Lys Val Thr Cys Ser Val Arg Gln Ser Ser Ala Gln Asn
    210                 215                 220

Arg Lys Tyr Thr Ile Lys Val Glu Val Pro Lys Val Ala Thr Gln Thr
225                 230                 235                 240

Val Gly Gly Glu Glu Leu Pro Val Ala Gly Trp Arg Ser Tyr Leu Asn
                245                 250                 255

Met Glu Leu Thr Ile Pro Ile Phe Ala Thr Asn Ser Asp Cys Glu Leu
            260                 265                 270

Ile Val Lys Ala Met Gln Gly Leu Leu Lys Asp Gly Asn Pro Ile Pro
        275                 280                 285

Ser Ala Ile Ala Ala Asn Ser Gly Ile Tyr Gly Gly Ser Gly Gly
    290                 295                 300

Gly Ser Ser Ala Ser Met Ala Ser Asn Phe Thr Gln Phe Val Leu Val
305                 310                 315                 320

Asp Asn Gly Gly Thr Gly Asp Val Thr Val Ala Pro Ser Asn Phe Ala
                325                 330                 335

Asn Gly Val Ala Glu Trp Ile Ser Ser Asn Ser Arg Ser Gln Ala Tyr
```

```
            340                 345                 350
Lys Val Thr Cys Ser Val Arg Gln Ser Ser Ala Gln Asn Arg Lys Tyr
        355                 360                 365

Thr Ile Lys Val Glu Val Pro Lys Val Ala Thr Gln Thr Val Gly Gly
    370                 375                 380

Glu Glu Leu Pro Val Ala Gly Trp Arg Ser Tyr Leu Asn Met Glu Leu
385                 390                 395                 400

Thr Ile Pro Ile Phe Ala Thr Asn Ser Asp Cys Glu Leu Ile Val Lys
                405                 410                 415

Ala Met Gln Gly Leu Leu Lys Asp Gly Asn Pro Ile Pro Ser Ala Ile
            420                 425                 430

Ala Ala Asn Ser Gly Ile Tyr Gly Gly Gly Ser Gly Gly Gly Ser Ser
        435                 440                 445

Ala Gly Met Ile Ser Leu Ile Ala
    450                 455

<210> SEQ ID NO 23
<211> LENGTH: 5974
<212> TYPE: DNA
<213> ORGANISM: Artificial Sequence
<220> FEATURE:
<223> OTHER INFORMATION: Description of Artificial Sequence: Synthetic
      plasmid DNAII-CypA full polynucleotide
<220> FEATURE:
<221> NAME/KEY: CDS
<222> LOCATION: (3712)..(5250)

<400> SEQUENCE: 23
cttccgcttc ctcgctcact gactcgctgc gctcggtcgt tcggctgcgg cgagcggtat      60
cagctcactc aaaggcggta atacggttat ccacagaatc aggggataac gcaggaaaga     120
acatgtgagc aaaaggccag caaaaggcca ggaaccgtaa aaaggccgcg ttgctggcgt     180
ttttccatag gctccgcccc cctgacgagc atcacaaaaa tcgacgctca agtcagaggt     240
ggcgaaaccc gacaggacta taaagatacc aggcgtttcc ccctggaagc tccctcgtgc     300
gctctcctgt tccgaccctg ccgcttaccg gatacctgtc cgcctttctc ccttcgggaa     360
gcgtggcgct ttctcatagc tcacgctgta ggtatctcag ttcggtgtag gtcgttcgct     420
ccaagctggg ctgtgtgcac gaaccccccg ttcagcccga ccgctgcgcc ttatccggta     480
actatcgtct tgagtccaac ccggtaagac acgacttatc gccactggca gcagccactg     540
gtaacaggat tagcagagcg aggtatgtag gcggtgctac agagttcttg aagtggtggc     600
ctaactacgg ctacactaga agaacagtat ttggtatctg cgctctgctg aagccagtta     660
ccttcggaaa aagagttggt agctcttgat ccggcaaaca aaccaccgct ggtagcggtg     720
gtttttttgt ttgcaagcag cagattacgc gcagaaaaaa aggatctcaa gaagatcctt     780
tgatcttttc tacggggtct gacgctcagt ggaacgaaaa ctcacgttaa gggattttgg     840
tcatgagatt atcaaaaagg atcttcacct agatcctttt aaattaaaaa tgaagtttta     900
aatcaatcta agtatatatg agtaaacttg gtctgacagt taccaatgct taatcagtg      960 aggcacctat ctcagcgatc tgtctatttc gttcatccat agttgcctga ctccccgtcg    1020
tgtagataac tacgatacgg gagggcttac catctggccc cagtgctgca atgataccgc    1080
gagacccacg ctcaccggct ccagatttat cagcaataaa ccagccagcc ggaagggccg    1140
agcgcagaag tggtcctgca actttatccg cctccatcca gtctattaat tgttgccggg    1200
aagctagagt aagtagttcg ccagttaata gtttgcgcaa cgttgttgcc attgctacag    1260
```

```
gcatcgtggt gtcacgctcg tcgtttggta tggcttcatt cagctccggt tcccaacgat   1320
caaggcgagt tacatgatcc cccatgttgt gcaaaaaagc ggttagctcc ttcggtcctc   1380
cgatcgttgt cagaagtaag ttggccgcag tgttatcact catggttatg gcagcactgc   1440
ataattctct tactgtcatg ccatccgtaa gatgcttttc tgtgactggt gagtactcaa   1500
ccaagtcatt ctgagaatag tgtatgcggc gaccgagttg ctcttgcccg gcgtcaatac   1560
gggataatac cgcgccacat agcagaactt taaaagtgct catcattgga aaacgttctt   1620
cggggcgaaa actctcaagg atcttaccgc tgttgagatc cagttcgatg taacccactc   1680
gtgcacccaa ctgatcttca gcatctttta ctttcaccag cgtttctggg tgagcaaaaa   1740
caggaaggca aaatgccgca aaaaagggaa taagggcgac acggaaatgt tgaatactca   1800
tactcttcct ttttcaattc agaagaactc gtcaagaagg cgatagaagg cgatgcgctg   1860
cgaatcggga gcggcgatac cgtaaagcac gaggaagcgg tcagcccatt cgccgccaag   1920
ctcttcagca atatcacggg tagccaacgc tatgtcctga tagcggtccg ccacacccag   1980
ccggccacag tcgatgaatc cagaaaagcg gccattttcc accatgatat tcggcaagca   2040
ggcatcgcca tgggtcacga cgagatcctc gccgtcgggc atgcgcgcct tgagcctggc   2100
gaacagttcg gctggcgcga gcccctgatg ctcttcgtcc agatcatcct gatcgacaag   2160
accggcttcc atccgagtac gtgctcgctc gatgcgatgt ttcgcttggt ggtcgaatgg   2220
gcaggtagcc ggatcaagcg tatgcagccg ccgcattgca tcagccatga tggatacttt   2280
ctcggcagga gcaaggtggg atgacaggag atcctgcccc ggcacttcgc ccaatagcag   2340
ccagtcccct cccgcttcag tgacaacgtc gagcacagct gcgcaaggaa cgcccgtcgt   2400
ggccagccac gatagccgcg ctgcctcgtc ctgcagttca ttcagggcac cggacaggtc   2460
ggtcttgaca aaaagaaccg ggcgcccctg cgctgacagc cggaacacgg cggcatcaga   2520
gcagccgatt gtctgttgtg cccagtcata gccgaatagc ctctccaccc aagcggccgg   2580
agaacctgcg tgcaatccat cttgttcaat catgcgaaac gatcctcatc ctgtctcttg   2640
atcagatctt gatcccctgc gccatcagat ccttggcggc aagaaagcca tccagtttac   2700
tttgcagggc ttcccaacct taccagaggg cgccccagct ggcaattccg gttcgcttgc   2760
tgtccataaa accgcccagt ctagctatcg ccatgtaagc ccactgcaag ctacctgctt   2820
tctctttgcg cttgcgtttt cccttgtcca gatagcccag tagctgacat tcatccgggg   2880
tcagcaccgt ttctgcggac tggctttcta cgtgttccgc ttcctttagc agcccttgcg   2940
ccctgaattt tgttaaaatt cgcgttaaat ttttgttaaa tcagctcatt ttttaaccaa   3000
taggccgaaa tcggcaaaat cccttataaa tcaaaagaat agaccgagat agggttgagt   3060
gttgttccag tttggaacaa gagtccacta ttaaagaacg tggactccaa cgtcaaaggg   3120
cgaaaaaccg tctatcaggg cgatggccca ctacgtgaac catcaccta atcaagtttt   3180 ttggggtcga ggtgccgtaa agcactaaat cggaaccta aagggagccc ccgatttaga   3240
gcttgacggg gaaagccggc gaacgtggcg agaaaggaag ggaagaaagc gaaaggagcg   3300
ggcgctaggg cgctggcaag tgtagcggtc acgctgcgcg taaccaccac acccgccgcg   3360
cttaatgcgc cgctacaggg cgcgtccatt cgccattcag gctgcgcaac tgttgggaag   3420
ggcgatcggt gcgggcctct tcgctattac gccagctggc gaaaggggga tgtgctgcaa   3480
ggcgattaag ttgggtaacg ccagggtttt cccagtcacg acgttgtaaa acgacggcca   3540
gtgaattgta atacgactca ctatagggcg aattgggccc tctagatgca tgctcgagcg   3600
gccgcttaat acgactcact atagaggccc tgaaaagggg ccaaaaacat gaggatcacc   3660
```

```
                                                                -continued catgtaaaag tcgacaataa ttttgtttaa ctttaagaag gagatataca t atg gcc     3717
                                                        Met Ala
                                                          1 atg cag gcc gtc aac ccc acc gtg ttc ttc gac att gcc gtc gac ggc     3765
Met Gln Ala Val Asn Pro Thr Val Phe Phe Asp Ile Ala Val Asp Gly
        5                  10                  15 gag ccc ttg ggc cgc gtc tcc ttt gag ctg ttt gca gac aag gtc cca     3813
Glu Pro Leu Gly Arg Val Ser Phe Glu Leu Phe Ala Asp Lys Val Pro
 20                  25                  30 aag aca gca gaa aat ttt cgt gct ctg agc act gga gag aaa gga ttt     3861
Lys Thr Ala Glu Asn Phe Arg Ala Leu Ser Thr Gly Glu Lys Gly Phe
 35                  40                  45                  50 ggt tat aag ggt tcc tgc ttt cac aga att att cca ggg ttt atg tgt     3909
Gly Tyr Lys Gly Ser Cys Phe His Arg Ile Ile Pro Gly Phe Met Cys
                 55                  60                  65 cag ggt ggt gac ttc aca cgc cat aat ggc act ggt ggc aag tcc atc     3957
Gln Gly Gly Asp Phe Thr Arg His Asn Gly Thr Gly Gly Lys Ser Ile
         70                  75                  80 tat ggg gag aaa ttt gaa gat gag aac ttc atc cta aag cat acg ggt     4005
Tyr Gly Glu Lys Phe Glu Asp Glu Asn Phe Ile Leu Lys His Thr Gly
     85                  90                  95 cct ggc atc ttg tcc atg gca aat gct gga ccc aac aca aat ggt tcc     4053
Pro Gly Ile Leu Ser Met Ala Asn Ala Gly Pro Asn Thr Asn Gly Ser
100                 105                 110 cag ttt ttc atc tgc act gcc aag act gag tgg ttg gat ggc aag cat     4101
Gln Phe Phe Ile Cys Thr Ala Lys Thr Glu Trp Leu Asp Gly Lys His
115                 120                 125                 130 gtg gtg ttt ggc aaa gtg aaa gaa ggc atg aat att gtg gag gcc atg     4149
Val Val Phe Gly Lys Val Lys Glu Gly Met Asn Ile Val Glu Ala Met
                135                 140                 145 gag cgc ttt ggg tcc agg aat ggc aag acc agc aag aag atc acc att     4197
Glu Arg Phe Gly Ser Arg Asn Gly Lys Thr Ser Lys Lys Ile Thr Ile
            150                 155                 160 gct gac tgt gga caa ctc gaa ggc cag cta ggc cag tct agt gga ggt     4245
Ala Asp Cys Gly Gln Leu Glu Gly Gln Leu Gly Gln Ser Ser Gly Gly
        165                 170                 175 gga aat gct cgt act cgg cga cgt gaa cgc aga gcc atg gaa cga gct     4293
Gly Asn Ala Arg Thr Arg Arg Arg Glu Arg Arg Ala Met Glu Arg Ala
    180                 185                 190 acg ctg cca caa gtg ctg gga ggt gga tct ttc gaa cgc cag cac atg     4341
Thr Leu Pro Gln Val Leu Gly Gly Gly Ser Phe Glu Arg Gln His Met
195                 200                 205                 210 gac agc cca gat ctg ggt acc gac gac gac gac aag gct gca tct atg     4389
Asp Ser Pro Asp Leu Gly Thr Asp Asp Asp Asp Lys Ala Ala Ser Met
                215                 220                 225 gct tct aac ttt act cag ttc gtt ctc gtc gac aat ggc gga act ggc     4437
Ala Ser Asn Phe Thr Gln Phe Val Leu Val Asp Asn Gly Gly Thr Gly
            230                 235                 240 gac gtg act gtc gcc cca agc aac ttc gct aac ggg gtc gct gaa tgg     4485
Asp Val Thr Val Ala Pro Ser Asn Phe Ala Asn Gly Val Ala Glu Trp
        245                 250                 255 atc agc tct aac tcg cga tca cag gct tac aaa gta acc tgt agc gtt     4533
Ile Ser Ser Asn Ser Arg Ser Gln Ala Tyr Lys Val Thr Cys Ser Val
    260                 265                 270 cgt cag agc tct gcg cag aat cgc aaa tac acc atc aaa gtc gag gtg     4581
Arg Gln Ser Ser Ala Gln Asn Arg Lys Tyr Thr Ile Lys Val Glu Val
275                 280                 285                 290 cct aaa gtg gca acc cag act gtt ggt ggt gaa gag ctt cct gta gcc     4629
Pro Lys Val Ala Thr Gln Thr Val Gly Gly Glu Glu Leu Pro Val Ala
```

|     |     |     |     |     | 295 |     |     |     | 300 |     |     |     |     | 305 |     |      |
| --- | --- | --- | --- | --- | --- | --- | --- | --- | --- | --- | --- | --- | --- | --- | --- | ---- |
| gga | tgg | aga | tct | tac | tta | aat | atg | gaa | cta | acc | att | cca | att | ttc | gcc | 4677 |
| Gly | Trp | Arg | Ser | Tyr | Leu | Asn | Met | Glu | Leu | Thr | Ile | Pro | Ile | Phe | Ala |      |
|     |     | 310 |     |     |     |     | 315 |     |     |     |     | 320 |     |     |     |      |
| acg | aat | tcc | gac | tgc | gag | ctt | att | gtt | aag | gca | atg | caa | ggt | ctc | cta | 4725 |
| Thr | Asn | Ser | Asp | Cys | Glu | Leu | Ile | Val | Lys | Ala | Met | Gln | Gly | Leu | Leu |      |
|     |     | 325 |     |     |     |     | 330 |     |     |     |     | 335 |     |     |     |      |
| aaa | gat | gga | aac | ccg | att | ccc | tcg | gcc | atc | gca | gca | aac | tcc | ggc | atc | 4773 |
| Lys | Asp | Gly | Asn | Pro | Ile | Pro | Ser | Ala | Ile | Ala | Ala | Asn | Ser | Gly | Ile |      |
|     | 340 |     |     |     |     | 345 |     |     |     |     | 350 |     |     |     |     |      |
| tac | ggt | ggt | ggt | tca | ggt | ggt | ggt | tca | tct | gca | tct | atg | gct | tct | aac | 4821 |
| Tyr | Gly | Gly | Gly | Ser | Gly | Gly | Gly | Ser | Ser | Ala | Ser | Met | Ala | Ser | Asn |      |
| 355 |     |     |     |     | 360 |     |     |     |     | 365 |     |     |     |     | 370 |      |
| ttt | act | cag | ttc | gtt | ctc | gtc | gac | aat | ggc | gga | act | ggc | gac | gtg | act | 4869 |
| Phe | Thr | Gln | Phe | Val | Leu | Val | Asp | Asn | Gly | Gly | Thr | Gly | Asp | Val | Thr |      |
|     |     |     | 375 |     |     |     |     | 380 |     |     |     |     | 385 |     |     |      |
| gtc | gcc | cca | agc | aac | ttc | gct | aac | ggg | gtc | gct | gaa | tgg | atc | agc | tct | 4917 |
| Val | Ala | Pro | Ser | Asn | Phe | Ala | Asn | Gly | Val | Ala | Glu | Trp | Ile | Ser | Ser |      |
|     |     |     | 390 |     |     |     |     | 395 |     |     |     |     | 400 |     |     |      |
| aac | tcg | cga | tca | cag | gct | tac | aaa | gta | acc | tgt | agc | gtt | cgt | cag | agc | 4965 |
| Asn | Ser | Arg | Ser | Gln | Ala | Tyr | Lys | Val | Thr | Cys | Ser | Val | Arg | Gln | Ser |      |
|     |     | 405 |     |     |     |     | 410 |     |     |     |     | 415 |     |     |     |      |
| tct | gcg | cag | aat | cgc | aaa | tac | acc | atc | aaa | gtc | gag | gtg | cct | aaa | gtg | 5013 |
| Ser | Ala | Gln | Asn | Arg | Lys | Tyr | Thr | Ile | Lys | Val | Glu | Val | Pro | Lys | Val |      |
|     | 420 |     |     |     |     | 425 |     |     |     |     | 430 |     |     |     |     |      |
| gca | acc | cag | act | gtt | ggt | ggt | gaa | gag | ctt | cct | gta | gcc | gga | tgg | aga | 5061 |
| Ala | Thr | Gln | Thr | Val | Gly | Gly | Glu | Glu | Leu | Pro | Val | Ala | Gly | Trp | Arg |      |
| 435 |     |     |     |     | 440 |     |     |     |     | 445 |     |     |     |     | 450 |      |
| tct | tac | tta | aat | atg | gaa | cta | acc | att | cca | att | ttc | gcc | acg | aat | tcc | 5109 |
| Ser | Tyr | Leu | Asn | Met | Glu | Leu | Thr | Ile | Pro | Ile | Phe | Ala | Thr | Asn | Ser |      |
|     |     |     |     | 455 |     |     |     |     | 460 |     |     |     |     | 465 |     |      |
| gac | tgc | gag | ctt | att | gtt | aag | gca | atg | caa | ggt | ctc | cta | aaa | gat | gga | 5157 |
| Asp | Cys | Glu | Leu | Ile | Val | Lys | Ala | Met | Gln | Gly | Leu | Leu | Lys | Asp | Gly |      |
|     |     |     | 470 |     |     |     |     | 475 |     |     |     |     | 480 |     |     |      |
| aac | ccg | att | ccc | tca | gca | atc | gca | gca | aac | tcc | ggc | atc | tac | ggt | ggt | 5205 |
| Asn | Pro | Ile | Pro | Ser | Ala | Ile | Ala | Ala | Asn | Ser | Gly | Ile | Tyr | Gly | Gly |      |
|     |     | 485 |     |     |     |     | 490 |     |     |     |     | 495 |     |     |     |      |
| ggt | tca | ggt | ggt | ggt | tca | tct | gca | ggt | atg | atc | agt | ctg | att | gcg |     | 5250 |
| Gly | Ser | Gly | Gly | Gly | Ser | Ser | Ala | Gly | Met | Ile | Ser | Leu | Ile | Ala |     |      |
|     | 500 |     |     |     |     | 505 |     |     |     |     | 510 |     |     |     |     |      |

```
gcgttagcgg tagatcgcgt tatcggcatg aaaacgcca tgccgtggaa cctgcctgcc    5310
gatctcgcct ggtttaaacg caacaccttaa aataaacccg tgattatggg ccgccatacc    5370
tgggaatcaa tcggtcgtcc gttgccagga cgcaaaaata ttatcctcag cagtcaaccg    5430
ggtacggacg atcgcgtaac gtgggtgaag tcggtggatg aagccatcgc ggcgtgtggt    5490
gacgtaccag aaatcatggt gattggcggc ggtcgcgttt atgaacagtt cttgccaaaa    5550
gcgcaaaaac tgtatctgac gcatatcgac gcagaagtgg aaggcgacac ccatttcccg    5610
gattacgagc cggatgactg ggaatcggta ttcagcgagt ccacgatgc tgatgcgcag    5670 aactctcaca gctattgctt tgagattctg gagcggcgga actcgaggga tccgagctcg    5730
gtaccaagct ggcgtaatc atggtcatag ctgtttcctg tgtgaaattg ttatccgctc    5790
acaattccac acaacatacg agccggaagc ataaagtgta aagcctgggg tgcctaatga    5850
gtgagctaac tcacattaat tgcgttgcgc tcactgcccg ctttccagtc gggaaacctg    5910
tcgtgccagc tgcattaatg aatcggccaa cgcgcgggga gaggcggttt gcgtattggg    5970
cgct                                                                 5974
```

<210> SEQ ID NO 24
<211> LENGTH: 513
<212> TYPE: PRT
<213> ORGANISM: Artificial Sequence
<220> FEATURE:
<223> OTHER INFORMATION: Description of Artificial Sequence: Synthetic plasmid DNAII-CypA full polypeptide

<400> SEQUENCE: 24

```
Met Ala Met Gln Ala Val Asn Pro Thr Val Phe Phe Asp Ile Ala Val
1               5                   10                  15

Asp Gly Glu Pro Leu Gly Arg Val Ser Phe Glu Leu Phe Ala Asp Lys
            20                  25                  30

Val Pro Lys Thr Ala Glu Asn Phe Arg Ala Leu Ser Thr Gly Glu Lys
        35                  40                  45

Gly Phe Gly Tyr Lys Gly Ser Cys Phe His Arg Ile Ile Pro Gly Phe
    50                  55                  60

Met Cys Gln Gly Gly Asp Phe Thr Arg His Asn Gly Thr Gly Gly Lys
65                  70                  75                  80

Ser Ile Tyr Gly Glu Lys Phe Glu Asp Glu Asn Phe Ile Leu Lys His
                85                  90                  95

Thr Gly Pro Gly Ile Leu Ser Met Ala Asn Ala Gly Pro Asn Thr Asn
            100                 105                 110

Gly Ser Gln Phe Phe Ile Cys Thr Ala Lys Thr Glu Trp Leu Asp Gly
        115                 120                 125

Lys His Val Val Phe Gly Lys Val Lys Glu Gly Met Asn Ile Val Glu
    130                 135                 140

Ala Met Glu Arg Phe Gly Ser Arg Asn Gly Lys Thr Ser Lys Lys Ile
145                 150                 155                 160

Thr Ile Ala Asp Cys Gly Gln Leu Glu Gly Gln Leu Gly Gln Ser Ser
                165                 170                 175

Gly Gly Gly Asn Ala Arg Thr Arg Arg Glu Arg Arg Ala Met Glu
            180                 185                 190

Arg Ala Thr Leu Pro Gln Val Leu Gly Gly Ser Phe Glu Arg Gln
        195                 200                 205

His Met Asp Ser Pro Asp Leu Gly Thr Asp Asp Asp Lys Ala Ala
    210                 215                 220

Ser Met Ala Ser Asn Phe Thr Gln Phe Val Leu Val Asp Asn Gly Gly
225                 230                 235                 240

Thr Gly Asp Val Thr Val Ala Pro Ser Asn Phe Ala Asn Gly Val Ala
                245                 250                 255

Glu Trp Ile Ser Ser Asn Ser Arg Ser Gln Ala Tyr Lys Val Thr Cys
            260                 265                 270

Ser Val Arg Gln Ser Ser Ala Gln Asn Arg Lys Tyr Thr Ile Lys Val
        275                 280                 285

Glu Val Pro Lys Val Ala Thr Gln Thr Val Gly Gly Glu Glu Leu Pro
    290                 295                 300

Val Ala Gly Trp Arg Ser Tyr Leu Asn Met Glu Leu Thr Ile Pro Ile
305                 310                 315                 320

Phe Ala Thr Asn Ser Asp Cys Glu Leu Ile Val Lys Ala Met Gln Gly
                325                 330                 335

Leu Leu Lys Asp Gly Asn Pro Ile Pro Ser Ala Ile Ala Ala Asn Ser
            340                 345                 350

Gly Ile Tyr Gly Gly Gly Ser Gly Gly Gly Ser Ser Ala Ser Met Ala
```

355                 360                 365
Ser Asn Phe Thr Gln Phe Val Leu Val Asp Asn Gly Gly Thr Gly Asp
    370                 375                 380

Val Thr Val Ala Pro Ser Asn Phe Ala Asn Gly Val Ala Glu Trp Ile
385                 390                 395                 400

Ser Ser Asn Ser Arg Ser Gln Ala Tyr Lys Val Thr Cys Ser Val Arg
                405                 410                 415

Gln Ser Ser Ala Gln Asn Arg Lys Tyr Thr Ile Lys Val Glu Val Pro
            420                 425                 430

Lys Val Ala Thr Gln Thr Val Gly Gly Glu Glu Leu Pro Val Ala Gly
        435                 440                 445

Trp Arg Ser Tyr Leu Asn Met Glu Leu Thr Ile Pro Ile Phe Ala Thr
    450                 455                 460

Asn Ser Asp Cys Glu Leu Ile Val Lys Ala Met Gln Gly Leu Leu Lys
465                 470                 475                 480

Asp Gly Asn Pro Ile Pro Ser Ala Ile Ala Ala Asn Ser Gly Ile Tyr
                485                 490                 495

Gly Gly Gly Ser Gly Gly Gly Ser Ser Ala Gly Met Ile Ser Leu Ile
            500                 505                 510

Ala

<210> SEQ ID NO 25
<211> LENGTH: 47
<212> TYPE: DNA
<213> ORGANISM: Artificial Sequence
<220> FEATURE:
<223> OTHER INFORMATION: Description of Artificial Sequence: Synthetic
      fp1 primer

<400> SEQUENCE: 25
ttaatacgac tcactataga aaagtcgaca ataattttgt ttaactt                    47

<210> SEQ ID NO 26
<211> LENGTH: 65
<212> TYPE: DNA
<213> ORGANISM: Artificial Sequence
<220> FEATURE:
<223> OTHER INFORMATION: Description of Artificial Sequence: Synthetic
      fp2 primer

<400> SEQUENCE: 26
ttaatacgac tcactataga ggccctgaaa aagggccaaa agtcgacaat aattttgttt     60
aactt                                                                 65

<210> SEQ ID NO 27
<211> LENGTH: 67
<212> TYPE: DNA
<213> ORGANISM: Artificial Sequence
<220> FEATURE:
<223> OTHER INFORMATION: Description of Artificial Sequence: Synthetic
      fp3 primer

<400> SEQUENCE: 27
ttaatacgac tcactataga acatgaggat cacccatgta aaagtcgaca ataattttgt     60
ttaactt                                                               67

<210> SEQ ID NO 28
<211> LENGTH: 36
<212> TYPE: DNA
<213> ORGANISM: Artificial Sequence -continued

```
<220> FEATURE:
<223> OTHER INFORMATION: Description of Artificial Sequence: Synthetic
      fp4 primer

<400> SEQUENCE: 28
ttaatacgac tcactataga ggccctgaaa aagggc                              36

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic
      rp1 primer

<400> SEQUENCE: 29
tcattacgca atcagactga tcatac                                        26

<210> SEQ ID NO 30
<211> LENGTH: 47
<212> TYPE: DNA
<213> ORGANISM: Artificial Sequence
<220> FEATURE:
<223> OTHER INFORMATION: Description of Artificial Sequence: Synthetic
      rp2 primer

<400> SEQUENCE: 30
ttacttgtcg tcatcgtcct tgtagtccgc aatcagactg atcatac                  47

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      rp3 primer

<400> SEQUENCE: 31
cagaatctca aagcaatagc                                               20

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      secM peptide
<220> FEATURE:
<221> NAME/KEY: MOD_RES
<222> LOCATION: (2)..(5)
<223> OTHER INFORMATION: Any naturally occurring amino acid
<220> FEATURE:
<221> NAME/KEY: MOD_RES
<222> LOCATION: (8)..(11)
<223> OTHER INFORMATION: Any naturally occurring amino acid

<400> SEQUENCE: 32

Phe Xaa Xaa Xaa Xaa Trp Ile Xaa Xaa Xaa Xaa Gly Ile Arg Ala Gly
1               5                   10                  15

Pro

<210> SEQ ID NO 33
<211> LENGTH: 23
<212> TYPE: PRT
<213> ORGANISM: Artificial Sequence
<220> FEATURE:
<223> OTHER INFORMATION: Description of Artificial Sequence: Synthetic
      Bap peptide
```

<400> SEQUENCE: 33

Gly Asn Ala Arg Thr Arg Arg Glu Arg Ala Met Glu Arg Ala
1               5                   10                  15

Thr Leu Pro Gln Val Leu Gly
            20

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      Rev peptide

<400> SEQUENCE: 34

Thr Arg Gln Ala Arg Arg Asn Arg Arg Arg Arg Trp Arg Glu Arg Gln
1               5                   10                  15

Arg

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide based on the BIV Tat sequence

<400> SEQUENCE: 35

Ser Gly Pro Arg Pro Arg Gly Thr Arg Gly Lys Gly Arg Arg Ile Arg
1               5                   10                  15

Arg

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      linker 1 peptide

<400> SEQUENCE: 36

Gly Gly Gly Ser Gly Gly Gly Ser
1               5

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      linker 2 peptide

<400> SEQUENCE: 37

Gly Gly Gly Ser Gly Gly Gly Ser Gly Gly Gly Ser
1               5                   10

<210> SEQ ID NO 38
<211> LENGTH: 17
<212> TYPE: RNA
<213> ORGANISM: Artificial Sequence
<220> FEATURE:
<223> OTHER INFORMATION: Description of Artificial Sequence: Synthetic
      boxB oligonucleotide

<400> SEQUENCE: 38

```
ggcccugaaa aagggcc                                                    17
```

<210> SEQ ID NO 39
<211> LENGTH: 35
<212> TYPE: RNA
<213> ORGANISM: Artificial Sequence
<220> FEATURE:
<223> OTHER INFORMATION: Description of Artificial Sequence: Synthetic
      apI oligonucleotide

<400> SEQUENCE: 39

```
ggcuggacuc guacuucggu acuggagaaa cagcc                                35
```

<210> SEQ ID NO 40
<211> LENGTH: 27
<212> TYPE: RNA
<213> ORGANISM: Artificial Sequence
<220> FEATURE:
<223> OTHER INFORMATION: Description of Artificial Sequence: Synthetic
      apII oligonucleotide

<400> SEQUENCE: 40

```
ggugucuugg agugcugauc ggacacc                                         27
```

<210> SEQ ID NO 41
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide based on the BIV TAR sequence

<400> SEQUENCE: 41

```
gcucguguag cucauuagcu ccgagc                                          26
```

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Synthetic
      consensus sequence 1 peptide
<220> FEATURE:
<221> NAME/KEY: MOD_RES
<222> LOCATION: (2)..(3)
<223> OTHER INFORMATION: Any amino acid

<400> SEQUENCE: 42

Arg Xaa Xaa Arg
1

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus sequence 2 peptide
<220> FEATURE:
<221> NAME/KEY: MOD_RES
<222> LOCATION: (3)..(3)
<223> OTHER INFORMATION: Any amino acid

<400> SEQUENCE: 43

Arg Arg Xaa Arg Arg
1               5

-continued

```
<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide based on the HIV-1 Tat sequence

<400> SEQUENCE: 44

Gly Arg Lys Lys Arg Arg Gln Arg Arg Arg
1               5                   10

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide based on the JDV Tat sequence

<400> SEQUENCE: 45

Gly Arg Arg Lys Lys Arg Gly Thr Arg Gly Lys Gly Arg Lys Ile His
1               5                   10                  15

Tyr

<210> SEQ ID NO 46
<211> LENGTH: 22
<212> TYPE: PRT
<213> ORGANISM: Artificial Sequence
<220> FEATURE:
<223> OTHER INFORMATION: Description of Artificial Sequence: Synthetic
      lambda N peptide

<400> SEQUENCE: 46

Met Asp Ala Gln Thr Arg Arg Arg Glu Arg Arg Ala Glu Lys Gln Ala
1               5                   10                  15

Gln Trp Lys Ala Ala Asn
            20

<210> SEQ ID NO 47
<211> LENGTH: 22
<212> TYPE: PRT
<213> ORGANISM: Artificial Sequence
<220> FEATURE:
<223> OTHER INFORMATION: Description of Artificial Sequence: Synthetic
      lambda N mutant peptide

<400> SEQUENCE: 47

Gly Asn Ala Arg Thr Arg Arg Arg Glu Arg Arg Ala Glu Lys Gln Ala
1               5                   10                  15

Gln Trp Lys Ala Ala Asn
            20

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      P22N peptide

<400> SEQUENCE: 48

Asn Ala Lys Thr Arg Arg His Glu Arg Arg Arg Lys Leu Ala Ile Glu
1               5                   10                  15

Arg
```

```
<210> SEQ ID NO 49
<211> LENGTH: 18
<212> TYPE: PRT
<213> ORGANISM: Artificial Sequence
<220> FEATURE:
<223> OTHER INFORMATION: Description of Artificial Sequence: Synthetic
      phi21N peptide

<400> SEQUENCE: 49

Thr Ala Lys Thr Arg Tyr Lys Ala Arg Arg Ala Glu Leu Ile Ala Glu
1               5                   10                  15

Arg Arg

<210> SEQ ID NO 50
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide based on the BMV Gag sequence

<400> SEQUENCE: 50

Lys Met Thr Arg Ala Gln Arg Arg Ala Ala Ala Arg Arg Asn Arg Trp
1               5                   10                  15

Thr Ala Arg

<210> SEQ ID NO 51
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide based on the CCMV Gag sequence

<400> SEQUENCE: 51

Lys Leu Thr Arg Ala Gln Arg Arg Ala Ala Ala Arg Lys Asn Lys Arg
1               5                   10                  15

Asn Thr Arg

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      Spuma Gag peptide

<400> SEQUENCE: 52

Thr Arg Ala Leu Arg Arg Gln Leu Ala Glu Arg
1               5                   10

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide based on the Yeast PRP6 sequence

<400> SEQUENCE: 53

Thr Arg Arg Asn Lys Arg Asn Arg Ile Gln Glu Gln Leu Asn Arg Lys
1               5                   10                  15

<210> SEQ ID NO 54
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide based on the Human U2AF sequence

<400> SEQUENCE: 54

Ser Gln Met Thr Arg Gln Ala Arg Arg Leu Tyr Val
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide based on the HTLV-II Rex sequence

<400> SEQUENCE: 55

Thr Arg Arg Gln Arg Thr Arg Arg Ala Arg Arg Asn Arg
1               5                   10

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide based on the FHV coat sequence

<400> SEQUENCE: 56

Arg Arg Arg Arg Asn Arg Thr Arg Arg Asn Arg Arg Arg Val Arg
1               5                   10                  15

<210> SEQ ID NO 57
<211> LENGTH: 19
<212> TYPE: PRT
<213> ORGANISM: Artificial Sequence
<220> FEATURE:
<223> OTHER INFORMATION: Description of Artificial Sequence: Synthetic
      S3 peptide

<400> SEQUENCE: 57

Arg Arg Val Ala Phe Arg Arg Ile Val Arg Lys Ala Ile Thr Arg Ala
1               5                   10                  15

Gln Arg Arg

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      S7 peptide

<400> SEQUENCE: 58

Lys Thr Lys Leu Glu Arg Arg Asn Lys
1               5

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      S28 peptide

<400> SEQUENCE: 59
```

```
Arg Lys Leu Arg Val His Arg Arg Asn Asn Arg
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Description of Artificial Sequence: Synthetic
      L16 peptide

<400> SEQUENCE: 60

Arg Arg Ala Met Ser Arg Lys Phe Arg Arg Asn Ser Lys
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      L35 peptide

<400> SEQUENCE: 61

Arg Ala Lys Lys Thr Arg Ala Leu Arg Arg
1               5                   10

<210> SEQ ID NO 62
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide based on the HIV-1 TAR sequence

<400> SEQUENCE: 62
ccagaucuga gccugggagc ucucugg                                            27

<210> SEQ ID NO 63
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide based on the JDV TAR sequence

<400> SEQUENCE: 63
gcucuggaua gcugacagcu ccgagc                                             26

<210> SEQ ID NO 64
<211> LENGTH: 15
<212> TYPE: RNA
<213> ORGANISM: Artificial Sequence
<220> FEATURE:
<223> OTHER INFORMATION: Description of Artificial Sequence: Synthetic
      P22 boxB oligonucleotide

<400> SEQUENCE: 64
gcgcugacaa agcgc                                                         15

<210> SEQ ID NO 65
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide based on the HIV-1 RRE sequence
```

```
<400> SEQUENCE: 65
ggucugggcg cagcgcaagc ugacgguaca ggcc                               34

<210> SEQ ID NO 66
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 66

His His His His His His
1               5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      FLAG tag

<400> SEQUENCE: 67

Asp Tyr Lys Asp Asp Asp Asp Lys
1               5
```